US007662625B2

(12) United States Patent
Stern et al.

(10) Patent No.: US 7,662,625 B2
(45) Date of Patent: Feb. 16, 2010

(54) METHODS FOR DETECTING THE DIFFERENTIATION STATUS OF CELLS USING 5T4 ANTIGEN EXPRESSION

(75) Inventors: Peter L. Stern, Manchester (DE); Miles W. Carroll, Oxford (DE); Christopher M. Ward, Manchester (DE)

(73) Assignee: Cancer Research Technology Limited, London (GB)

( * ) Notice: Subject to any disclaimer, the term of this patent is extended or adjusted under 35 U.S.C. 154(b) by 0 days.

(21) Appl. No.: 10/520,502

(22) PCT Filed: Jul. 2, 2003

(86) PCT No.: PCT/GB03/02836

§ 371 (c)(1),
(2), (4) Date: Jan. 3, 2005

(87) PCT Pub. No.: WO2004/005926

PCT Pub. Date: Jan. 15, 2004

(65) Prior Publication Data

US 2005/0260591 A1 Nov. 24, 2005

(30) Foreign Application Priority Data

Jul. 2, 2002 (DE) .................................. 0215287

(51) Int. Cl.
*C12N 5/00* (2006.01)
*C12N 5/08* (2006.01)
*G01N 33/53* (2006.01)

(52) U.S. Cl. ........................... 435/325; 435/6; 435/366; 435/7.2

(58) Field of Classification Search ....................... None
See application file for complete search history.

(56) References Cited

U.S. PATENT DOCUMENTS 6,312,683 B1  11/2001  Carroll et al.

FOREIGN PATENT DOCUMENTS

EP              0336562 A    10/1989

OTHER PUBLICATIONS

Southall, PJ et al. Br J Cancer 61(1):abstract 1990.*
Boyle, JM et al. Hum Genet 94:455-458, 1990.*
Ward, CM et al. Exp Cell Res, pp. 12-14, e-pub ahead of print, Apr. 14, 2006.*
Ward, CM et al. J Cell Sci 116(22):4533-4542, 2003.*
Southall, PJ et al. Br J Cancer 61:89-95, 1990.*
Ward, CM et al. Exp Cell Res 293:229-238, 2004.*
Stem Cells: Scientific Progress and Future Research Directions. Chapter 1 (pp. 1-4) and Chapter 4 (pp. 23-42). Department of Health and Human Services. Jun. 2001. <http://stemcells.nih.gov/info/scireport/2001report>.*

Ali, A., et al. "The pattern of expression of the 5T4 oncofoetal antigen on normal, dysplastic and malignant oral mucosa", *Oral Oncology* (2001) 37:57-64.
Awan, Abida, et al. "5T4 Interacts with TIP-2/GIPC, a PDZ Protein, with Implications for Metastasis", *Biochemical and Biophysical Research Communications* (2002) 290:1030-1036.
Carsberg, Catherine J., et al. "Metastasis-Associated 5T4 Antigen Disrupts Cell-Cell Contacts and Induces Cellular Motility in Epithelial Cells", *Int. J. Cancer* (1996) 68:84-92.
Carsberg, Catherine J., et al, "Metastasis-associated 5T4 oncofoetal antigen is concentrated at microvillus projections of the plasma membrane", *Journal of Cell Science* (1995) 108:2905-2916.
Forsberg, G., et al. "Therapy of human non-small-cell lung carcinoma using antibody targeting of a modified superantigen", *British Journal of Cancer* (2001) 85(1):129-136.
Hole, N., et al. "A 72Kd trophoblast glycoprotein defined by a monoclonal antibody",*Br. J. Cancer* (1988) 57:239-246.
Hole, N., et al. "Isolation and Characterization of 5T4, A Tumour-Associated Antigen", *Int. J. Cancer* (1990) 45:179-184.
King, Karen W., et al. "Organisation of the mouse and human 5T4 oncofoetal leucine-rich glycoprotein genes and expression in foetal and adult murine tissues", *Biochimica et Biophysica Acta* (1999) 1445:257-270.
Mulder, W. Mieke C., et al. "Low Intercellular Adhesion Molecule 1 and High 5T4 Expression on Tumor Cells Correlate with Reduced Disease-free Survival in Colorectal Carcinoma Patients", *Clinical Cancer Research* (1997) 3:1923-1930.
Shaw, David M., et al. "Glycosylation and epitope mapping of the 5T4 glycoprotein oncofoetal antigen" *Biochem J.* (2002) 363:137-145.
Southall, P.J., et al. "Immunohistological distribution of 5T4 antigen in normal and malignant tissues", *Br. J. Cancer* (1990) 61:89-95.
Starzynska T., et al. "Prognostic significance of 5T4 oncofetal antigen expression in colorectal carcinoma", *Br. J, Cancer* (1994) 69:899-902.
Starzynska, T., et al. "The expression of 5T4 antigen in colorectal and gastric carcinoma", *Br. J. Cancer* (1992) 68:867-869.
Starzynska, T., et al. "5T4 oncofetal in gastric carcinoma and its clinical significance", *European Journal of Gastroenterology & Hepatology* (1998) 10(6):479-484.
Wrigley, E., et al. "5T4 oncofetal antigen expression in ovarian carcinoma", *Int. J. Gynecol Cancer* (1995) 5:269-274.
Niwa, H., et al. "Quantitative expression of Oct.-3/4 defines differentiation, dedifferentiation or self-renewal of ES cells", *nature genetics* (2000) 24(4):372-376.
Chung, Young, et al. "Embryonic and extraembryonic stem cell lines derived from single mouse blastomeres", *Nature* (2006) 439:216-219.

* cited by examiner

*Primary Examiner*—Deborah Crouch
*Assistant Examiner*—Marcia S Noble
(74) *Attorney, Agent, or Firm*—Marshall, Gerstein & Borun LLP

(57) ABSTRACT

The present invention relates to methods for detecting the differentiation status of stem cells comprising detecting the expression of 5T4 antigen in said stem cells. The present invention also relates to methods for separating populations of undifferentiated or differentiated mammalian stem cells from a mixture of differentiated and undifferentiated stem cells through detection of 5T4 expression.

10 Claims, 34 Drawing Sheets

Figure 4
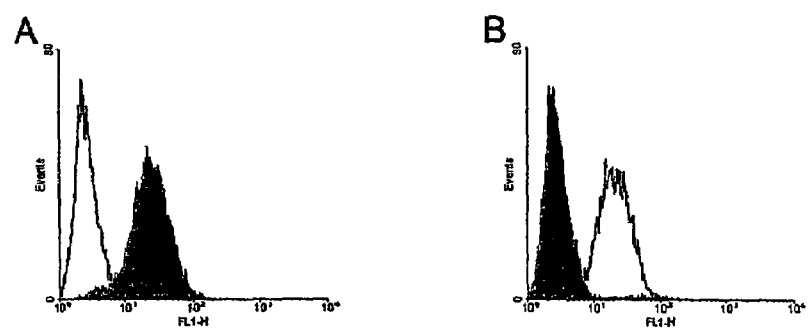
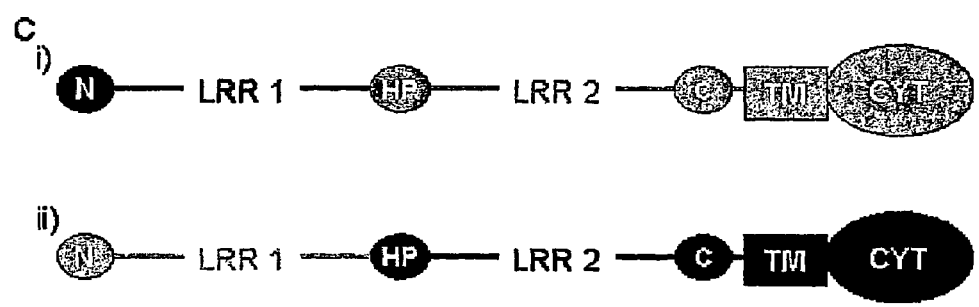

Figure 19
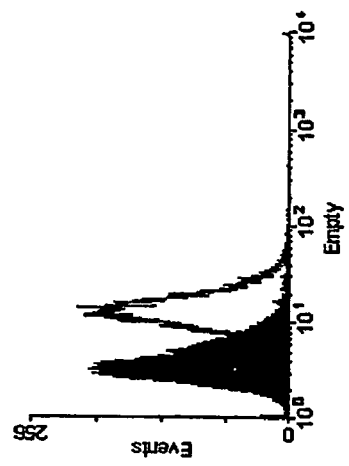
Tera2 clone13
+ ve control for 5T4
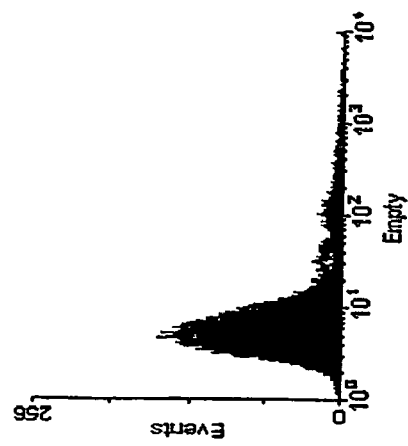
pefs

5T4 oncofoetal antigen expression on GCT27 grown on pef feeders or on gelatin coated dishes.

5T4 oncofoetal antigen expression on GCT35 grown on pef feeders or on gelatin coated dishes.

Figure 22b
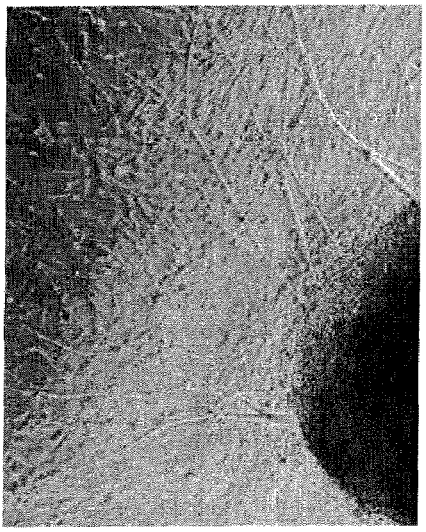
Differentiated ES colony (x100) on fibronectin coated plates and no pefs
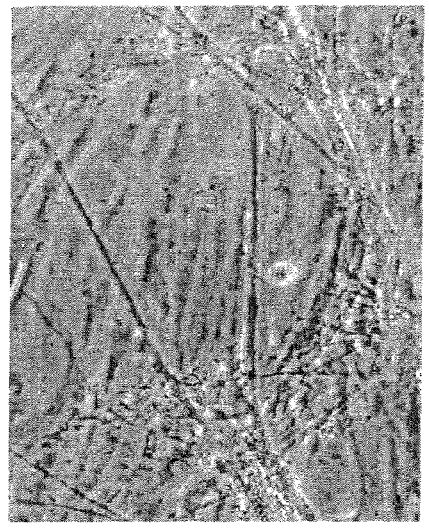
Differentiation of neural cells at the edge of the colony (x400)
Figure 22a
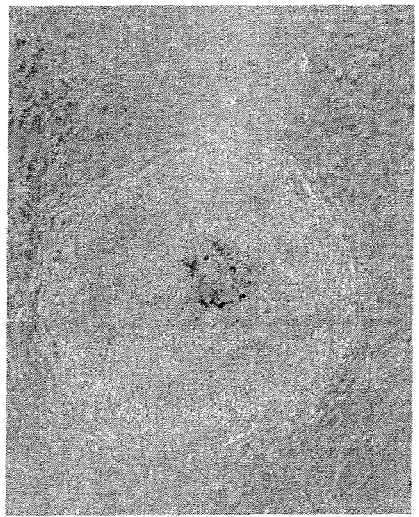
Undifferentiated ES colony on pefs (x100)
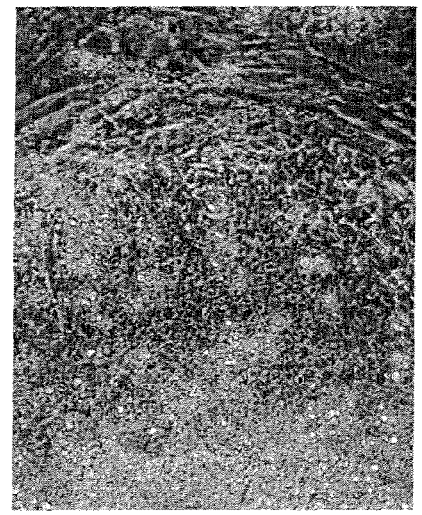
Undifferentiated ES colony (x400) showing edge and feeders Expression of 5T4 in hES cells Figure 23a: "Undifferentiated" hES cells obtained from disaggregated colonies grown on pefs Figure 23b: Differentiated hES cells obtained from colonies grown on fibronectin coated plates and no pefs for 7 days Figure 24: Dual 5T4/Oct-4 staining of hES colony on pefs with a few areas of loss of Oct4 and concomitant upregulation of 5T4

Figure 25: Dual 5T4/Oct-4 staining of hES colony with several areas of loss of Oct4 and concomitant upregulation of 5T4

Figure 26: Dual 5T4/Oct-4 staining of hES colony showing more extensive 5T4 expression which is mutually exclusive with OCT-4

Figure 27 Dual 5T4/Oct-4 staining of hES colony showing more extensive 5T4 expression which is mutually exclusive with OCT-4

Figure 28: Confocal microscopy of dual 5T4 and OCT-4 labelling of two differentiating ES colonies.

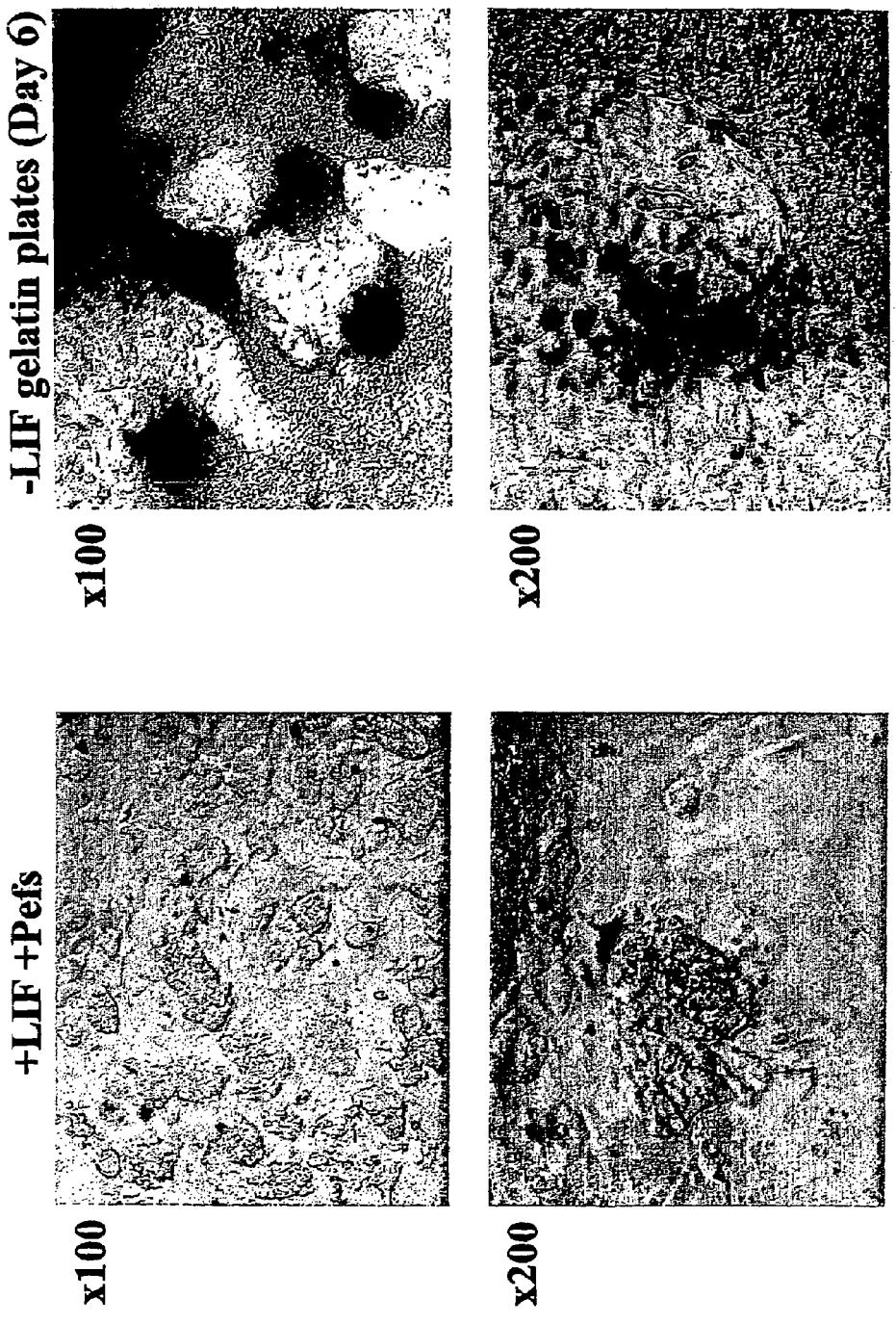
Figure 30 ß-gal staining of undifferentiated and differentiated 5T4 KO ES cells (Clone B7)

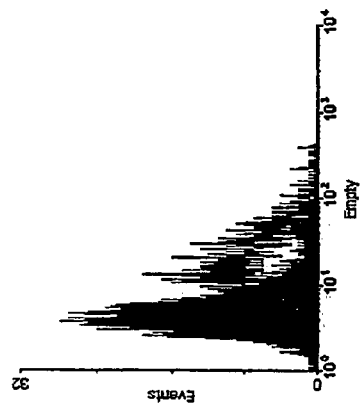
Figure 31: Expression of cell-surface 5T4 in MESC ES cells differentiated for 12 days as suspended embryoid bodies
Differentiation of MESC ES cells as suspended embryoid bodies was performed by transferring undifferentiated cells to bacteriological Petri dishes and subsequent growth in DMEMSR lacking LIF. The medium was changed daily.

SEQUENCE LISTING

```
<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
<223> OTHER INFORMATION: PCR primer 5T4 F

<400> SEQUENCE: 1
aactgccgag tctcagatac c                                              21
```

```
<210> SEQ ID NO 2
<211> LENGTH: 22
<212> TYPE: DNA
<213> ORGANISM: Artificial Sequence
<220> FEATURE:
<223> OTHER INFORMATION: PCR primer 5T4R

<400> SEQUENCE: 2
atgataccct tccatgtgat cc                                              22

<210> SEQ ID NO 3
<211> LENGTH: 20
<212> TYPE: DNA
<213> ORGANISM: Artificial Sequence
<220> FEATURE:
<223> OTHER INFORMATION: PCR primer b tubulin F

<400> SEQUENCE: 3
tcactgtgcc tgaacttacc                                                 20

<210> SEQ ID NO 4
<211> LENGTH: 20
<212> TYPE: DNA
<213> ORGANISM: Artificial Sequence
<220> FEATURE:
<223> OTHER INFORMATION: PCR primer b tubulin R

<400> SEQUENCE: 4
ggaacatagc cgtaaactgc                                                 20

<210> SEQ ID NO 5
<211> LENGTH: 20
<212> TYPE: DNA
<213> ORGANISM: Artificial Sequence
<220> FEATURE:
<223> OTHER INFORMATION: PCR primer Fgf-5 F

<400> SEQUENCE: 5
ggcagaagta gcgcgacgtt                                                 20

<210> SEQ ID NO 6
<211> LENGTH: 20
<212> TYPE: DNA
<213> ORGANISM: Artificial Sequence
<220> FEATURE:
<223> OTHER INFORMATION: PCR primer Fgf-5 R

<400> SEQUENCE: 6
tccggttgct cggactgctt                                                 20

<210> SEQ ID NO 7
<211> LENGTH: 18
<212> TYPE: DNA
<213> ORGANISM: Artificial Sequence
<220> FEATURE:
<223> OTHER INFORMATION: PCR primer Bmp-2 F

<400> SEQUENCE: 7
gagatgagtg ggaaaacg                                                   18

<210> SEQ ID NO 8
<211> LENGTH: 20
<212> TYPE: DNA
<213> ORGANISM: Artificial Sequence
<220> FEATURE:
```

```
<223> OTHER INFORMATION: PCR primer Bmp-2 R

<400> SEQUENCE: 8
gcagtaaaag gcatgatagc                                                    20

<210> SEQ ID NO 9
<211> LENGTH: 18
<212> TYPE: DNA
<213> ORGANISM: Artificial Sequence
<220> FEATURE:
<223> OTHER INFORMATION: PCR primer globin F

<400> SEQUENCE: 9
gatgaagaat gagagagc                                                      18

<210> SEQ ID NO 10
<211> LENGTH: 19
<212> TYPE: DNA
<213> ORGANISM: Artificial Sequence
<220> FEATURE:
<223> OTHER INFORMATION: PCR primer globin R

<400> SEQUENCE: 10
agtcaggata gaagacagg                                                     19

<210> SEQ ID NO 11
<211> LENGTH: 22
<212> TYPE: DNA
<213> ORGANISM: Artificial Sequence
<220> FEATURE:
<223> OTHER INFORMATION: PCR primer Oct 3/4 F

<400> SEQUENCE: 11
agaaggagct agaacagttt gc                                                 22

<210> SEQ ID NO 12
<211> LENGTH: 20
<212> TYPE: DNA
<213> ORGANISM: Artificial Sequence
<220> FEATURE:
<223> OTHER INFORMATION: PCR primer Oct 3/4 R

<400> SEQUENCE: 12
cggttacaga accatactcg                                                    20

<210> SEQ ID NO 13
<211> LENGTH: 18
<212> TYPE: DNA
<213> ORGANISM: Artificial Sequence
<220> FEATURE:
<223> OTHER INFORMATION: PCR primer Rex-1 F

<400> SEQUENCE: 13
tgaccctaaa gcaagacg                                                      18

<210> SEQ ID NO 14
<211> LENGTH: 22
<212> TYPE: DNA
<213> ORGANISM: Artificial Sequence
<220> FEATURE:
<223> OTHER INFORMATION: PCR primer Rex-1 R

<400> SEQUENCE: 14
ataagacacc acagtacaca cc                                                 22
```

METHODS FOR DETECTING THE DIFFERENTIATION STATUS OF CELLS USING 5T4 ANTIGEN EXPRESSION

RELATED APPLICATIONS

This application is a U.S. National Phase Application under 35 U.S.C. § 371 of PCT/GB2003/002836, filed Jul. 2, 2003, which claims benefit of priority from U.S. patent application Ser. No. 10/485,655, filed Oct. 9, 2003, and GB Patent Application 0215287.4, filed Jul. 2, 2002. All three applications are hereby incorporated in their entireties as if fully set forth.

FIELD OF THE INVENTION

The present invention relates to the identification that expression of 5T4 antigen is switched on during stem cell differentiation. Accordingly, detection of 5T4 expression can be used as a positive indicator of the differentiation status of stem cells and a negative indicator of pluripotency.

BACKGROUND TO THE INVENTION

Mammalian stem cells are undifferentiated, primitive cells which have the ability both to multiply and to differentiate into specific kinds of cells. Embryos provide a high concentration of stem cells and stem cell lines derived from embryos, embryonic stem (ES) cells, are pluripotent, thus possessing the capability of developing into any cell. These cells are immortal and can be maintained in an undifferentiated state in culture or directed to undergo differentiation into extra embryonic or somatic lineages. More recently, it has been recognised that embryonic germ (EG) cells i.e. cells derived from primordial germ cells may have similar properties to ES cells. Other stem cells may be derived from adults and include mesenchymal, epithelial and neural stem cells.

Such stem cells represent a major potential for cell therapies for regenerative medicine as differentiated cells can be generated for transplantation, may be genetically modified and can be transplanted as pure populations or, following tissue engineering, as tissues or physiologically functional parts of organs (organoids). ES cells are also useful models for studying the cellular and molecular biology of early development and functional genomics. In vitro culture of stem cells can also provide a useful system for drug screening and drug discovery. ES cells derived from mouse embryos are routinely used in a number of laboratory techniques ranging from gene knockout studies, for example generating "knock out" mice models, to transplantation therapies (Sato el al. (2001)).

Stem cells are generally difficult to culture in vitro and careful control of culture conditions, including the appropriate quality of serum and culture medium, is require. This is particularly important if such cells are to be genetically modified or manipulated to introduce genetic mutations, to be grown on a large scale or to direct their differentiation towards specific cell types. In addition, careful control and analysis of the differentiation status is required to ensure that the cultured stem cells are suited for their particular use. The selection of appropriate starting cells for directing appropriate phenotypic differentiation is essential as failure can lead not only to a lack of benefit but also to significant side-effects which can include proliferation of differentiated cells. In particular, if cells are not fully differentiated at the time of implantation there is always the possibility of tumour formation. It is therefore clearly important to be able to confirm and select for the undifferentiated integrity or differentiation state of cells within a stem cell population.

Some makers of the status of stem cells are known. Markers currently used for analysis of the undiffereniated integrity of ES cells include Oct 3/4 (Rathjen et al. (1999)), Rex-1 (Ben-Susbhan et al. (1998)), the cell-surface Forssman antigen (Willison et al. (1978); Ling et al. (1997)) and alkaine phosphatase (Rathjen et al. (1999)) (Table 1). All these markers are expressed in undifferentiated ES cells and their levels decrease upon differentiation, However, they are not useful for predicting both the undifferentiated integrity and differentiation state of ES cells since they decrease relatively slowly following the onset of differentiation (Lake et al. (2000); Rathjen et al. (1999)). Additionally, with the exception of the Forssman antigen, the analyses are destructive to cells and require relatively large numbers of cells for RNA extraction.

Removal of leukemia inhibitory factor (LIF) from the medium results in mouse ES cell differentiation (Smith et al. (1992)), characterised by the upregulation of transcript markers such as fibroblast growth factor-5 (Fgf-5), zeta globin (ZG) and Flk-1 (Table 3). However, these markers are transiently expressed and present only on a sub-population of cells thereby limiting their use as single assay markers of ES cell integrity and differentiation.

To date, there is no marker that can accurately assess both the undifferentiated integrity and differentiated state of stem cells. Current analyses of these parameters are time-consuming, often destructive to cells, and require several different markers (Weinhold et al. (2000); Lake et al (2000); Rathjen et al. (1999)). Analysis in a single, non-destructive assay would be a valuable tool for a wide range of ES cell techniques (Lake et al. (2000); Thorey et al. (1998); Niwa et al. (2000); Wakayama et al (1999)).

The 5T4 oncofoetal antigen is a 72 kDa highly glycosylated single pass transmembrane glycoprotein originally isolated from human placental trophoblast (Hole, N. & Stern, P. L. (1988); Hole, N. & Stern, P. L. (1990) and Myers, K. A. et al. (1994). 5T4 has been extensively characterised (see, for example, WO 89/07947). It exhibits restricted expression patterns in human adult issues, being expressed by trophoblast and a few specialised adult epithelia, but is upregulated on many carcinomas, with tumour overexpression correlating with poorer clinical outcome in ovarian, gastric and colorectal cancers. (Southall, P. J. et al. (1990); Wrigley, E. et al. (1995); Starzynska, T. et al. (1994); Starzynska, T. et al. (1998); Mulder, W. M. et al. (1997); Starzynska, T. et al. (1992)). The pattern of 5T4 expression in stem cell populations has not previously been identified.

SUMMARY OF THE INVENTION

The present application identifies that the expression of 5T4-oncofoetal antigen is a positive marker of differentiated ES cells and a negative indicator of pluripotency. 5T4 protein and mRNA are not detectable in undifferentiated ES cells but are rapidly upregulated in cells derived from all three germ layers following differentiation. Upregulation of 5T4 glycoprotein expression correlates with loss of pluripotent markers such as OCT-4. Thus, lack of cell-surface 5T4 antigen is a sensitive indicator of undifferentiated ES cell pluripotency, allowing rapid monitoring and optimising of ES cell culture conditions. 5T4 antigen expression on ES cells is unaffected by extended passage, cloning or growth on gelatin-treated plates, allowing differentiation analysis for a wide range of ES cell applications. By contrast, ES cell transcript markers Oct-3/4 or Rex-1 (Rathjen et al. (1999); Niwa et al. (2000); Ben-Sushan et al. (1998)) are unable to confirm homogeneous ES cell integrity since they continue to be expressed in differentiating 5T4-positive monolayer cultures. Upregulation of 5T4 antigen in sub-optimal culture conditions is also observed.

Accordingly, in one aspect of the invention, there is provided a method for detecting the differentiation status of stem cells comprising detecting expression of 5T4 antigen wherein lack of expression of 5T4 indicates undifferentiated stem cells whereas an increased level of expression indicates stem cells which have activated the differentiation pathway. Preferably, said stem cells are mammalian stem cells and, in particular, ES cells.

"Differentiation status" refers to the stage of differentiation. Initially, stem cells are undifferentiated, pluripotent cells which can give rise to cells of one or more differentiated cell types. As they progress from undifferentiated through to fully differentiated, cells lose their pluripotency and express a more restricted set of genes. Accordingly, the method of the first aspect encompasses a method for detecting pluripotent stem cells by detecting a lack of expression of 5T4 antigen.

Expression of 5T4 antigen can be detected through detection of the 5T4 protein or through detection of mRNA transcripts. Techniques for detecting gene and protein expression are familiar to those skilled in the art.

"Expression of 5T4" also extends to activation of the 5T4 promoter in a construct which can be detected through expression of a reporter gene, as described herein.

As demonstrated herein, the level of 5T4 expression correlates with the differentiation status of the stem cells such as ES cells. Thus, an absence or lack of 5T4 expression is no 5T4 expression or a low or negligible level of 5T4 expression and indicates that the stem cells are undifferentiated (or pluripotent) whereas an increased amount of expression compared to this low level indicates the presence of differentiated cells. Suitably the level of 5T4 expression may be determined through comparative studies of stem cells incubated under different conditions. Levels may be expressed as numbers or % of positive cells in a stem cell population when measured by FACS-based techniques or through quantitative analysis methods such as quantitative amplification of mRNAs (e.g. RT-PCR) or quantitative determination of protein expression (e.g. Western Blotting). Suitable methods are described herein.

Detection of differentiation status can be particularly useful in determining optimal cell culture conditions for establishing and maintaining stem cell cultures. For example, and as described herein, cells can be placed in culture conditions and samples of those cells removed and tested for 5T4 expression. 5T4 expression is negatively associated with optimised undifferentiated culture conditions. Continual monitoring of 5T4 expression can allow the manipulation of the culture conditions, using positive and negative 5T4 expression to obtain the require differentiation status.

Advantageously, detection of 5T4 expression on stem cells is a non-destructive method. The cell surface expression of 5T4 allows non-destructive methods for analysis or sorting of viable cell populations. This is in contrast to OCT-4 and other transcription factor markers which require cell permeabilisation for detection and thus destruction of the cell population.

In a preferred embodiment there is provided a method of detecting differentiation status of a population of mammalian stem cells comprising the steps of:
a) taking a sample of cells from said population of mammalian stem cells;
b) incubating said sample with an anti-5T4 antibody under conditions for specific binding of anti-5T4 antibody to 5T4 antigen;
c) detecting binding of said antibody to said antigen and thereby detecting presence of 5T4 on cells in the sample wherein presence of 5T4 is indicative of the presence of differentiated cells in the sample.

Suitably, the method for detecting 5T4 expression is an immunofluorescent technique in which fluorescently labelled anti-5T4 antibody is used and detection is through FACS analysis substantially as described herein. In this embodiment, it is preferred that the anti-5T4 antibody specifically recognises an extracellularly expressed portion of 5T4. The detection of 5T4 antibody or 5T4 tagged antibody by anti-Ig or anti-tag Abs are envisaged.

Suitably, said mammalian stem cells are derived from embryos and include embryonic stem cells (ES cells), embryonic germ cells or embryonal carcinoma cells. Other suitable cells are adult stem cells and include mesenchymal, haematopoeitic, neural and epithelial cells. In one embodiment, said cells are genetically modified stem cells.

Said stem cells are suitably murine, human, primate, porcine, feline or canine, bovine, ovine although any mammalian stem cells may be used.

In another aspect there is provided use of anti-5T4 antibodies in a method for detecting differentiation status of mammalian stem cells.

Suitable anti-5T4 antibodies include those known in the art or any anti-5T4 antibodies that can be raised according to methods known to those skilled in the art. In one embodiment, the anti-5T4 antibody is the 9A7 antibody as described herein. In another embodiment, the antibody is an anti-human 5T4 antibody (mAb 5T4) such as that described in Hole and Stern 1988). Preferably, the anti-5T4 antibody recognises the extracellular domain of the 5T4 antigen to facilitate detection of 5T4 cell surface expression and thus allow non-destructive detection methods (FIG. 4). Methods for labelling antibodies to detect binding are known to those skilled in the art.

Cultured mammalian stem cells can be used in a number of techniques. In some techniques it is desirable to use a population of cells comprising only differentiated or only undifferentiated cells.

Accordingly, in another aspect of the invention, there is provided a method for separating a population of undifferentiated or differentiated mammalian stem cells from a mixture of differentiated and undifferentiated stem cells comprising:
a) binding cells in said mixture of differentiated and undifferentiated stem cells with anti-5T4 antibody,
b) separating cells with bound antibody from cells with no bound antibody; and
c) isolating the cells.

Suitable methods for separating cells include using Ig magnetic beads such as MACS beads or other FACS techniques. It will be appreciated that where a population of undifferentiated stem cells is desired, those cells with no bound antibody may be isolated and selected.

In a preferred embodiment, the cells isolated or separated by said method are viable.

In another embodiment, the antibody is unbound from the cells following separation.

As demonstrated herein, with reference to human germ cell tumour cells (embryonal carcinomas), upregulation of 5T4 antigen is observed in sub-optimal culture conditions. Accordingly, in a further aspect of the invention there is provided a method for testing growth serum for its use in maintaining mammalian cells comprising detecting expression of 5T4.

Suitably, said method comprises the steps of:
a) taking mammalian stem cells in culture;
b) applying test media; and c) assessing 5T4 expression in the absence or presence of said media wherein the presence of 5T4 is an indication that mammalian stem cells are undergoing differentiation.

This method can be utilized for determining optima cell culture conditions for establishing and maintaining stem cells in culture.

Stem cells represent useful culture conditions for detecting effects of a test compound and in particular detecting the ability of a test compound to induce differentiation or cause any toxic effects.

Accordingly, in a further aspect of the invention, there is provided a method for detecting the ability of a test compound to induce mammalian stem cell differentiation comprising the steps of:
a) incubating a mammalian cell culture in the presence or absence of said test compound;
b) detecting 5T4 expression; and
c) comparing the levels of 5T4 expression in cells wherein increased 5T4 expression in those cells incubated in the presence of said test compound indicates differentiation induction by said test compound.

In one embodiment, "5T4 expression" may be detected through detecting 5T4 promoter activity in a construct in which the 5T4 promoter is operably linked to a reporter gene as described below. Suitably the reporter gene may be LacZ for detecting in a beta galactosidase system. A number of other suitable reporter gene systems are familiar to those skilled in the art.

The detection of 5T4 mRNA and protein expression at the beginning of stem cell differentiation suggests that activation of 5T4 transcription may be a key event in the induction of differentiation and developmental pathways.

Thus, the detection of 5T4 expression can be an indication of the induction of differentiation by a known compound. Suitable differentiation-inducing compounds are known to those skilled in the art. Thus, the ability of a test compound to act as an enhancer or inhibitor of the activity of a differentiation-inducing compound can be detected by measuring 5T4 expression.

Accordingly, in another aspect of the invention, there is provided a method for detecting the ability of a test compound to enhance or inhibit the activity of a mammalian stem cell differentiation-inducing compound comprising the steps of:
a) incubating a mammalian cell culture treated with a differentiation-inducing compound in the presence or absence of said test compound;
b) detecting 5T4 expression; and
c) comparing the levels of 5T4 expression in cells wherein increased 5T4 expression in those cells incubated in the presence of said test compound indicates the ability of a test compound to enhance differentiation-induction while decreased 5T4 expression indicates the ability of a test compound to inhibit differentiation-induction.

Transcription of 5T4 may be regulated by interactions at the level of promoter activation from the 5T4 gene promoter region. Activation of the 5T4 promoter may be harnessed to induce expression of genes at the beginning of the stem cell differentiation pathway. Suitable genes of interest which may be expressed under the control of the 5T4 promoter include those which may act as reporter genes, including genes to allow expression of selectable markers or expression of genes conferring resistance to selectable conditions such as neomycin. Other suitable genes include functional genes for which expression at the beginning of differentiation may be desirable such as genes involved in specific differentiation pathways. In addition, it may be desirable to express genes whose products have a toxic effect on a cell. In this way, expression of the gene under control of the 5T4 promoter would induce expression of a toxic product in those cells undergoing differentiation and therefore eradicate differentiating cells from a population.

Expression from the 5T4 promoter can be induced by introducing a vector comprising the 5T4 promoter. Suitably the vector comprising the 5T4 promoter can be a targeting construct for homologous recombination. Methods for homologous recombination are well known to those skilled in the art. Suitable constructs are described, for example, in "Gene Targeting, a practical approach", Ed. A. L. Joyner, $2^{nd}$ Edition, Oxford University Press, 2000.

In another aspect of the invention, there is provided a targeting construct for homologous recombination targeting the 5T4 promoter. Suitably, the targeting construct comprises a region homologous to 5T4, including immune or human 5T4, flanking a gene of interest. In one embodiment, the construct further comprises one or more insertion selectors enabling selection of successfully recombined constructs. In a particularly preferred embodiment, said construct is essentially as shown in FIG. 29.

In another aspect of the invention there is provided a method for detecting differentiation status of a mammalian stem cell comprising:
a) introducing into a stem cell a vector comprising a 5T4 promoter sequence operably linked to a nucleic acid encoding a reporter gene; and
b) detecting an increase in expression of the reporter gene as an indication of differentiation.

In a further aspect of the invention, there is provided a method of modifying a mammalian stem cell comprising introducing a nucleic acid sequence into a mammalian cell such that said nucleic acid sequence is placed under the control of the 5T4 promoter sequence.

In one embodiment, genes may be expressed under the control of the 5T4 promoter region through introduction of vectors comprising the 5T4 promoter operably linked to the nucleic acid encoding the gene of interest. In another embodiment, the genes introduced may be combined or "knocked in" to the genome of the stem cell through methods such as homologous recombination. Other suitable methods will be familiar to those skilled in the art.

In another aspect of the invention, there is provided a method of modulating stem cell differentiation comprising modifying the expression of 5T4 or its functional activity.

Cells which have been sorted according to their expression of 5T4 can be used in a number of stem cell applications. Accordingly, in another aspect of the invention, there is provided a use of a stem cell selected according to a method of any of the previous aspects of the invention in a method of treating an individual. Applications of stem cells include therapeutic applications which are reviewed for example in Nature Insight Review, Vol 414, November 2001. In particular stem cells may be targets for gene therapy and may be genetically modified prior to their use in therapeutic applications as described, for example, in Rideout et al. Cell, 109(1): 17-27, 2002; Wu et al. Gene Ther 9(4), 245-255, February 2002; Lebkowski et al. Cancer J. 7 Suppl 2; S83-93; November-December 2001.

In another aspect, the methods of the invention may be applicable to confirming the absence of 5T4-negative i.e. undifferentiated cells from a population prior to introducing said cells into an individual.

In a fiercer aspect of the invention there is provided an isolated antibody recognising the membrane proximal extracellular domain of murine 5T4. Suitably, said antibody is an isolated rat monoclonal anti-5T4 antibody, 9A7 or a human 5T4 specific antibody such as MAb 5T4 described by Hole and Stern 1988 (FIG. 4).

Despite human and mouse 5T4 sharing 81% identity in a conserved domain structure, the monoclonal antibody recognizing human 5T4, sometimes referred to as MAb5T4, does not cross react with m5T4 (Shaw et al. (2002)). The Mab5T4 antibody recognizes a conformational epitope dependent upon glycosylation and the correct formation of intramolecular disulphide bonds (Shaw et al. (2002); Hole et al. (1990)).

Other aspects of the present invention are presented in the accompanying claims and in the following description and discussion. These aspects are presented under separate section headings. However, it is to be understood that the teachings under each section heading are not necessarily limited to that particular section heading.

DETAILED DESCRIPTION OF THE INVENTION

Unless defined otherwise, all technical and scientific terms used herein have the same meaning as commonly understood by one of ordinary skill in the art (e.g., in cell culture, molecular genetics, nucleic acid chemistry, hybridisation techniques and biochemistry). Standard techniques are used for molecular, genetic and biochemical methods. See, generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) $4^{th}$ Ed, John Wiley & Sons, Inc.; as well as Guthrie et al., Guide to Yeast Genetics and Molecular Biology, Methods in Enzymology, Vol. 194, Academic Press, Inc., (1991), PCR Protocols: A Guide to Methods and Applications (Innis, et al. 1990. Academic Press, San Diego, Calif.), McPherson et al., PCR Volume 1, Oxford University Press, (1991), Culture of Animal Cells: A Manual of Basic Technique, 2nd Ed. (R. L Freshney. 1987. Liss, Inc. New York, N.Y.), and Gene Transfer and Expression Protocols, pp. 109-128, ed E. J. Murray, The Humana Press Inc., Clifton, N.J.). These documents are incorporated herein by reference.

5T4 antigen is the polypeptide known as 5T4 and characterised, for example, in WO89/07947. "5T4" may be human 5T4 as characterised by Myers et al ibid., the sequence of which appears in GenBank at accession no. Z29083. A sequence for mouse or murine 5T4 (m5T4) appears in GenBank at Accession no. AJ012160. The organisation of the mouse and human 5T4 genes is described, for example, by King et al. Biochim Biophys Acta 1999; 1445 (3); 257-70. Canine and feline 5T4 sequences are described, for example, in PCT/GB01/05004 (WO 02/38612)

Sequence analysis of the human 5T4 cDNA identified the antigen as a member of the leucine-rich repeat (LRR) family of proteins (Myers, K. A. et al. (1994)). The protein contains a short cytoplasmic tail of 44 amino acids and an extracellular domain consisting of two leucine-rich repeat (LRR) regions with associated cysteine containing flanking regions and separated by a hydrophilic domain. All of the seven consensus NxS/T N-glycosylation sites in the extracellular domain are glycosylated with a combination of complex glycans, including two high mannose chains and five sialylated, bi- to tetra-antennary complex chains with minor quantities of core fucosylation (Shaw, D. M. et al. (2002)).

LRR proteins are a diverse family of approximately 60 members, which have in common a repeating structure of aXXaXaXXN/C/T, where a is an aliphatic residue such as leucine and X is any amino acid (Kobe et al. (1994)). The tertiary structure of porcine ribonuclease inhibitor, which is comprised entirely of LRRs, has been solved by X-ray crystallography (Kobe et al. (1994)). Ribonuclease inhibitor folds into a horseshoe-like structure of repeating units of α-helix and β-pleated sheets, this resolved structure has formed the basis of structural models for other family members (Kajava et al. (1995); Janosi et al. (1999)). However, the precise structure may vary due to differences in the lengths of the LRRs and the presence of other functional domains. Despite no common function having been ascribed, many are involved in protein-protein interactions and overall it is likely that the LRR domains provide a scaffold for a variety of functions (Kobe et al. (1994), Kobe et al. (1995)).

5T4 antigen is expressed on microvillus projections of cells and when the human 5T4 cDNA is constitutively overexpressed in certain fibroblasts or epithelial cells, there are alterations in motility and morphology which are consistent with a role in both tumour and, trophoblast invasion (Carsberg et al. (1995); Carsberg et al. (1996)).

Sequence comparisons between the human and mouse 5T4 cDNAs (King et al. 1999)) indicate the highly conserved structure of 5T4 molecules between species. These molecules share 81% amino acid identity, with the cytoplasmic and transmembrane domains being completely conserved. Of the seven N-linked glycosylation sites in the human molecule six are conserved in the mouse. The most N-terminal site (N81) is absent, but au additional site (N334) in the C-terminal flanking region is present predicting a similar level of glycosylation to the human molecules. The murine protein contains an additional six amino acids adjacent to the glycosylation site in the hydrophilic domain, which is a direct repeat of the preceding six amino acids. The expression of 5T4 in trophoblasts suggests it is present at a stage of development common to all mammals. This makes it likely that 5T4 is highly conserved throughout mammals.

As used herein, "differentiated cells" with particular reference to stem cells means cells which retain their characteristic pluripotency or multipotency i.e. their ability to give rise to all cell types or more than one differentiated cell type. The terms "differentiated" or "differentiation status" when referring to a cell means cells that have begun to or have partially or completely developed into cells with a defined phenotype. The characteristic phenotypes of particular differentiated cell types are dependent on the particular cell type and are recognised by those skilled in the art.

As used herein, the term "polypeptide" refers to a polymer in which the monomers are amino acids and are joined together through peptide or disulphide bonds. "Polypeptide" refers to a full-length naturally-occurring amino acid chain or a fragment thereof, such as a selected region of the polypeptide that is of interest in a binding interaction, or a synthetic amino acid chain, or a combination thereof. "Fragment thereof" thus refers to an amino acid sequence that is a portion of a full-length polypeptide, between about 8 and about 500 amino acids in length, preferably about 8 to about 300, more preferably about 8 to about 200 amino acids, and even more preferably about 10 to about 50 or 100 amino acids in length. Additionally, amino acids other than naturally-occurring amino acids, for example β-alanine, phenyl glycine and homoarginine, may be included. Commonly-encountered amino acids which are not gene-encoded may also be used in the present invention.

The expression "5T4 antigen" encompasses fragments thereof, and preferably those fragments having distinct epitopes, and variants thereof comprising amino acid insertions, deletions or substitutions which retain the antigenicity of 5T4. Suitably, the term 5T4 antigen, includes peptides and other fragments of 5T4 which retain at least one common antigenic determinant of 5T4.

"Common antigenic determinant" means that the derivative in question has at least one antigenic fiction of 5T4. Antigenic functions includes possession of an epitope or antigenic site that is capable of cross-reacting with antibodies raised against a naturally occurring or denatured 5T4 polypeptide or fragment thereof, or the ability to bind HLA molecules and induce a 5T4-specific immune response.

Thus 5T4 antigen as referred to herein includes amino acid mutants, glycosylation variants and other covalent derivatives of 5T4 which retain the physiological and/or physical properties of 5T4. Exemplary derivatives include molecules wherein the protein of the invention is covalently modified by substitution, chemical, enzymatic, or other appropriate means with a moiety other than a naturally occurring amino acid. Such a moiety may be a detectable moiety such as an enzyme or a radioisotope. Further included are naturally occurring variants of 5T4 found with a particular species, preferably a mammal. Such a variant may be encoded by a related gene of the same gene family, by an allelic variant of a particular gene, or represent an alternative splicing variant of the 5T4 gene.

Derivatives which retain common antigenic determinants can be fragments of 5T4. Fragments of 5T4 comprise individual domains thereof, as well as smaller polypeptides derived from the domains. Preferably, smaller polypeptides derived from 5T4 according to the invention define a single epitope which is characteristic of 5T4. Fragments may in theory be almost any size, as long as they retain one characteristic of 5T4. Preferably, fragments will be between 5 and 400 amino acids in length. Longer fragments are regarded as truncations of the full-length 5T4 and generally encompassed by the term "5T4". Advantageously, fragments are relatively small peptides of the order of 5 to 25 amino acids in length. Preferred are peptides about 9 amino acids in length.

Derivatives of 5T4 also comprise mutants thereof; which may contain amino acid deletions, additions or substitutions, subject to the requirement to maintain at least one feature characteristic of 5T4. Thus, conservative amino acid substitutions may be made substantially without altering the nature of 5T4, as may truncations from the 5' or 3' ends. Deletions and substitutions may moreover be made to the fragments of 5T4 comprised by the invention. 5T4 mutants may be produced from a DNA encoding 5T4 which has been subjected to in vitro mutagenesis resulting e.g. in an addition, exchange and/or deletion of one or more amino acids. For example, substitutional, deletional or insertional variants of 5T4 can be prepared by recombinant methods and screened for immunocrossreactivity with the native forms of 5T4.

The fragments, mutants and other derivatives of 5T4 preferably retain substantial homology with 5T4. As used herein, "homology" means that the two entities share sufficient characteristics for the skilled person to determine that they are similar in origin and function.

"Substantial homology", where homology indicates sequence identity, means more than 40% sequence identity, preferably more than 45% sequence identity and most preferably a sequence identity of 50% or more, as judged by direct sequence alignment and comparison.

Sequence homology (or identity) may moreover be determined using any suitable homology algorithm, using for example default parameters. Advantageously, the BLAST algorithm is employed, with parameters set to default values. The BLAST algorithm is described in detail on the worldwide web at ncbi.nih.gov/BLAST/blasthelp.html, which is incorporated herein by reference.

As used herein, the term "antibody" refers to a polypeptide, at least a portion of which is encoded by at least one immunoglobulin gene, or fragment thereof, and that can bind specifically to a desired target molecule. The term includes naturally-occurring forms, as well as fragments and derivatives.

"Specific binding" refers to the ability of two molecular species concurrently present in a heterogeneous (inhomogeneous) sample to bind to one another in preference to binding to other molecular species in the sample. Typically, a specific binding interaction will discriminate over adventitious binding interactions in the reaction by at least twofold, more typically by at least 10-fold, often at least 100-fold; when used to detect analyte, specific binding is sufficiently discriminatory when determinative of the presence of the analyte in a heterogeneous (inhomogeneous) sample.

As used herein, a "vector" may be any agent capable of delivering or maintaining nucleic acid in a host cell, and includes viral vectors, plasmids, naked nucleic acids, nucleic acids complexed with polypeptide or other molecules and nucleic acids immobilised onto solid phase particles.

A "nucleic acid", as referred to herein, may be DNA or RNA, naturally-occurring or synthetic, or any combination thereof. Nucleic acids encoding 5T4 antigen may be constructed in such a way that it may be translated by the machinery of the cells of a host organisms. Thus, natural nucleic acids may be modified, for example to increase the stability thereof. DNA and/or RNA, but especially RNA, may be modified in order to improve nuclease resistance. For example, known modifications for ribonucleotides include 2'-O-methyl, 2'-fluoro, 2'-$NH_2$, and 2'-O-allyl. Modified nucleic acids may comprise chemical modifications which have been made in order to increase the in vivo stability of the nucleic acid, enhance or mediate the delivery thereof, or reduce the clearance rate from the body. Examples of such modifications include chemical substitutions at the ribose and/or phosphate and/or base positions of a given RNA sequence. See, for example, WO 92/03568; U.S. Pat. No. 5,118,672; Hobbs et al., (1973) Biochemistry 12:5138; Guschlbauer et al., (1977) Nucleic Acids Res. 4:1933; Schibaharu et al., (1987) Nucleic Acids Res. 15:4403; Pieken et al., (1991) Science 253:314, each of which is specifically incorporated herein by reference.

Methods of Detecting 5T4 Expression

The term "expression" refers to the transcription of a gene's DNA template to produce the corresponding mRNA and translation of this mRNA to produce the corresponding gene product (i.e., a peptide, polypeptide, or protein). 5T4 antigen is "expressed" in accordance with the present invention by being produced in the cells as a result of translation, and optionally transcription, of the nucleic acid encoding 5T4. Thus, 5T4 is produced in situ in the cell. Since 5T4 is a transmembrane protein, the extracellular portion thereof is displayed on the surface of the cell in which it is produced.

a) At the RNA Level

Expression levels can be assessed by measuring gene transcription. This is preferably carried out by measuring the rate and/or amount of specific mRNA production in the cell. RNA may be extracted from cells using RNA extraction techniques including, for example, using acid phenol/quanidine isothiocyanate action (RNAzol B; Biogenesis), or RNeasy RNA preparation kits (Qiagen). Typical assay format utilising ribonucleic acid hybridisation include nuclear run-on assays, RT-PCR and RNase protection assays (Melton et al., Nuc. Acids Res. 12:7035). Methods for detection which can be employed include radioactive labels, enzyme labels, chemiluminescent labels, fluorescent labels and other suitable labels.

Typically, RT-PCR is used to amplify RNA targets. In this process, the reverse transcriptase enzyme is used to convert RNA to complementary DNA (cDNA) which can then be amplified to facilitate detection.

Many DNA amplification methods are known, most of which rely on an enzymatic chain reaction (such as a polymerase chain reaction, a ligase chain reaction, or a self-sustained sequence replication) or from the replication of all or part of the vector into which it has been cloned.

Many target and signal amplification methods have been described in the literature, for example, general reviews of these methods in Landegren, U., et al., Science 242:229-237 (1988) and Lewis, R., Genetic Engineering News 10:1, 54-55 (1990).

PCR is a nucleic acid amplification method described inter alia in U.S. Pat. Nos. 4,683,195 and 4,683,202. PCR can be used to amplify any known nucleic acid in a diagnostic context (Mok et al., (1994), Gynaecologic Oncology, 52: 247-252).

A number of alternative amplification technologies including rolling circle amplification (Lizardi et al., (1998) Nat Genet 19:225) are known to those skilled in the art.

A primer may be used to allow specific amplification of 5T4 mRNA. A probe is e.g. a single-stranded DNA or RNA that has a sequence of nucleotides that includes between 10 and 50, preferably between 15 and 30 and most preferably at least about 20 contiguous bases that are the same as (or the complement of) an equivalent or greater number of contiguous bases of the mRNA of interest.

Primers suitable for use in various amplification techniques can be prepared according to methods known in the art.

Once the nucleic acid has been amplified, a number of techniques are available for the quantification of DNA and thus quantification of the RNA transcripts present. Methods for detection which can be employed include radioactive labels, enzyme labels, chemiluminescent labels, fluorescent labels and other suitable labels.

Probes may be used to detect the presence of their corresponding sequences through hybridisation reactions e.g. in blotting techniques such as northern or southern blotting. The presence of 5T4 nucleic acid sequences may be detected by hybridisation with specific 5T4 probes under stringent conditions.

The nucleic acid sequences selected as probes should be of sufficient length and sufficiently unambiguous so that false positive results are minimised. The nucleotide sequences are usually based on conserved or highly homologous nucleotide sequences or regions of 5T4.

Either the full-length cDNA for 5T4 or fragments thereof can be used as probes. Preferably, nucleic acid probes are labeled with suitable label means for ready detection upon hybridisation. For example, a suitable label means is a radiolabel. The preferred method of labeling a DNA fragment is by incorporating $\alpha^{32}P$ dATP with the Klenow fragment of DNA polymerase in a random priming reaction, as is well known in the art. Oligonucleotides are usually end-labeled with $\gamma^{32}P$-labelled ATP and polynucleotide kinase. However, other methods (e.g. non-radioactive) may also be used to label the fragment or oligonucleotide, including e.g. enzyme labelling, fluorescent labelling with suitable fluorophores and biotinylation.

Stringency of hybridisation refers to conditions under which polynucleic acid hybrids are stable. Such conditions are evident to those of ordinary skill in the field. As known to those of skill in the art, the stability of hybrids is reflected in the melting temperature (Tm) of the hybrid which decreases approximately 1 to 1.5° C. with every 1% decrease in sequence homology. In general the stability of a hybrid is a function of sodium ion concentration and temperature. Typically, the hybridisation reaction is performed under conditions of higher stringency, followed by washes of varying stringency.

As used herein, high stringency refers to conditions that permit hybridisation of only those nucleic acid sequences that form stable hybrids in 1 M Na+ at 65-68° C. High stringency conditions can be provided, for example, by hybridisation in an aqueous solution containing 6×SSC, 5× Denhardt's, 1% SDS (sodium dodecyl sulphate), 0.1 Na+ pyrophosphate and 0.1 mg/ml denatured salmon sperm DNA as non specific competitor. Following hybridisation, high stringency washing may be done in several steps, with a final wash (about 30 min) at the hybridisation temperature in 0.2-0.1×SSC, 0.1% SDS.

Moderate stringency refers to conditions equivalent to hybridisation in the above-described solution but at about 60-62° C. In that case the final wash is performed at the hybridisation temperature in 1×SSC, 0.1% SDS.

Low stringency refers to conditions equivalent to hybridisation in the above-described solution at about 50-52° C. In that case, the final wash is performed at the hybridisation temperature in 2×SSC, 0.1% SDS.

It is understood that these conditions may be adapted and duplicated using a variety of buffers, e.g. formamide-based buffers, and temperatures. Denhardt's solution and SSC are well known to those of skill in the art as are other suitable hybridisation buffers (see, e.g. Sambrook, et al., eds. (1989) Molecular Cloning: A Laboratory Manual, Cold Spring Harbor Laboratory Press, New York or Ausubel, et al., eds. (1990) Current Protocols in Molecular Biology, John Wiley & Sons, Inc.). Optimal hybridisation conditions have to be determined empirically, as the length and the GC content of the probe also play a role.

In the context of the present invention, detection of 5T4 expression gives an indication of differentiation status of mammalian ES cells where an increase in 5T4 mRNA expression or stability or both is an indication of induction of differentiation whereas the absence, or expression at low or negligible levels is an indication of undifferentiated status.

b) At the Protein Level

Gene expression may also be detected at the protein level by measuring amounts of 5T4 antigen polypeptide. A variety of protocols for detecting and measuring the expression of the amino acid sequences are known in the art. Examples include enzyme-linked immunosorbent assay (ELISA), radioimmunoassay (RIA) and fluorescent activated cell sorting (FACS). These and other assays are described, among other places, in Hampton R et al (1990, Serological Methods, A Laboratory Manual, APS Press, St Paul Minn.) and Maddox D E et al (1983, J Exp Med 15 8:121 1). A suitable FACS-based method is described in the Examples section herein.

Detection of protein expression may be achieved by using molecules which bind to the 5T4 antigen polypeptide. Suitable molecules/agents which bind either directly or indirectly to 5T4 in order to detect the presence of the protein include naturally occurring molecules such as peptides and proteins, for example antibodies, or they may be synthetic molecules.

Other naturally occurring molecules which bind 5T4 include specific 5T4 ligands. For example, a number of intracellular partners for 5T4 have been identified and are described in Awan et al. (Biochem Biophys Res Comm (2002); 290 (3); 1030-1036).

Anti-5T4 antibodies are antibodies that specifically bind to 5T4 antigen. They may be polyclonal or monoclonal. If polyclonal antibodies are desired, a selected mammal (e.g., mouse, rabbit, goat, horse, etc.) is immunised with an immunogenic polypeptide bearing a 5T4 epitope such as 5T4-Fc. Serum from the immunised animal is collected and treated according to known procedures. If serum containing polyclonal antibodies to a 5T4 epitope contains antibodies to other antigens, the polyclonal antibodies can be purified by immunoaffinity chromatography. Techniques for producing and processing polyclonal antisera are known in the art. Such antibodies may also be made using polypeptides or fragments thereof haptenised to another polypeptide for use as immunogens in animals or humans.

An immune response may also be elicited by immunisation with a vector comprising a 5T4-expressing nucleic acid.

The vector employed for immunisation may be any vector, viral or non-viral. The 5T4 antigen used, whether full length 5T4 or peptides thereof, may be modified and may be homologous (i.e. derived from the same species as the subject stem cells) or heterologous in origin.

Monoclonal antibodies directed against 5T4 epitopes can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against 5T4 epitopes can be screened for various properties; i.e., for isotype and epitope affinity.

An alternative technique involves screening phage display libraries where, for example the phages express scFv fragments on the surface of their coat with a large variety of complementarity determining regions (CDRs). This technique is well known in the art.

For the purposes of this invention, the term "antibody", unless specified to the contrary, includes fragments of whole antibodies which retain their binding activity for a target antigen. Such fragments include Fv, F(ab') and F(ab')$_2$ fragments, as well as single chain antibodies (scFv) and domain antibodies (dAbs) which are described, for example, in U.S. Pat. No. 6,248,516, U.S. Pat. No. 6,291,158, U.S. Pat. No. 6,172,197 and EP 0,368,684.

Standard laboratory techniques involving antibodies can be used to detect levels of 5T4 in stem cells. One such technique is immunoblotting, an example of a suitable protocol for which is detailed below:

Aliquots of total protein exacts from stem cells (40 μg), are run on SDS-PAGE and electroblotted overnight at 4° C. onto nitrocellulose membrane. Immunodetection involves antibodies specific for 5T4, appropriate secondary antibodies (goat, anti-rabbit or goat-anti-mouse: Bio-Rad, CA, USA) conjugated to horseradish peroxidase, and the enhanced ECL chemilumlinescence detection system (Amersham, UK).

Methods for Selecting Cells by 5T4 Expression

A variety of selection procedures may be applied for the isolation of cells expressing 5T4 (positive selection) or undifferentiated cells lacking 5T4 expression (negative expression). These include Fluorescence Activated Cell Sorting (FACS), cell separation using magnetic particles, panning, antigen chromatography methods and other cell separation techniques such as use of polystyrene beads.

Separating cells using magnetic capture may be accomplished by conjugating a molecule which binds to 5T4 antigen to magnetic particles or beads. For example, the 5T4 binding agent may be conjugated to superparamagnetic iron-dextran particles or beads as supplied by Miltenyi Biotec GmbH. These conjugated particles or beads are then mixed with a cell population which may express 5T4. If a particular cell expresses 5T4, it will become complexed with the magnetic beads by virtue of this interaction. A magnetic field is then applied to the suspension which immobilises the magnetic particles, and retains any cells which are associated with them via the covalently linked antigen. Unbound cells which do not become linked to the beads can be washed away or collected separately, leaving a population of cells which is isolated by virtue of the expression of 5T4. Reagents and kits are available from various sources for performing such isolations, and include Dynal Beads (Dynal A S; on the worldwide web at dynal.no), MACS-Magnetic Cell Sorting (Miltenyi Biotec GmbH; on the worldwide web at mitenylbiotec.com), CliniMACS (AmCell; on the worldwide web at amcell.com) as well as Biomag, Amerlex-M beads and others.

Fluorescence Activated Cell Sorting (FACS) can be used to isolate cells on the basis of their differing surface molecules, for example surface-displayed 5T4. Cells in the sample or population to be sorted are stained with specific fluorescent reagents which bind to 5T4. These reagents would be the 5T4 binding agent linked (either directly or indirectly) to fluorescent markers such as fluorescein, Texas Red, malachite green, green fluorescent protein (GFP), or any other fluorophore known to those skilled in the art. The cell population is then introduced into the vibrating flow chamber of the FACS machine. The cell stream passing out of the chamber is encased in a sheath of buffer fluid such as PBS (Phosphate Buffered Saline). The stream is illuminated by laser light and each cell is measured for fluorescence, indicating binding of the fluorescent-labelled antigen. The vibration in the cell stream causes it to break up into droplets, which carry a small electrical charge. These droplets can be steered by electric deflection plates under computer control to collect different cell populations according to their affinity for the fluorescent labelled binding agent. In this manner, cell populations which express 5T4 can be easily separated from those cells which do not express 5T4. FACS machines and reagents for use in FACS are widely available from sources worldwide such as Becton-Dickinson, or from service providers such as Arizona Research Laboratories (on the worldwide web at arl.arizona.edu/facs/).

Another method which can be used to separate populations of cells according to cell surface expression of 5T4 is affinity chromatography. In this method, a suitable resin (for example CL-600 Sepharose, Pharmaca Inc.) is covalently liked to the appropriate 5T4 binding agent. This resin is packed into a column, and the mixed population of cells is passed over the column. After a suitable period of incubation (for example 20 minutes), unbound cells are washed away using (for example) PBS buffer. This leaves only that subset of cells expressing 5T4 and these cells are then eluted from the column using (for example) an excess of the 5T4, or by enzymatically or chemically cleaving the bound reagent from the resin thereby releasing that population of cells which exhibited 5T4 expression.

Expression from the 5T4 Promoter

The term "promoter" or "promoter region" refers to a nucleic acid sequence, usually found upstream (5') to a coding sequence, that is capable of directing transcription of a nucleic acid sequence into mRNA. The promoter or promoter region typically provides a recognition site for RNA polymerase and the other factors necessary for proper initiation of transcription. As contemplated herein, a promoter or promoter region includes variations of promoters derived by inserting or deleting regulatory regions, subjecting the promoter to random or site-directed mutagenesis, etc. The activity or strength of a promoter may be measured in terms of the amounts of RNA it produces, or the amount of protein accumulation in a cell or tissue, relative to a promoter whose transcriptional activity has been previously assessed.

A "nucleic acid encoding the promoter sequence of 5T4" means a nucleic acid sequence which is capable of directing endogenous transcription of 5T4 gene expression. The term moreover includes those polynucleotides capable of hybridising, under stringent hybridisation conditions, to the naturally occurring nucleic acids identified above, or the complement thereof.

The phrase "operably linked" refers to the functional spatial arrangement of two or more nucleic acid regions or nucleic acid sequences. For example, a promoter region may be positioned relative to a nucleic acid sequence such that transcription of a nucleic acid sequence is directed by the promoter region. Thus, a promoter region is "operably linked" to the nucleic acid sequence.

A "porter gene" is a gene which is incorporated into an expression vector and placed under the same controls as a gene of interest to express an easily measurable phenotype.

Methods for Detecting Transcription from a Promoter Sequence

Transcription from the 5T4 promoter sequence can be detected using a nucleic acid construct comprising the 5T4 promoter sequence operably linked to a reporter gene. A "reporter gene" is a gene which is incorporated into an expression vector and placed under the same controls as a gene of interest to express an easily measurable phenotype. A number of suitable reporter genes are known whose expression may be detectable by histochemical staining, liquid scintillation, spectrophotometry or luminometry. Many reporters have been adapted for a broad range of assays, including colorimetric, fluorescent, bioluminescent, chemiluminescent, ELISA, and/or in situ staining. Suitable reporter systems are based on the expression of enzymes such as chloramphenicol acetyltransferase (CAT), beta-galaosidase (beta-gal), beta-glucuronidase, alkaline phosphatase and luciferase. More recently, a number of reporter systems have been developed which are based on using Green fluorescent proteins (GFP) or various derivatives or mutant forms including EGFP. Reporter genes and detection systems are reviewed by Sussman in The Scientist 15 [15]:25, Jul. 23, 2001 which is incorporated by reference.

Vectors for Gene Delivery or Expression.

To generate cells expressing an exogenous gene or 5T4-expressing cells, polypeptides such as 5T4 polypeptides can be delivered by viral or non-viral techniques. Delivery of 5T4 antigen for immunisation purposes can also be through viral or non-viral techniques.

Non-viral delivery systems include but are not limited to DNA transfection methods. Here, transfection includes a process using a non-viral vector to deliver a 5T4 gene to a target mammalian cell. The post-translational modification in relation to phosphorylation or glycosylation may be varied by expression of 5T4 in different target cells.

Typical transfection methods include electroporation, nucleic acid biolistics, lipid-mediated transfection, compacted nucleic acid-mediated transfection, liposomes, immunoliposomes, lipofectin, cationic agent-mediated, cationic facial amphiphiles (CFAs) (Nature Biotechnology 1996 14; 556), multivalent cations such as spermine, cationic lipids or polylysine, 1,2,-bis(oleoyloxy)-3-(trimethylammonio)propane (DOTAP)-cholesterol complexes (Wolff and Trubetskoy 1998 Nature Biotechnology 16: 421) and combinations thereof.

Viral delivery systems include but are not limited to adenovirus vectors, adeno-associated viral (AAV) vectors, herpes viral vectors, retroviral vectors, lentiviral vectors or baculoviral vectors, venezuelan equine encephalitis virus (VEE), pox-viruses such as: canarypox virus (Taylor et al 1995 Vaccine 13:539-549), entomopox virus (Li Y et al 1998 XII$^{th}$ International Poxvirus Symposium p144. Abstract), penguine pox (Standard et al. J Gen Virol. 1998 79:1637-46) alphavirus, and alphavirus based DNA vectors.

A detailed list of retroviruses may be found in Coffin et al ("Retroviruses" 1997 Cold Spring Harbour Laboratory Press Eds: J M Coffin, S M Hughes, H E Varmus pp 758-763).

Lentiviruses can be divided into primate and non-primate groups. Examples of primate lentiviruses include but are not limited to: the human immunodeficiency virus (HIV), the causative agent of human auto-immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

A distinction between the lentivirus family and other types of retroviruses is that lentiviruses have the capability to infect both dividing and non-dividing cells (Lewis et al 1992 EMBO. J 11: 3053-3058; Lewis and Emerman 1994 J. Virol. 68: 510-516). In contrast, other retroviruses—such as MLV—are unable to infect non-dividing cells such as those that make up, for example, muscle, brain, lung and liver tissue.

The vector encoding 5T4 may be configured as a split-intron vector. A split intron vector is described in PCT patent applications WO 99/15683 and WO 99/15684.

If the features of adenoviruses are combined with the genetic stability of retroviruses/lentiviruses then essentially the adenovirus can be used to transduce target cells to become transient retroviral producer cells that could stably infect neighbouring cells. Such retroviral producer cells engineered to express 5T4 antigen can be implanted in organisms such as animals or humans for use in the treatment of angiogenesis and/or cancer.

Pox viruses are engineered for recombinant gene expression and for the use as recombinant live vaccines. This entails the use of recombinant techniques to introduce nucleic acids encoding foreign antigens into the genome of the pox virus. If the nucleic acid is integrated at a site in the viral DNA which is non-essential for the life cycle of the virus, it is possible for the newly produced recombinant pox virus to be infectious, that is to say to infect foreign cells and thus to express the integrated DNA sequence. The recombinant pox virus prepared in this way can be used as live vaccines for the prophylaxis and/or treatment of pathologic and infectious disease. Such live vaccines can also be used to raise antibodies against 5T4. Suitable vectors derived from Vaccinia Western Reserve are described in the Examples section herein.

Expression of 5T4 in recombinant pox viruses, such as vaccinia viruses, requires the ligation of vaccinia promoters to the nucleic acid encoding 5T4. Plasmid vectors (also called insertion vectors), have been constructed to insert nucleic acids into vaccinia virus through homologous recombination between the viral sequences flanking the nucleic acid in a donor plasmid and homologous sequence present in the parental virus (Mackett et al 1982 PNAS 79: 7415-7419). One type of insertion vector is composed of: (a) a vaccinia virus promoter including the transcriptional initiation site; (b) several unique restriction endonuclease cloning sites located downstream from the transcriptional start site for insertion of nucleic acid; (c) nonessential vaccinia virus sequences (such as the Thymidine Kinase (TX) gene) flanking the promoter and cloning sites which direct insertion of the nucleic acid into the homologous nonessential region of the virus genome; and (d) a bacterial origin of replication and antibiotic resistance marker for replication and selection in *E. Coli*. Examples of such vectors are described by Mackett (Mackett et al 1984, J. Virol. 49: 857-864).

The isolated plasmid containing the nucleic acid to be inserted is transfected into a cell culture, e.g., chick embryo fibroblasts, along with the parental virus, e.g., poxvirus. Recombination between homologous pox DNA in the plasmid and the viral genome respectively results in a recombinant poxvirus modified by the presence of the promoter-gene construct in its genome, at a site which does not affect virus viability.

As noted above, the nucleic acid is inserted into a region (insertion region) in the virus which does not affect virus viability of the resultant recombinant virus. Such regions can be readily identified in a virus by, for example, randomly testing segments of virus DNA for regions that allow recombinant formation without seriously affecting virus viability of the recombinant. One region that can readily be used and is present in many viruses is the thymidine kinase (TK) gene. For example, the TK gene has been found in all pox virus genomes examined [leporipoxvirus: Upton, et al J. Virology 60:920 (1986) (shope fibroma virus); capripoxvirus: Gershon, et al J. Gen. Virol. 70:525 (1989) (Kenya sheep-1); orthopoxvirus: Weir, et al J. Virol 46:530 (1983) (vaccinia); Esposito, et al Virology 135:561 (1984) (monkeypox and variola virus); Hruby, et al *PNAS,* 80:3411 (1983) (vaccinia); Kilpatrick, et al Virology 143:399 (1985) (Yaba monkey tumour virus); avipoxvirus: Binns, et al J. Gen. Virol 69:1275 (1988) (fowlpox); Boyle, et al Virology 156:355 (1987) (fowlpox); Schnitzlein, et al J. Virological Method, 20:341 (1988) (fowlpox, quailpox); entomopox (Lytvyn, et al J. Gen. Virol 73:3235-3240 (1992)].

In vaccinia, in addition to the TK region, other insertion regions include, for example, HindIII M.

In fowlpox, in addition to the TK region, other insertion regions include, for example, BamHI J [Jenkins, et al AIDS Research and Human Retroviruses 7:991-998 (1991)] the EcoRI-HindIII fragment, BamHI fragment, EcoRV-HindIII fragment, BamHI fragment and the HindIII fragment set forth in EPO Application No. 0 308 220 A1. [Calvert, et al J. of Virol 67:3069-3076 (1993); Taylor, et al Vaccine 6:497-503 (1988); Spehner, et al (1990) and Boursnell, et al J. of Gen Virol 71:621-628 (1990)].

In swinepox preferred insertion sites include the thymidine kinase gene region.

A promoter can readily be selected depending on the host and the target cell type. For example in poxviruses, pox viral promoters should be used, such as the vaccinia 7.5K, or 40K or fowlpox C1. Artificial constructs containing appropriate pox sequences can also be used. Enhancer elements can also be used in combination to increase the level of expression. Furthermore, the use of inducible promoters, which are also well known in the art, are preferred in some embodiments.

Foreign gene expression can be detected by enzymatic or immunological assays (for example, immuno-precipitation, radioimmunoassay, or immunoblotting). Naturally occurring membrane glycoproteins produced from recombinant vaccinia infected cells are glycosylated and may be transported to the cell surface. High expressing levels can be obtained by using strong promoters.

Stem Cells

Stem cells are undifferentiated, pluripotent, primitive cells with the ability both to multiply and differentiate into specific kinds of cells. Mammalian stem cells can also be essentially totipotent (e.g make chimeric mice) as with cell lines derived from mammalian embryos, such as ES, EG or EC cells, or can be multipotent, typically derived from adults. Adult-derived stem cells include neural stem cells, mesenchymal stem cells, hematopoeitic stem cells and epithelial stem cells. Stem cell cultures may be genetically modified after isolation and prior to their differentiation. They could also be modified before generation though derivation from a suitably genetically modified animal.

Mammalian stem cells may be derived from any mammalian species and thus may be murine, human or other primate (e.g. chimpanzee, cynomolgus monkey, baboon, other Old World monkey), porcine, canine, equine, feline etc.

Embryonic stem (ES) cells are stem cells derived from the pluripotent inner cell mass (ICM)/epiblast cells of the pre-implantation, blastocyst-stage embryo. Outgrowth cultures of blastocysts give rise to different types of colonies of cells, some of which have an undifferentiated phenotype. If these undifferentiated cells are sub-cultured onto feeder layers they can be expanded to form established ES cell lines that seem immortal. These pluripotent stem cells can differentiate in vitro into a wide variety of cell types representative the three primary germ layers in the embryo. Methods for deriving ES cells are known for example from Evans et al. 1981; Nature; 29; 154-156.

Embryonic germ (EG) cell lines are derived from primordial germ cells. Methods for the isolation and culture of these cells are descend, for example, by McLaren et al. Reprod. Fertil. Dev 2001; 13 (7-8):661-4. Other types of these cells include embryonal carcinoma cells (EC) (as reviewed, for example, in Donovan and Gearhart, Nature 2001; 414 (6859): 92-97).

Other types of stem cells include cells having haploid genomes as described, for example, in WO 01/32015.

Methods for isolating human pluripotent stem cells are described, for example, by Trounson, A. O. Reprod. Fertil. Dev 2001; 13 (7-8): 523-32. For example, isolation can require feeder cells (and 20% fetal calf serum) or conditioned medium from feeder cells or feeder cells and mechanical disaggregation (Reubinoff et al 2000). Further methods for producing pluripotent cells are known from WO 01/30978 where the derivation of pluripotent cells from oocytes containing DNA of all male or female origin is described. In addition, stem cell-like lines may be produced by cross species nuclear transplantation as described, for example, in WO 01/19777, by cytoplasmic transfer to de-differentiate recipient cells as described, for example, in WO 01/00650 or by "reprogramming" cells for enhanced differentiation capacity using pluripotent stem cells (see WO 02/14469).

Stem Cell Culture

Cell culture conditions may be modified to favour maintenance of the cells in an undifferentiated state. If conditions are not carefully selected, stem cells may follow their natural capacity to differentiate into other cells. ES cells, for example, may differentiate into cells resembling those of extraembryonic lineages. Few of the factors that regulate self-renewal of pluripotent stem cells are currently known. Typically, embryonic pluripotent stem cell lines are isolated and maintained on mitotically inactive feeder layers of fibroblasts or with specific conditioned medium or, for murine (but not human) ES lines, with leukemia inhibitory factor Typically, culture systems for ES cells comprise the use of media such as Dulbecco's modified Eagle's medium (DMEM) as a basal media with the addition of amino acids and beta mercaptoethanol, serum supplementation (normally Fetal Calf Serum (FCS)), and a embryonic mesenchymal feeder cell support layer. Basal media and serum supplements can be obtained from a number of commercial sources. However, any media or serum is subject to variability and even small variations can effect the ES cell culture conditions.

Cells maintained in their undifferentiated state may be subjected to control differentiating conditions to generate cells of the desired somatic lineage. Cultured stem cells can be induced to differentiate by separation of stem cells from feeder cells or by growth of stem cell colonies in suspension culture to form embryoid bodies which upon dissociation can be plated to yield differentiating cells. Conditions for obtaining differentiated cultures of somatic cells from ES cells are described, for example, in PCT/AU99/00990. Leukaemia inhibitory factor (LIF) has been identified as one of the factors that can maintain pluripotent stem cells; LIF can replace the requirement for feeder cells for murine ES cells (see Nichols et al; (1990) Development 110; 1341-1348). Differentiation by removal of LIF is described herein.

For human ES cell lines, growth on primary embryo fibroblasts (pefs) can limit differentiation. Differentiation can be induced by growth without feeders (pefs) on gelatin-or fibronectin-treated plates. Suitable conditions for differentiation of human ES cells are described herein.

Modulating 5T4 Expression or Activity

The "functional activity" of a protein in the context of the present invention describes the function the protein performs in its native environment. Altering or modulating the functional activity of a protein includes within its scope increasing, decreasing or otherwise altering the native activity of the protein itself. In addition, it also includes within its scope increasing or decreasing the level of expression and/or altering the intracellular distribution of the nucleic acid encoding the protein, and/or altering the intracellular distribution of the protein itself.

The functional activity of 5T4 may be modified by suitable molecules/agents which bind either directly or indirectly to 5T4, or to the nucleic acid encoding it. Agents may be naturally occurring molecules such as peptides and proteins, for example antibodies, or they may be synthetic molecules. Methods of modulating the level of expression of 5T4 include, for example, using antisense techniques. Antisense constructs are described in detail in U.S. Pat. No. 6,100,090 (Monia et al), and Neckers et al., 1992, *Crit Rev Oncog* 3(1-2):175-231, the teaching of which documents are specifically incorporated by reference. Other methods of modulating gene expression are known to those skilled in the art and include dominant negative approaches as well as introducing peptides or small molecules which inhibit gene expression or functional activity.

Uses of Stem Cells

A number of applications for stem cells are known. For example, ES cells may be used as an in vitro model for differentiation, especially for the study of genes which are involved in the regulation of early development. ES cells also have potential utility for germline manipulation of livestock animals by using ES cells with or without a desired genetic mutation.

The therapeutic uses of mammalian stem cells are reviewed, for example, in Lovell-Badge, Nature Insight Review, November 2001, 88-91. Some types of human stem cells, such as bone marrow and skin have been used in therapies for leukemia or skin replacement while others are being used in trials including fetal midbrain cells for Parkinson's disease, and pancreatic duct cells for diabetes.

A number of uses for mouse ES cells have been demonstrated in animal models (as reviewed in Donovan and Gearhart, 2001) and include generation of cardiomyocytes to form functioning intracardiac grafts, generation of myelin from glial precursors and the introduction of a genetically modified insulin-producing ES cell line to normalise glycaemia. Initial results from studies using human pluripotent stem cells in animal models suggest that neuronal cells may be useful in treatment of stroke patients whereas there are number of potential applications for mesenchymal-derived stem cells including cardiac muscle repair, bone regeneration and joint repair.

The invention is further described, for the purposes of illustration only, in the following examples in which reference is made to the following Figures and Tables:

Table 1 shows the results of FACS analysis of 9A7 activity against a panel of murine cell lines. $10^5$ cells of each line were stained with 9A7 and analysed by FACS. Results are representative of three individual cultures and staining experiments.

Table 2. Expression of m5T4 antigen mediates a reduced mean cell volume. FACS was used to assess the forward scatter profile of mid-log phase cultures of the cell lines listed. The geometric mean of the forward scatter was taken as a measure of average cell volume. These results are representative of three separate experiments.

Table 3. Common makers of ES cell differentiation

Common markers used for determination of ES cell integrity and differentiation.

Alkaline phosphatase (Rathjen et al., 1999); Forssman antigen (Ling and Neben, 1997); Oct-3/4, octamer binding protein-3/4 (Lake et al., 2000; Rathjen et al., 1999); Rex-1, reduced expression-1 (Ben-Shushan et al., 1998; Lake et al., 2000; Rathjen et al., 1999); SSEA-1, stage-specific embryonic antigen-1 (Ling and Neben, 1997); Fgf-5, fibroblast growth factor-5 (Lake et al., 2000; Rathjen et al., 1999); ZG-ζ-globin (Bielinska et al., 1996); Bmp-2, bone morphogenic protein-2 (Weinhold et al., 2000); T-Bra, brachyury (Weinhold et al., 2000); Flk-1, vascular endothelial growth factor receptor-2 (VEGFR-2) (Hirashima et al., 1999); K-18, keratin-18 (Weinhold et al., 2000); Bmp-4, bone morphogenic protein-4 (Weinhold et al., 2000); NF-68, neurofilament-68k (Itskovitz-Eldor et al., 2000); Vim-vimentin (Weinhold et al., 2000); AFP, α-fetoprotein (Weinhold et al., 2000); TTR Transthyretin; meso-mesoderm (Abe K, 1996). ES-embryonic stem cell; Ecto-ectoderm; Endo-endoderm; Meso-mesoderm.

FIG. 1. The Rabbit anti-m5T4 polyclonal antisera is specific for m5T4 by FACS. Panel A shows the effect of a decreasing concentration m5T4-Fc upon the binding of a constant concentration of Rabαm5T4 to B16 F10-m5T4 cells. Cells were analysed by FACS and results expressed as a percentage of the maximal geometric mean. Panels B-D; Grey profiles show A9-m5T4 transfectants stained with Rabαm5T4 (1:300 B-D). White profiles show A9-m5T4 (B-rabbit pre-immune serum 1:300), A9H12 neomycin control (C-Rabαm5T4 1:300) and A9-h5T4 (D-Rabαm5T4 1:300).

FIG. 2. Specificity of the 9A7 antibody for m5T4 cDNA transfected cells by FACS. Grey profiles show A9-m5T4 (9A7, A-C). White profiles show A9m5T4 (rat IgG, A), and A9H12 neomycin (9A7, B), A9-h5T4 transfectants (9A7, C).

Panel D shows the effect of a decreasing concentration of human or mouse 5T4-Fc upon the ability of a constant concentration of 9A7 to stain A9m5T4 cells. Cells were analysed by FACS and results expressed as a percentage of the maximal geometric mean.

FIG. 3. 9A7 is specific for m5T4 by ELISA. The capacity of various antigens to inhibit the binding of 9A7 to m5T4-Fc was investigated. Antigen was titrated in a constant concentration of 9A7 (1 µg/ml) and immediately applied to m5T4-Fc coated plates (1 µg/ml).

FIG. 4. The 9A7 epitope maps to the membrane proximal region of m5T4. A9 cell lines expressing human-mouse 5T4 (A and Ci) or mousehuman 5T4 chimeric cDNA constructs (B and Cii), in a stable manner, were labelled with 9A7 (grey profiles) or MAb 5T4 (white profiles). Panel C shows a diagrammatic representation of the 5T4 chimeric molecules. Mouse sequences are shown in grey and human sequences in black. From the amino terminus the domains are labelled; N (amino terminal flanking region), LRR1 (leucine rich region repeat 1), HP (hydrophilic region), LRR2 (leucine rich region repeat 2), C (C terminal flanking region), TM (trans-membrane region) and CYT (cytoplasmic domain).

FIG. 5. Biochemical analysis of the 9A7 epitope by Western blot (A) 9A7 specificity. Lanes were loaded with 50 ng of human (h) or mouse (m) 5T4-Fc fusion protein under reducing (Ai) or non-reducing (Aii) conditions and probed with a rat anti-m5T4 polyclonal antiserum (1:200) or 9A7 (51 g/ml). (B) Carbohydrate and the 9A7 epitope. Lanes were loaded with 50 ng of m5T4-Fc pre-treated with either nothing (1), sham-treatment (2) or enzyme (3), run under non-reducing conditions and probed with anti-human IgG-Fc HRP (1:2000) to confirm protein loading or 9A7 (51 g/ml) to confirm epitope integrity. (C) Full-length m5T4. Non-reduced Western blot of cell lysates (Ci) and a 9A7 immunoprecipitation (Cii) from A9 cells; wild type (wt), neomycin control (neo), human (h) or mouse (m) 5T4. Cell lysates were loaded at $4 \times 10^5$ cell equivalents/lane (i), and 106 cell equivalents were immunoprecipitated with 5 µg of 9A7 with the entire reaction loaded (ii). Both panels (Ci and Cii) were probed with Rabam5T4 (1:3000).

FIG. 6. Distribution of m5T4 at the cell surface. A9h5T4 (A-B), A9m5T4 (C-D) and B16 F10-m5T4 (E-F) cells were pre-fixed and stained with MAb 5T4 (A-B) or 9A7 (C-F) and analysed by confocal microscopy. Panels show, the entire Z stack projection (A, C, E) or a single Z slice at midpoint of Z stack (B, D, F). Each image contains a standard 10 µm bar.

FIG. 7. The distribution of m5T4 after disruption of the cytoskeleton. Cells were left untreated (A) or treated with the cytoskeletal poisons Demecolcine (B) or Cytochalasin D (C) to disrupt the microtubule network or the actin fillaments respectively. 2 hours later cells were labelled with 9A7 and analysed by confocal microscopy. Each image contains a standard 10 µm bar.

FIG. 8. 5T4 antigen expression affects the proliferation and growth patterns of A9 cells. Panels A, B and C show typical fields of view of A9H12 Neomycin control cells (A), A9-h5T4 cells (B) and A9-m5T4 cells (C) at 200× magnification. All cultures were seeded in 10% FCS. 24 hrs later the medium was changed to 1% MEM-α and cells cultured for a further two days before image capture.

FIG. 9. 5T4 expression and cell adhesion. Panel A. $10^6$ cells were seeded into 6-well plates in medium supplemented with 0.25, 1 and 5% FCS. 24 hours later the percentage of seeded cells attached was calculated. Panel B. Extracellular matrix proteins and adhesion. $10^3$ cells were loaded into protein-coated wells in serum free α-MEM containing 25 µg/ml transferrin. 24 hours later wells were washed and adhesion measured by crystal violet incorporation.

FIG. 10. The expression of 5T4 cDNA by A9 fibroblasts enhances their motility but does not affect their capacity to invade. The relative capacity of various A9 cell lines to pass across a Matrigel coated (A-invasion) or non-coated tissue culture inserts (B-motility) was assessed Cells numbers were scored by measurement of incorporated crystal violet. Results are expressed as the percentage of all cells, which were present on the lower membrane.

FIG. 11. Immunohistochemical analysis of murine tissues with 9A7. Transverse sections of 17.5 day mouse placenta (A-D) and longitudinal sections of adult mouse brain (E-F) were labelled with rat IgG1 (A, C, E) or 9A7 (B, D, F). Brown colouration represents antibody labelling. Images were captured at 200× magnification.

FIG. 12. Cell surface 5T4 oncofoetal antigen is upregulated on ES cells following removal of LIF. (a) Cell surface expression of 5T4 on ES cells. (i) MESC, (ii) D3, (iii) OKO160 and (iv) 129 ES cells were differentiated for 12 days as monolayer cultures by removal of LIF from the growth medium and cell-surface 5T4 measured using rat anti-m5T4 monoclonal antibody 9A7 (open population) or control rat IgG (filled population). Primary antibodies were detected using FITC-conjugated rabbit anti-rat Ig and cell fluorescence measured in a Becton Dickinson FACScan. Viable cells were gated using forward and side scatter and the figure shows the fluorescence of this population. Percentages indicate the proportion of the population expressing 5T4. Day 0—undifferentiated cells; Day 12—12 days following removal of LIF.

(b) Total 5T4 protein expression in ES cell. (i) MESC, (ii) D3, (iii) OKO160 and (iv) 129 ES cells were differentiated for 12 days as monolayer cultures by removal of LIF from the culture medium, lysed ($1.2 \times 10^7$ cells/ml) and 20 µl of the lysate separated by unreduced SDS-PAGE. The membrane was probed using rabbit anti-m5T4 polyclonal serum followed by HRP-conjugated sheep anti-rabbit immunoglobulins and developed by enhanced chemiluminescence. Graphs show the densitometric analysis of the 5T4 bands, with arbitrary density values on the y-axis and days post-removal of LIF on the x-axis. Controls are mouse A9 cells transfected with m5T4 cDNA (positive) or vector control (negative).

FIG. 13. Upregulation of 5T4 expression following removal of LIF correlates with differentiation of ES cells. (a) Transcript expression profiles of ES cells following removal of LIF. (i) MESC, (ii) D3, (iii) OKO160 and (iv) 129 ES cells were differentiated for 12 days as monolayer cultures by removal of LIF from the growth medium. RNA was extracted from the cells at the specified time points, DNase treated and cDNA synthesised from the mRNA transcripts. RT-PCR was performed for 35 cycles, the samples run on 2% agarose gels containing 400 ng/ml ethidium bromide and visualised on a L transilluminator. β-tub (housekeeping gene) is included for comparison purposes. To ensure the absence of genomic DNA, RT-PCR detection of β-tub was performed on all samples without prior formation of cDNA (mRNA sample). See Table 3 for description of markers used. D0—undifferentiated cells; D12—12 days following removal of LIF. (b) Expression of Forssman antigen on ES cells following removal of LIF. ES cells were differentiated for 12 days as monolayer cultures by removal of LIF from the growth medium. Forssman antigen was determined at the specified time points on differentiating (i) MESC, (ii) D3, (iii) OKO160 and (iv) 129 ES cells using rat anti-Forssman antibody (open population) or control rat IgM (closed population), detected as described in the legend to FIG. 12. Viable cells were gated using forward and side scatter and the figure shows the fluorescence of this population. Day 0—undifferentiated cells; Day 12—12 days following removal of LIF.

FIG. 14. 5T4 is transcriptionally upregulated on ES cells following removal of LIF and the antigen associates with all primary germ layers. (a) 5T4 transcript expression in differentiating ES cells. (i) MESC and (ii) OKO160 ES cell lines were differentiated for 12 days as monolayer cultures by removal of LIF from the growth medium. cDNA was prepared at the specified time points, as described in the legend to FIG. 13, and semi-quantitative RT-PCR analysis (25 cycles) of m5T4 was performed. Samples were run on 2% agarose gels containing ethidium bromide and visualised on a UV transilluminator. β-tub (housekeeping gene) is included for standardisation. D0—undifferentiated cells; D12—12 days following removal of LIF.

(b) 5T4 antigen is expressed on cells derived from all three germ layers following removal of LIF from ES cells. MESC ES cells were differentiated for 3, 6 and 9 days as monolayer cultures by removal of LIF from the growth medium and 5T4-positive cells purified using anti-5T4 monoclonal antibody 9A7 and MidiMACS LS columns. cDNA was prepared as described above in legend to FIG. 13 followed by RT-PCR analysis of various germ layer specific transcripts (see Table 3). Samples were run on 2% agarose gels containing ethidium bromide and visualised on a UV transilluminator. β-tubulin (housekeeping gene) is included for standardisation. D3—3 days following removal of LIF; D9—9 days following removal of LIF.

FIG. 15. Expression of 5T4 antigen in differentiating ES cells is associated with the differentiation rate. (a) Expression of 5T4 antigen correlates with cell migration in differentiating ES cells. (i) MESC and (ii) 129 ES cells ($10^5$ cells/3 cm dish) were grown for 0, 3 and 6 days in DMEMSR in the absence of LIF and viewed under phase contrast on an Olympus inverted microscope. Small arrows show undifferentiated ES cells and large arrows differentiated/migrating cells. (b) Expression of 5T4 correlates with the proliferation rate of differentiating ES cells. (i) MESC and (ii) 129 ES cells ($10^5$ cells/3 cm dish) were grown in DMEMSR medium in the absence (■) or presence (◆) of LIF (arrow indicates day of LIF removal) for 3 days and the number of viable cells determined by light microscopy of cells excluding trypan blue. Bar=10 μM.

FIG. 16. 5T4 antigen is associated with migrating and non-migrating cells in differentiating ES cell cultures. 129 ES cells were grown in medium containing either differentiation-inducing foetal calf serum (a-c; f-h) or synthetic serum DMEMSR) (d; i-k) in the presence of LIF for 2 days in gelatin-treated plates. (a-d) 5T4 expression was determined using an Olympus BX-51 fluorescent microscope and images overlaid using Adobe Photoshop. Nuclear staining (DAPI) is shown in blue and 5T4 (FITC) in green. (e) FACS analysis of differentiated (i) and undifferentiated (ii) 129 ES cells demonstrating the presence of cell surface 5T4 on differentiated cells. (f-k) Confocal images of differentiated (f-h) and undifferentiated (i-k) cells showing 5T4 (f and i; FITC), phase contrast (g and j) and overlay of the 5T4 and phase contrast images (h and k). Note the lack of nuclei resolution in the undifferentiated phase contrast image (j), probably as a result of the compacted colony morphology of the undifferentiated ES cells. Bar=10 μM.

FIG. 17. Expression of EGFP-h5T4 in undifferentiated ES cells alters colony morphology. 129 ES cells were electroporated with 20 μg plasmid DNA and plated into gelatin-treated 9 cm dishes. (a) After 24 h, one third of the cells were assayed for EGFP expression in a Becton Dickinson FACScan (Becton Dickenson; Oxford, UK). Viable cells were gated using forward and side scatter and the figure shows the fluorescence of this population. EGFP positive cells were isolated from the remainder of the sample by FACSVantage SE (Becton_Dickenson) and plated out in fresh gelatin-treated 9 cm tissue culture dishes. (b) Cellular localisation of EGFP proteins was determined after 48 h using an Olympus BX-51 fluorescent microscope. (c) Cell morphology was determined 48 h after transfection using inverted light microscopy. Bar=10 μM.

FIG. 18. Presence of 5T4 on ES cells is a measure of decreased pluripotency. 129 ES cells were cultured in (a) the presence or (b) absence of LIF for 6 days and (i) SSEA-1 positive cells isolated by FACS (boxed area). (ii) 5T4 expression of the SSEA-1 positive population was determined using antibody 9A7 as described in the legend to FIG. 12a Pluripotency of the SSEA-1 positive cells was determined by chimera formation following injection of 15 cells into 3.5 day old BL/6 blastocysts and subsequent implantation into pseudopregnant BDF-1 female mice.

FIG. 19 shows 5T4 expression by FACS analysis of human Tera-2 clone 13 embryonal carcinoma cells (positive control) and pefs (negative feeders).

FIG. 20 5T4 oncofoetal antigen expression on GCT27 grown on pef feeders or on gelatin coated dishes.

FIG. 21 5T4 oncofoetal antigen expression on GCT35 grown on pef feeders or on gelatin coated dishes.

FIGS. 22a and 22b show morphology of human ES colonies.

FIGS. 24 to 27. Illustrate dual 5T4/Oct-4 staining of hES colonies showing 5T4 expression is mutually exclusive with OCT-4.

Figure 28:
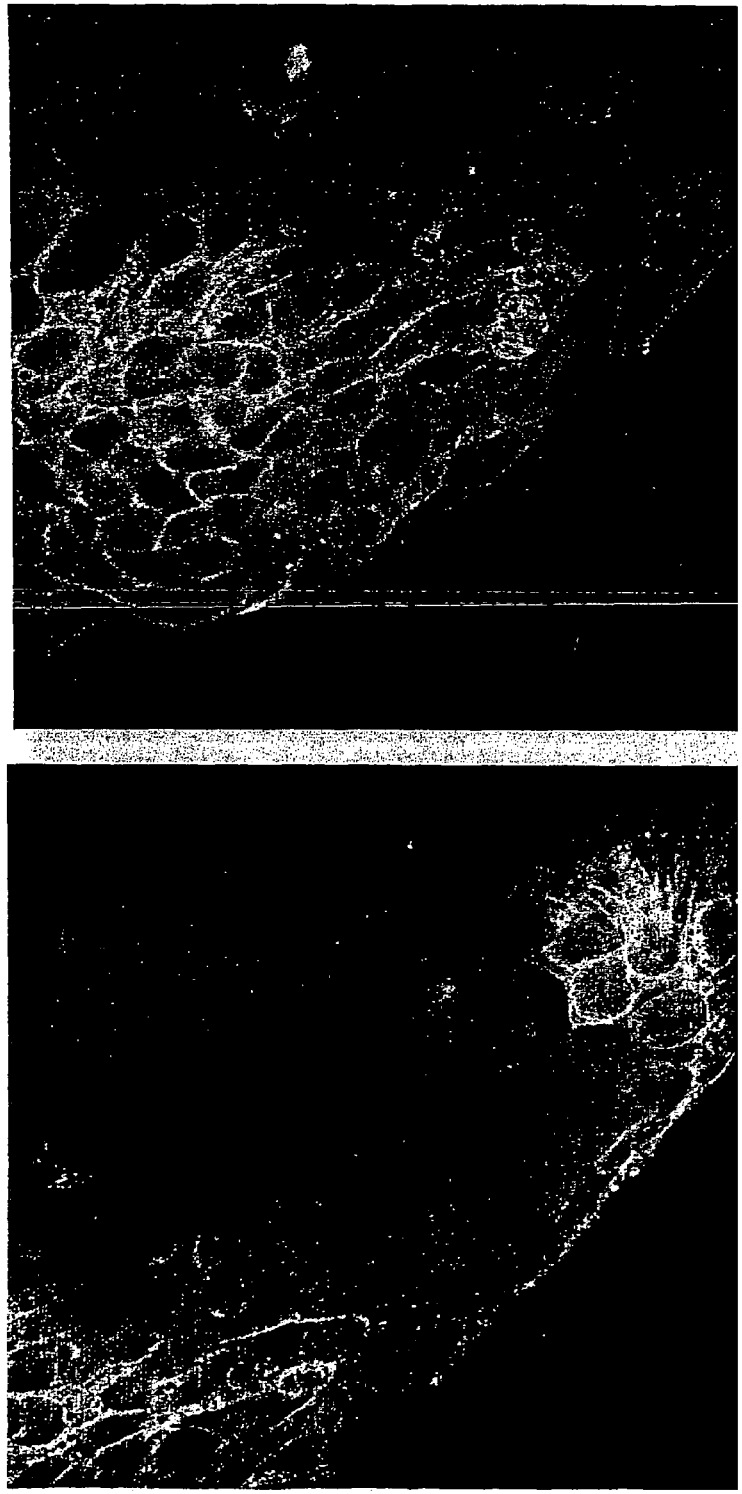

FIG. 28 Confocal microscopy of dual 5T4 and OCT-4 labelling of two differentiating ES colonies.

Figure 29:
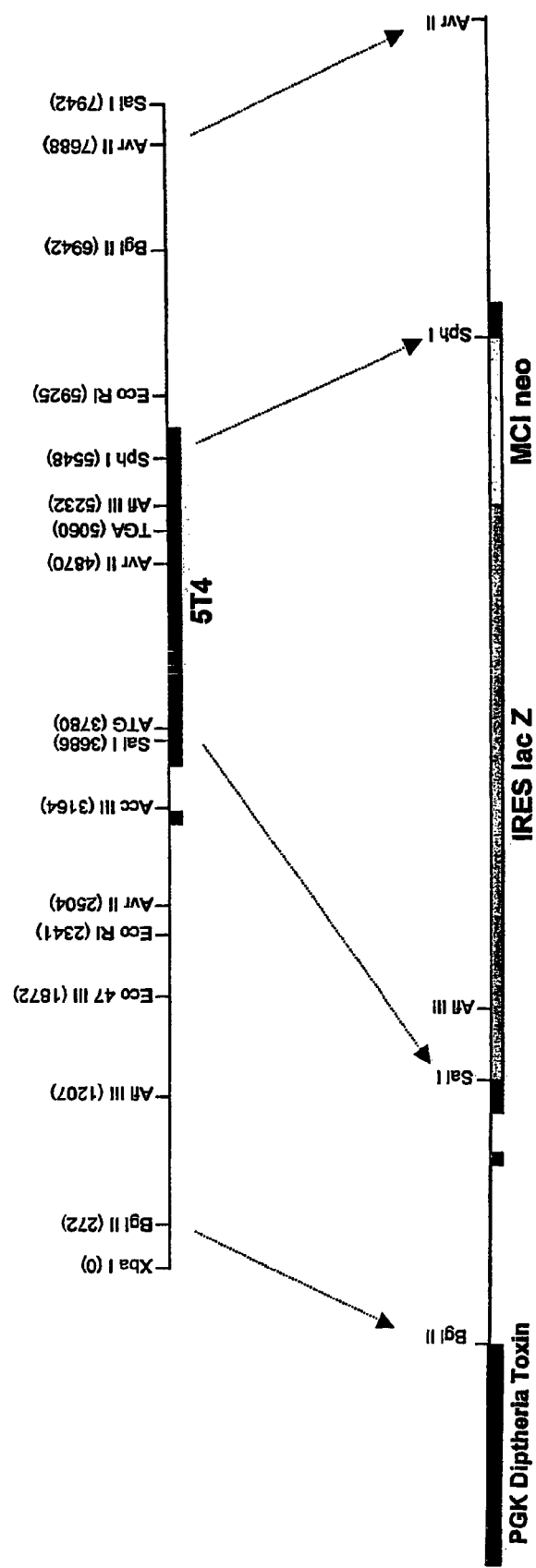

FIG. 29 shows the construct used for homologous recombination in mouse studies. The upper section is a concise restriction map of genomic murine 5T4; showing the coding sequence of murine 5T4 (shaded region). The lower section is the targeting construct used for homologous recombination into the 5T4 locus. This shows *E. Coli* LacZ; PGK Dipetheria toxin as negative insertion selector and MCI neo which allows positive selection of the knock in ES cells. Method as described in Gene Targeting A Practical Approach Ed. AL Joyner, $2^{nd}$ Edition Oxford University Press 2000.

FIG. 30 β-gal staining of undifferentiated and differentiated 5T4 KO/LacZ knock in ES cells FIG. 31: Expression of cell-surface 5T4 in MESC ES cells differentiated for 12 days as suspended embryoid bodies The invention is further described below, for the purposes of illustration only, in the following examples.

EXAMPLES

Example 1

Generation of m5T4 Specific Antibodies and m5T4-expressing Cell Lines

Materials and Methods

5T4-Fc Fusion Proteins

A 1004 bp cDNA fragment encoding the extracellular domain of mouse 5T4 antigen was generated by PCR and cloned by restriction digestion into the signal-pIg plus expression vector (Ingenious, R&D systems). Stable expression in Cos-7 cells (Shaw et al. (2000)) was achieved by selection in G-418 at 1 mg/ml. Mouse and human 5T4-Fc fusion proteins were fractionated from tissue culture supernatant by ammonium sulphate precipitation and purified by wheatgerm agglutinin and protein G affinity chromatography. The concentration was determined by anti-human Fc-capture ELISA (Shaw et al. (2000)) and modified Bradford assay Bradford (1976)).

Purity was assessed by silver stained SDS-PAGE. The Fc domain of m5T4-Fc was removed by overnight digestion with factor Xa protease (Roche). M5T4 extracellular domains (m5T4ex) were then enriched by negative selection on a protein G column and concentrated by centrifugal spin filter (Shaw et al. (2002)).

ELISA

Plates were coated with 50 µl of antigen at 1 µg/ml in 0.1M sodium carbonate buffer pH 9.3 overnight at 4° C. Plates were washed with PBST three times between each layer. Non-specific binding sites were blocked with 5% milk powder in PBST for 1 hour at 37° C. Plates were incubated successively for 1 hour at 37° C. with 50 µl per well of each of the following; test sample, biotinylated mouse anti rat κ/λ (1:3000 Sigma) and streptavidin HRP (1:6000 Dako). Reactions were developed with 100 µl of tetra-methyl benzidine at 0.1 mg/ml in 50 mM citrate phosphate buffer pH5.5, stopped by the addition of 50 µl of 1M sulphuric acid and read at 450-650 nm.

Polyclonal Antisera

Rabbits were immunised subcutaneously with 100 µg of purified m5T4-Fc in Freunds complete adjuvant and boosted on a fortnightly regime using Freunds incomplete adjuvant.

Anti-m5T4 activity was assessed by ELISA-based assay against m5T4ex on alternate weeks. Upon acquisition of significant anti-m5T4ex activity, rabbits were terminally bled by cardiac puncture, serum harvested, aliquoted and stored at −20° C.

Cell Culture

Non-adherent cells were grown in RPM 1640 and adherent cells in DMEM (Sigma) supplemented with 2 mM L-glutamine and 10% FCS; transfected cell lines were maintained under selection with 1 mg/ml of G-418. Cells were maintained in a humidified atmosphere of 5% $CO_2$/air at 37° C. and passaged on reaching 90% confluence. Four-day conditioned medium was prepared from confluent cultures of Y3Ag1.2.3. Fusion media comprised RPMI supplemented to 20% FCS, 50% conditioned medium, 2 mM L-glutamine, 2 mM sodium pyruvate and 1×DMEM non-essential amino acids (Sigma). Hybridoma cloning was performed in fusion media supplemented with 10 ng/ml human epidermal growth factor.

Flow Cytometry

Adherent cells were removed from flasks with trypsin and washed three times at 4° C. with FACS buffer: PBS plus 0.1% BSA and 0.1% sodium azide. $10^5$ cell aliquots were transferred to a 96 well v-bottom plate, pelleted by centrifugation and the supernatant aspirated. All subsequent steps were incubated on ice for 30 minutes and cells washed three times with FACS buffer between layers. Tissue culture supernatants were tested neat and purified antibodies at 10 µg/ml. Rat and mouse immunoglobulins were detected with rabbit anti-rat or mouse FITC direct conjugate respectively (1:30, Dako). Prior to analysis cells were fixed for 10 minutes at 4° C. by the addition of an equal volume of 3.7% paraformaldehyde in PBS.

Cell Lines

A9 fibroblastic cells expressing human 5T4 (Carsberg et al. (1995)) or chimeric human-mouse (hm) and mouse-human (mh) 5T4 were generated as previously described (Shaw et al. (2002)). Lipofectamine was used to transfect A9 cells with m5T4 cDNA in pCMVα. Bulk cultures were grown for two weeks with G-418 at 1 mg/ml and then assessed for 5 m5T4 antigen expression with the Rabαm5T4 antisera by flow cytometry. Positive cultures were cloned by limiting dilution, assessed for m5T4 antigen expression as before and positive wells re-cloned. The murine melanoma B16 F10 was transfected by electroporation with human or mouse 5T4 cDNA in pCMVα. Stable expression was achieved by the addition of G-418 at 1 mg/ml and clones were established following two rounds of limiting dilution.

Recombinant m5T4 Vaccinia Western Reserve

The full-length m5T4 cDNA (King et al. (1999)) was cloned into the Vaccinia transfer plasmid pSC65 (Chakrabati et al. (1997)) such that it is under the control of the synthetic early promoter. Plasmid SC65-m5T4 was recombined into the tk locus of the WR strain of vaccinia virus using techniques previously described (Carroll et al. (1998)). Virus stocks were prepared in BSC-1 cells using protocols similar to that described by Earl et al Earl et al. (1998)).

Immunisation

LOU Rats (Harlan) were immunised twice intra-muscularly with $10^8$ PFU rVV-m5T4 at four-week intervals and test bled two weeks later. Four weeks after test bleeds were taken, $10^8$ syngeneic splenocytes were infected overnight with rVV-m5T4 at a multiplicity of infection of 2 and used to boost the highest responder. On day four post boost this animal was terminally bled and splenectomised.

Fusion

Cell fusion was performed by the polyethylene glycol method as previously described (Kohler et al. (1976)). Fused plasmablasts were plated at a density of $10^6$/ml in 96 well plates (100 µl per well). After 24 hrs in culture 100 µl of fusion medium containing 2×HAT (Sigma) was added. The cells were fed at days 4, 7 and 12 by 50% change of 1×HAT medium and on day 14 weaned into HT medium. At day 21, tissue culture supernatant was removed from wells positive for growth and assayed for anti-m5T4 activity by flow cytometry versus B16 F10-m5T4 or B16 F10-Neo control plasmid transfected cells and by ELISA versus m5T4-Fc fusion protein.

Positive wells were cloned four times by limiting dilution and re-screened as before. Isolated anti-m5T4 antibody isotypes were determined with a rat monoclonal antibody isotyping kit according to the instructions of the manufacturer (The Binding Site).

Antibody Production

Clarified tissue culture supernatant was brought to 45% ammonium sulphate and stirred overnight at 4° C. The precipitate was pelleted, resuspended in PBS to 10% of the original volume and dialysed at 4° C. against five changes of 100 volumes of PBS. The immunoglobulin was purified by protein G affinity chromatography and the purified antibody extensively dialysed against PBS.

Immunoprecipitation, SDS-PAGE and Western Blotting

Cells were lysed at $10^7$ per ml in PBS 0.5% NP40 containing 1× Complete protease inhibitors (Roche). Lysates were pre-cleared at 4° C. for four hours with 5 µg of control rat IgG1. Proteins coupled to rat IgG1 were complexed with 50 µl of a 50% suspension of Protein G coupled Sepharose (Amersham Biosciences) and removed by centrifugation (1000 g 1 min).

Immunoprecipitations were performed with 5 μg of test antibody, and 50 μl of a 50% suspension of protein-G Sepharose. Immunoprecipitates were washed five times with lysis buffer, resuspended in 50 μl of 1×SDS-PAGE sample buffer and boiled for 3 minutes. Samples were separated by SDS-PAGE using an Atto minigel system according to methods of Laemmli (Laemelli (1970)). Proteins were transferred electrophoretically to nitrocellulose with a Biorad Transblot semidry transfer system and blocked overnight at 4° C. in PBST containing 5% milk powder.

All antibodies were applied for 1 hr at room temperature with agitation and blots washed 5 times for 5 minutes between layers (rat IgG1 and 9A7 (10 μg/ml), rabbit anti rat-HRP (1:2000 Dako) and streptavidin-Horseradish peroxidase (1:6000 Dako). Antibody binding was detected by chemiluminesence (Amersham Biosciences) according to the instructions of the manufacturer.

Immunofluorescence Microscopy $10^4$ Cells were seeded onto acid washed 16 mm glass coverslips in α-MEM containing 1% FCS and grown for 48 hrs. Cells were washed three times with FACs buffer and fixed with 3.7% paraformaldehyde in PBS for 15 mins prior to labelling or labelled at 4° C. in FACs buffer, washed and then fixed. Antibodies were applied as follows; 9A7 (10 μg/ml), MAb5T4 (5 μg/ml), rat IgG1 (10 μg/ml) or mIgG (5 μg/ml) and the second layer rabbit anti-rat or mouse-FITC conjugate (1:30 Dako as appropriate) for 30 mins. Non-fixed samples were then washed and fixed as described previously. Samples were mounted in PBS containing 80% glycerol and 2% 1,4-Diazabicyclo[2.2.2]octane, and sealed with clear nail lacquer.

To investigate effect of cytoskeletal disruption upon 5T4 distribution, samples were incubated with 10 μg/ml of either demecolcine or cytochalasin D for two hours prior to labelling (Carsberg et al. (1995)).

Cell Attachment

Aliquots of $3\times10^5$ cells were seeded in α.MEM containing 0%, 1%, or 5% FCS in each well of a 6 well plates and incubated for 24 hr. Wells were washed three times with PBS to remove non-adherent cells and adherent cells trypsinised and counted by haemocytometer.

The effect of extracellular matrix proteins upon cell attachment was assessed in 96 well plates. Each well was coated with 10 μg of laminin, fibronectin collagen IV or matrigel in PBS overnight at 4° C. Plates were washed 3 times with PBS and $10^3$ cells seeded per well in 100 μl of serum free α.MEM containing 25 μg/ml transferrin (Sigma). Plates were incubated for 24 hrs, washed 3 times with PBS and stained with 0.01% Crystal Violet in PBS for 15 minutes. Excess dye was removed by extensive washing, plates air dried and residual dye dissolved by agitation for 30 minutes at room temperature with 100 μl per well of 10% acetic acid. The optical density was then read at 570 nm.

Proliferation

Proliferation assays were performed as described (Carsberg et al. (1995); Carsberg et al. (1996)). Briefly, $10^4$ cells were seeded in duplicate in 6 well plates in DMEM containing 10% FCS. 24 hours later the cells were washed three times and the medium replaced with α-MEM containing 0.5%, 1% or 5% FCS. Cells were trypsinised and absolute numbers determined on at 24-hour intervals with a Coulter counter.

Motility and Invasion Assay

Motility and invasion assays were performed as previously described (Carsberg et al. (1995); Carsberg et al. (1996)). Falcon cell culture inserts with a non-coated 8 μm porous polyethylene teraphthalate membrane were used for motility assays, and coated with 10 μg of Biocoat Matrigel for invasion assays (Beckton Dickinson). α-MEM containing 0.25% FCS, used for all assays, was conditioned by incubation with NIH 3T3 fibroblasts for 2 hours. 0.5 ml of conditioned medium was placed in the lower compartment and $10^4$ cells seeded in 250 μl of non conditioned medium in the upper compartment in multiples of four. Twenty-four hours later wells were washed and fixed with 3.7% paraformaldehyde in PBS for 20 minutes.

Migration to the lower chamber was assessed by removal of cells from the upper chamber of membranes (with a cotton bud) and comparison to the total number of cells remaining on both surfaces. Cells were stained with 0.01% crystal violet and then processed as for cell attachment.

Immunohistochemistry

Murine tissues examined were obtained in triplicate from both male and female mice. These included adult heart, lung, liver spleen, kidney, large intestine, small intestine, brain, testes, ovary and 17.5 day placenta.

Immunohistochemistry was performed on 5 μm cryostat sections of snap frozen tissues. Slides were fixed at room temperature for five minutes in acetone and air dried prior to re-hydration in tris buffered saline (TBS: 50 mM tris pH7.6 140 mM NaCl). Endogenous peroxidase activity was blocked by incubation in TBS containing 0.1% sodium azide and 0.1% hydrogen peroxide, at room temperature for ten minutes. The sections were blocked with 10% normal rabbit serum for 30 minutes, all subsequent steps were in TBS containing 1% normal rabbit serum and incubated for 30 minutes at 30° C.

Sections were stained with either 9A7 or a rat IgG1 at 10 μg/ml followed by the secondary antibody, rabbit anti-rat HRP direct conjugate (1:100 Dako). Anti-mouse immunoglobulin activity in the secondary antibody was neutralised by the addition of 10% mouse serum. Immediately prior to use, reagents were spun at 4° C. for 30 minutes at 13,000 rpm in a bench top microfuge. Antibody labelling was visualised with di-amino benzidine and slides counter-stained, cleared, fixed and mounted as described by Southall et al (1990).

Polyclonal Rabbit Anti-Mouse 5T4-Fc

To facilitate cloning and preliminary characterisation of m5T4 transfected cell lines, a rabbit antiserum was raised against a fusion protein of the extracellular domain of mouse 5T4 fused to human IgG-Fc (m5T4-Fc). The fourth test bleed from this rabbit showed significant anti-m5T4 activity by ELISA and after boosting, the rabbit was terminally bled and the serum Harvested. The resulting antiserum (Rabαm5T4) had a titre of 1:5000 by ELISA for the extracellular domain of m5T4 (data not shown).

Figure 1:
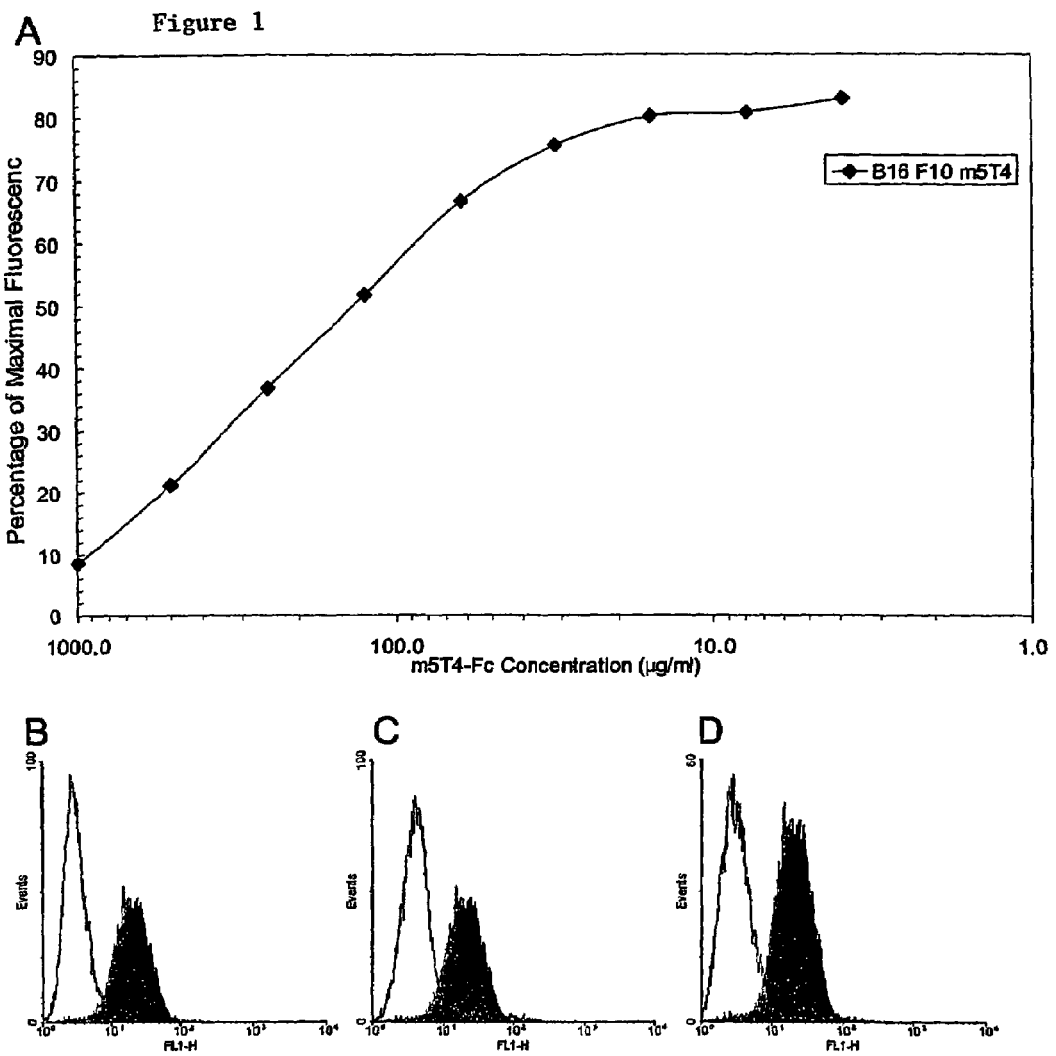

The rabbit pre-immune serum showed no activity versus control or m5T4 transfected cells by flow cytometry (FIG. 1). However, the Rabαm5T4 antiserum labelled pCMVα m5T4 cDNA transfected B16 F10-m5T4 melanoma cells and A9-m5T4 fibroblasts, but did not label control plasmid transfected A9H12 cells or h5T4 cDNA transfected A9 fibroblasts FIG. 1).

The binding of Rabαm5T4 to m5T4-Fc or B16 F10-m5T4 cells, as measured by ELISA and flow cytometry respectively, was inhibited by pre-incubation with the m5T4-Fc fusion protein (FIG. 1). This effect was titratable and could not be replicated with either hIgG or h5T4-Fc (data not shown).

These results establish the specificity of Rabαm5T4 antiserum for m5T4 by ELISA and flow cytometry (1:300 dilution) and of the expression of m5T4 molecules on the transfected B16 melanoma and A9 fibroblast cell lines.

Although specific at the cell surface, immunohistochemical analysis with Rabαm5T4 showed widespread and non-specific staining of mouse placental and liver sections (data not shown). These reactivities could not be removed by exhaustive absorption with normal liver tissue and m5T4 specific antibodies proved impossible to purify by affinity chromatography. For these reasons monoclonal rat anti-m5T4 antibodies were generated.

Generation of m5T4 Positive Cell Lines

The establishment of mouse cell lines, which showed stable m5T4 expression, was not straightforward. In the A9 cells, flow cytometric analysis showed stable expression of the m5T4-antigen over 20-25 passages. However, after passage 25 the cells began to show evidence of reduced levels of m5T4 in the population, decreased attachment, reduced proliferation after passage and failure to propagate.

These problems were not encountered during the generation of other A9 transfected cell lines expressing human or chimeric 5T4 molecules. Similarly, B16 F10-h5T4 positive cells were relatively easy to produce and maintain whilst B16 F10-m5T4 cell lines required exhaustive selection to produce cells with stable expression and behaviour in vitro. However, as the B16 F10-m5T4 cell line showed uniform growth properties and stable expression of m5T4 in culture, it was used to screen hybridoma fusions for rat anti-m5T4 antibodies by flow cytometry.

Monoclonal Antibody Isolation and Characterisation

Rats were immunised with a recombinant strain of Vaccinia West Reserve, which encoded m5T4 (rVV-m5T4) and provided antigen expression in the context of a strong adjuvant effect. Two weeks post boost, tail bleeds showed titres of 1:3000 against m5T4-Fc by ELISA with no cross reactivity towards h5T4-Fc or hIgG (data not shown). Test sera specifically stained m5T4 transfected cells by flow cytometry and could only be blocked from doing so by pre-incubation with m5T4-Fc (data not shown).

The best responder was boosted and the resultant plasmablasts harvested and fused with the Y3 Ag1.2.3 partner cell line. Of the 960 plated wells, 151 were positive for growth and 104 of these contained rat antibodies, three of which reacted specifically with the m5T4-Fc fusion protein by ELISA. These wells were designated as 8C7, 9A7 and 10F4 by location. However, flow cytometric analysis with the B16 F10-m5T4 cell line, showed that only 9A7 reacted and therefore further analysis was limited to this antibody.

Figure 2:
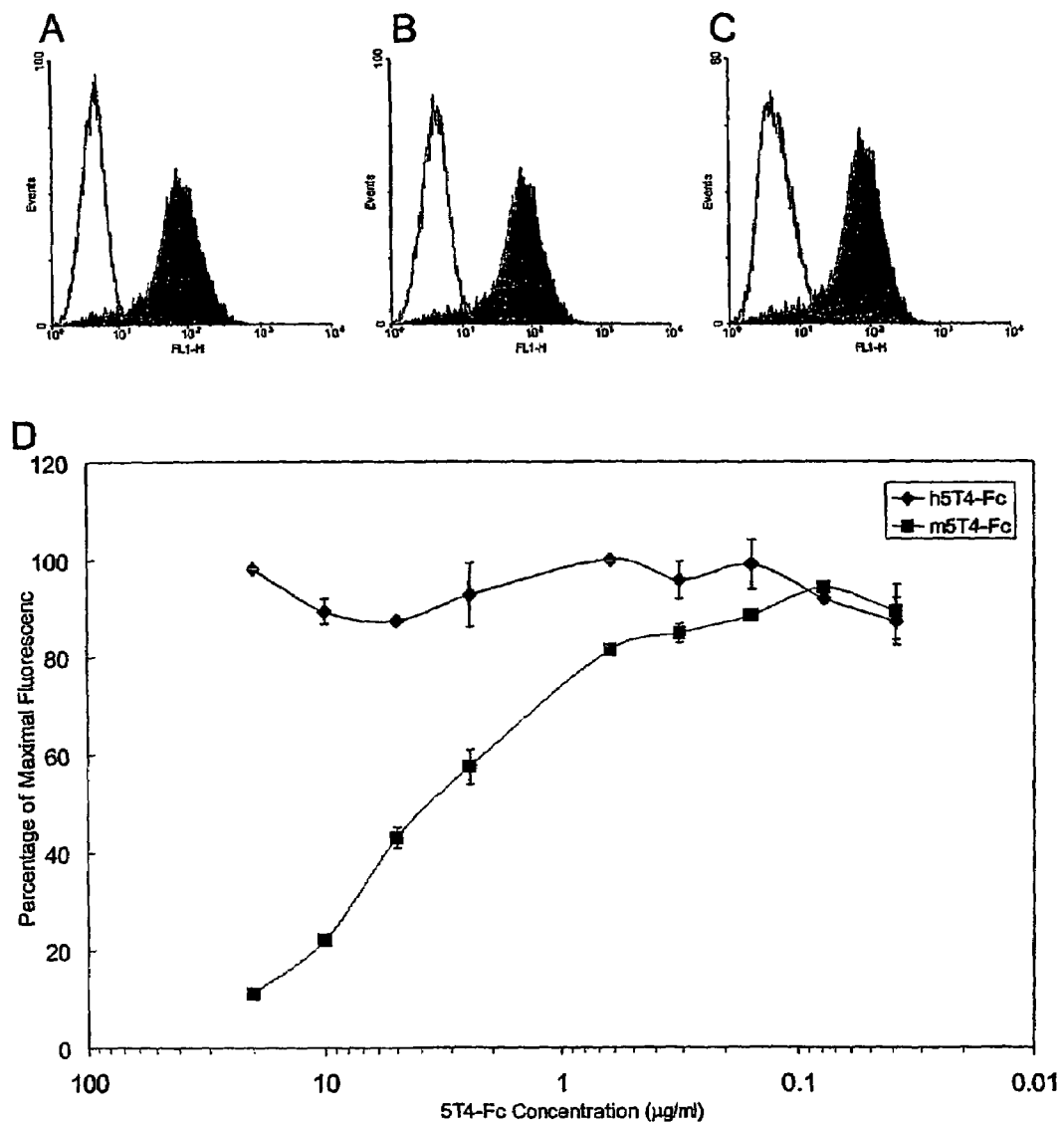

9A7 activity was specific for A9 cell lines transfected with the m5T4 cDNA and did not react with A9 cell lines transfected with either neomycin control plasmid (A9H12) or h5T4 cDNA (FIG. 2).

Figure 3:
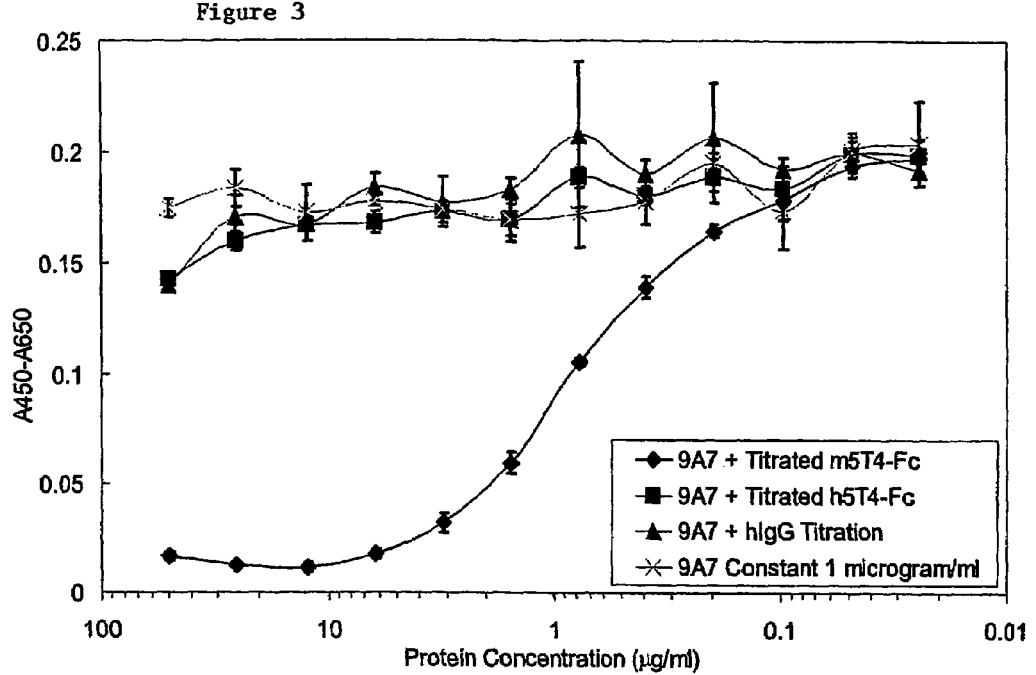

Antibody labelling could be titrated and was inhibited by pre-incubation with a five fold molar excess of m5T4-Fc (FIG. 2). Similar results were seen for B16 transfected cells (data not shown). By ELISA, 9A7 only recognised m5T4 as antigen and this recognition could be specifically inhibited by simultaneous incubation with a five fold molar excess of m5T4-Fc (FIG. 3). The inhibition of 9A7 binding to m5T4-Fc was titratable and was not affected by either hIgG or h5T4-Fc. Together, these results confirm the specificity of 9A7 for m5T4 antigen.

Epitope Mapping

Chimeric A9-5T4 cell lines (mh/hm—FIG. 4) were used to map the 9A7 epitope to a specific region of the mouse 5T4 molecule. Flow cytometric analysis showed that the 9A7 and MAb5T4 antibodies labelled the A9-hm5T4 and A9-mh5T4 chimeras respectively, in a non-reciprocal fashion (FIG. 4). Therefore, both these cell lines expressed antigenically competent chimeric 5T4 molecules. These results localised the MAb5T4 and 9A7 epitopes to the membrane proximal regions of the human and mouse 5T4 molecule respectively.

Western Blotting and Immunoprecipitation

Figure 5:
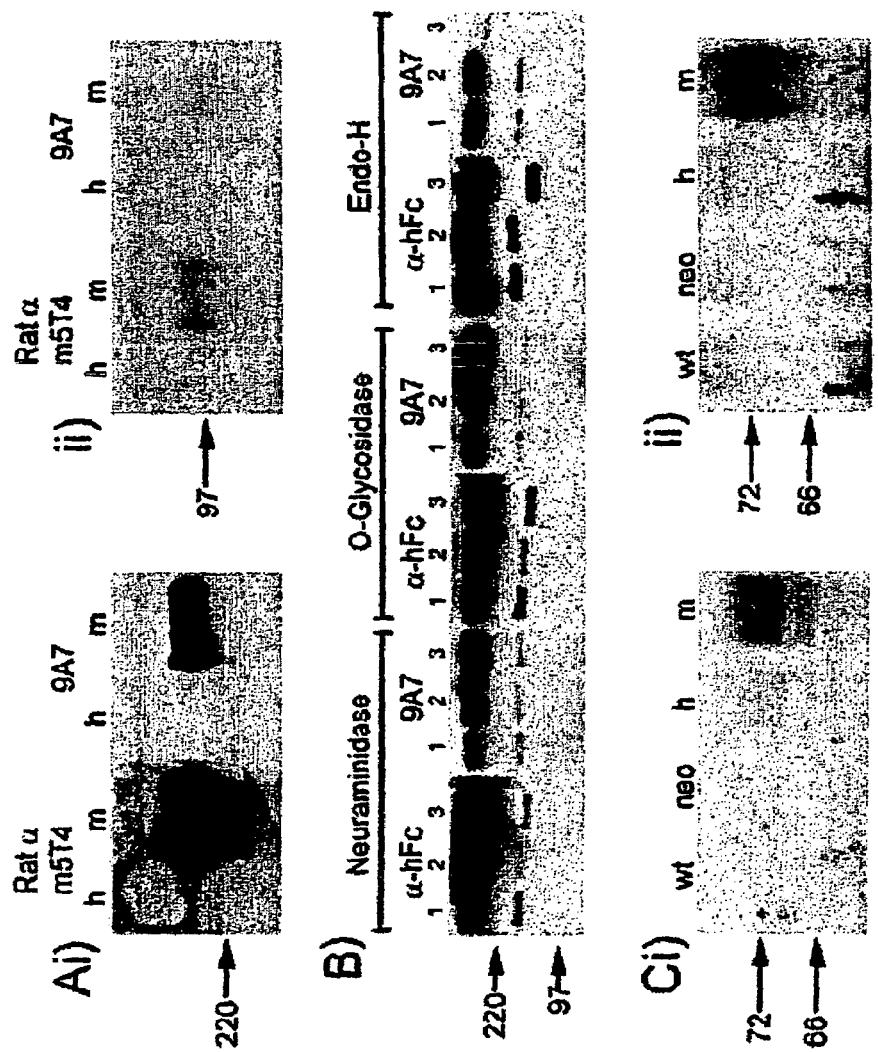

Reduced and non-reduced Western blots of the mouse and human 5T4-Fc fusion proteins were probed with either 9A7 or a polyclonal rat anti-m5T4 (Ratαm5T4; FIG. 5). Ratαm5T4 reacted specifically with both reduced and non-reduced m5T4-Fc (FIG. 5A). However, the 9A7 antibody was only specific for m5T4-Fc under non-reducing conditions, giving a small but significant signal with reduced h5T4-Fc (FIG. 5Aii). The contribution of carbohydrate moieties to the integrity of the 9A7 epitope was assessed by Western blot analysis of deglycosylated m5T4-Fc molecules (FIG. 5B). Treatment of m5T4-Fc fusion protein with neuramimidase followed by O-glycosidase produced incremental reductions in molecular mass, indicating the presence of both sialylation and O-linked glycans. Neither treatment, however, reduced the antigenicity of the 9A7 epitope. However, removal of N-linked carbohydrate moieties with endoglycosidase H led to a significant reduction in molecular mass of the m5T4-Fc molecules with the concomitant ablation of the 9A7 epitope (FIG. 5B). The precise glycosylation patterns of the fusion protein may not reflect the pattern of glycosylation of the native molecule, but the antigenicity clearly depends on N-linked sugars. By comparison to m5T4-Fc, detection of full-length m5T4 antigen by Western blotting of m5T4 cDNA-transfected cell lysates with 9A7 is relatively insensitive. However, partial purification of membrane glycoproteins by wheatgerm agglutinin enrichment from transfected A9 cell-lysates reveals a broad 72 kDa band specific to the m5T4 cDNA-transfected cells (results not shown). To corroborate this data, non-reduced Western blots of 9A7 immunoprecipitates from A9 cell lysates were probed with the Rabαm5T4 antiserum. As this antiserum cross-reacts with full-length h5T4 (FIG. 5Ci), it can be used to determine the specificity of 9A7 immunoprecipitation reactions for human or murine 5T4 molecules. The resultant 72 kDa band was only present in A9-m5T4 cell lysates, indicating that 9A7 was specific for m5T4 and did not immunoprecipitate h5T4 antigen (FIG. 5Cii).

Cellular Distribution of m5T4

Figure 6:
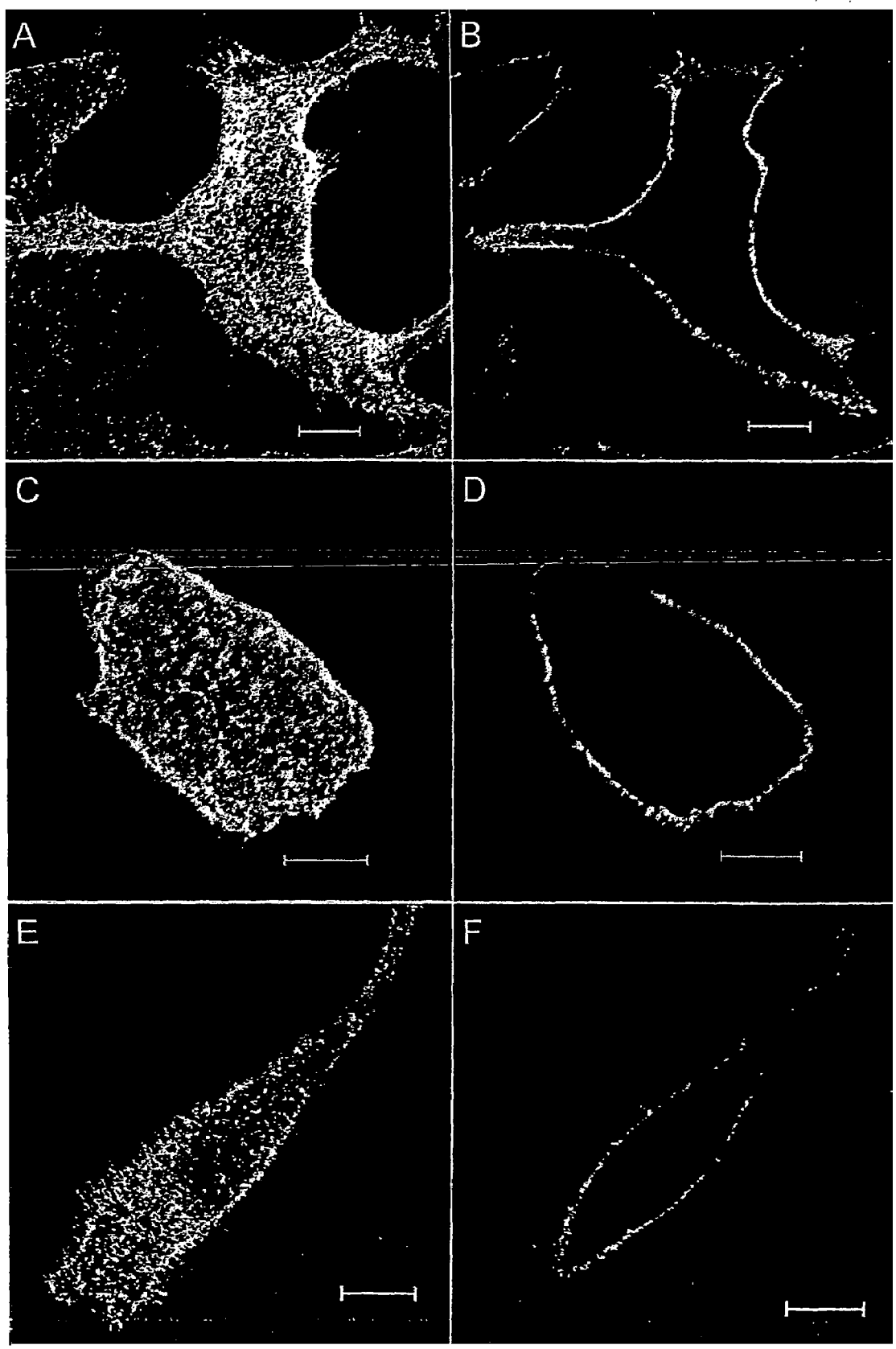

The A9-m5T4 and B16-m5T4 cell lines show a punctate pattern of labelling when stained with 9A7 (FIG. 6), which was independent of pre- or post-fixation and therefore not due to antibody induced antigen redistribution.

Similar patterns of staining were seen by confocal microscopy for the murine mammary carcinoma derived cell lines C127I and EMT6 confirming that punctate labelling was independent of CMV immediate early promoter driven expression.

Figure 7:
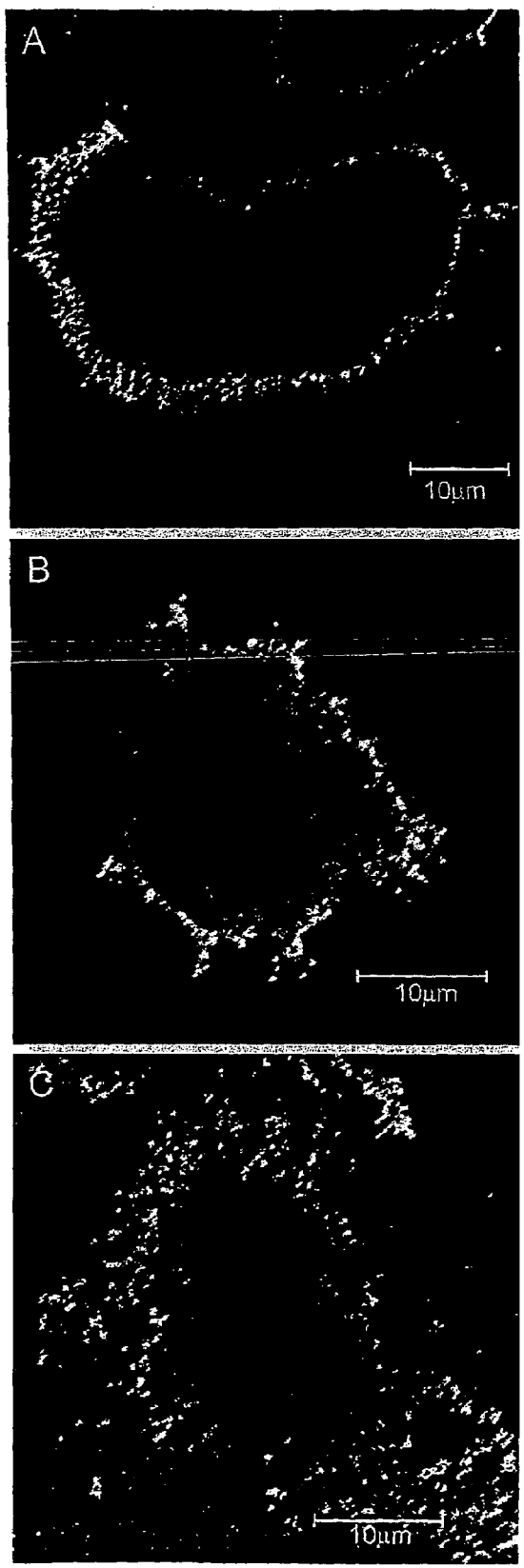

Disruption of the actin cytoskeleton with cytochalasin D led to a redistribution of punctate staining away from the periphery of the cell. This effect was not seen upon disruption of the microtubule network suggesting that the integrity of the actin cytoskeleton is an important factor in maintaining the distribution of murine 5T4 molecules (FIG. 7).

Cell lines derived from murine tumours were assessed by flow cytometry for staining with 9A7 (table 1). Positive lines included, three derived from mammary tissue, a squamous lung carcinoma and a teratocarcinoma derived embryonal carcinoma. Those that did not stain with 9A7 included a fibroblastoid cell line, two melanomas, a lymphoma, two lung arcinomas, a breast carcinoma and also an embryonic stem cell line.

Patterns of Cell Growth

Figure 8:
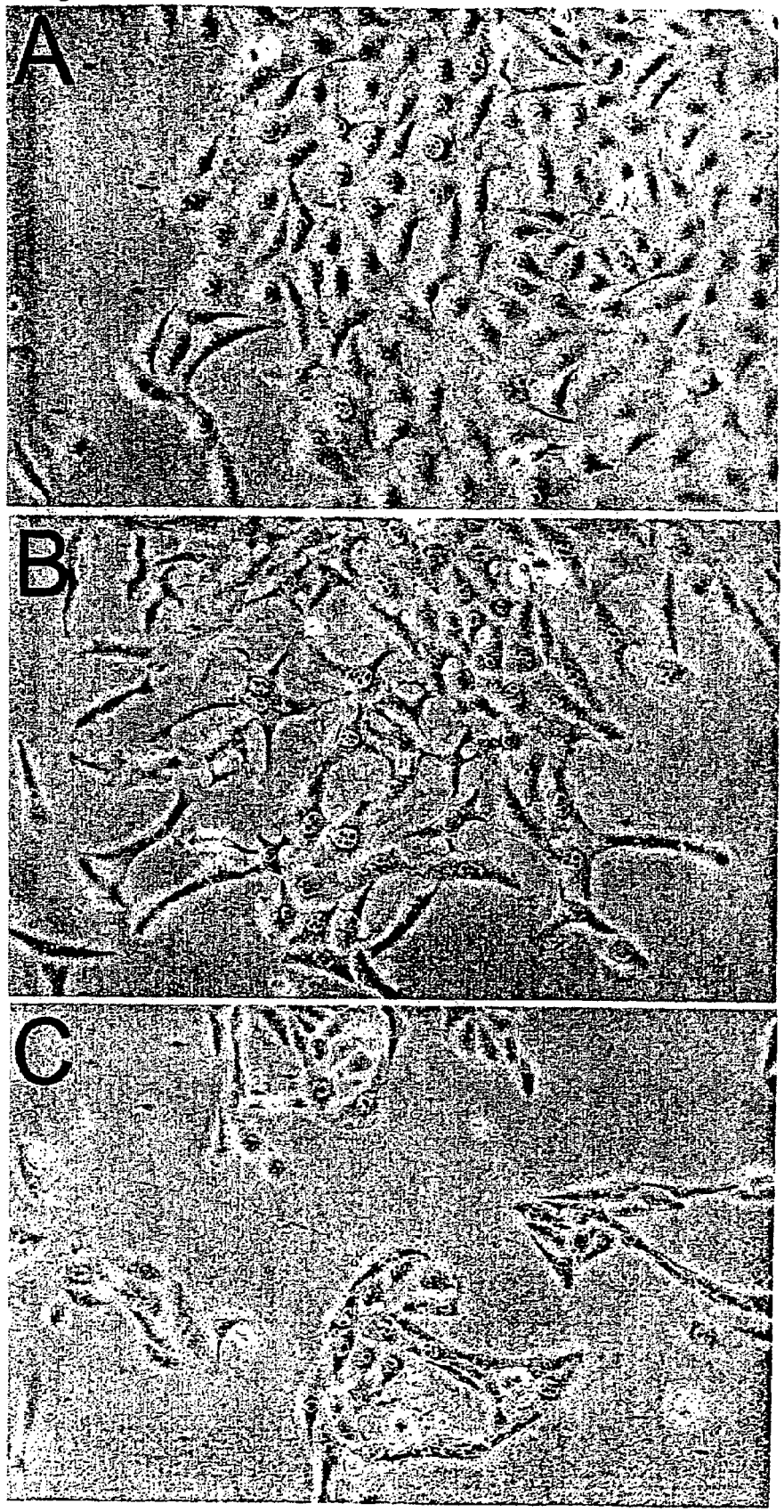

Under low serum conditions A9H12 fibroblasts grow as a "pavement" type monolayer with many cell-cell contacts with little space between cells (FIG. 8). Transfection of h5T4 into mouse fibroblasts results in a more dendritic morphology, fewer cell-cell contacts and an increased tendency to disperse (FIG. 8). The expression of m5T4 by A9 fibroblasts resulted in long spindle shaped cells compared to plasmid control transfected cells (FIG. 8).

M5T4 transfected A9 cells form colonies that stack vertically and align in a parallel fashion along the axis of the spindle. This results in the formation of "fibres" that grow by extension to connect with others, after which they spread outwards to cover the remaining free surface. This was seen in many experiments, throughout the passage window and with several independently derived clones.

A9-m5T4 antigen positive cells showed reduced proliferation when compared to the A9H12 neomycin control cell line. Of the A9-h5T4, A9-m5T4 and A9H12 cell lines, only the A9H12 neomycin cell line could be maintained in serum free media with doubling time of 75 hours. Addition to the media of FCS (0.5%) allowed all cell lines to be maintained. Proliferation rates were in the order A9H12>A9-h5T4>A9-m5T4 with doubling time of 62, 120 and 146 hours respectively. Increasing the concentration of foetal calf serum to 5% did not alter this rank order, but did decrease the differences in doubling times between the lines; A9H12, A9-h5T4 and A9-m5T4 at 53, 62 and 67 hours respectively.

Transfection of the B16 and A9 murine cell lines with m5T4 resulted in a 7% reduction of forward scatter as assessed by flow cytometry (Table 2). This implies an average reduction in cell volume upon transfection of cells with autologous 5T4. This effect was not observed in A9 fibroblasts transfected with the h5T4 cDNA, the neomycin control cassettes or the hm or mh chimeric 5T4 constructs. All cultures showed good viability with homogeneous 5T4-antigen expression by flow cytometry.

Adhesion

Figure 9:
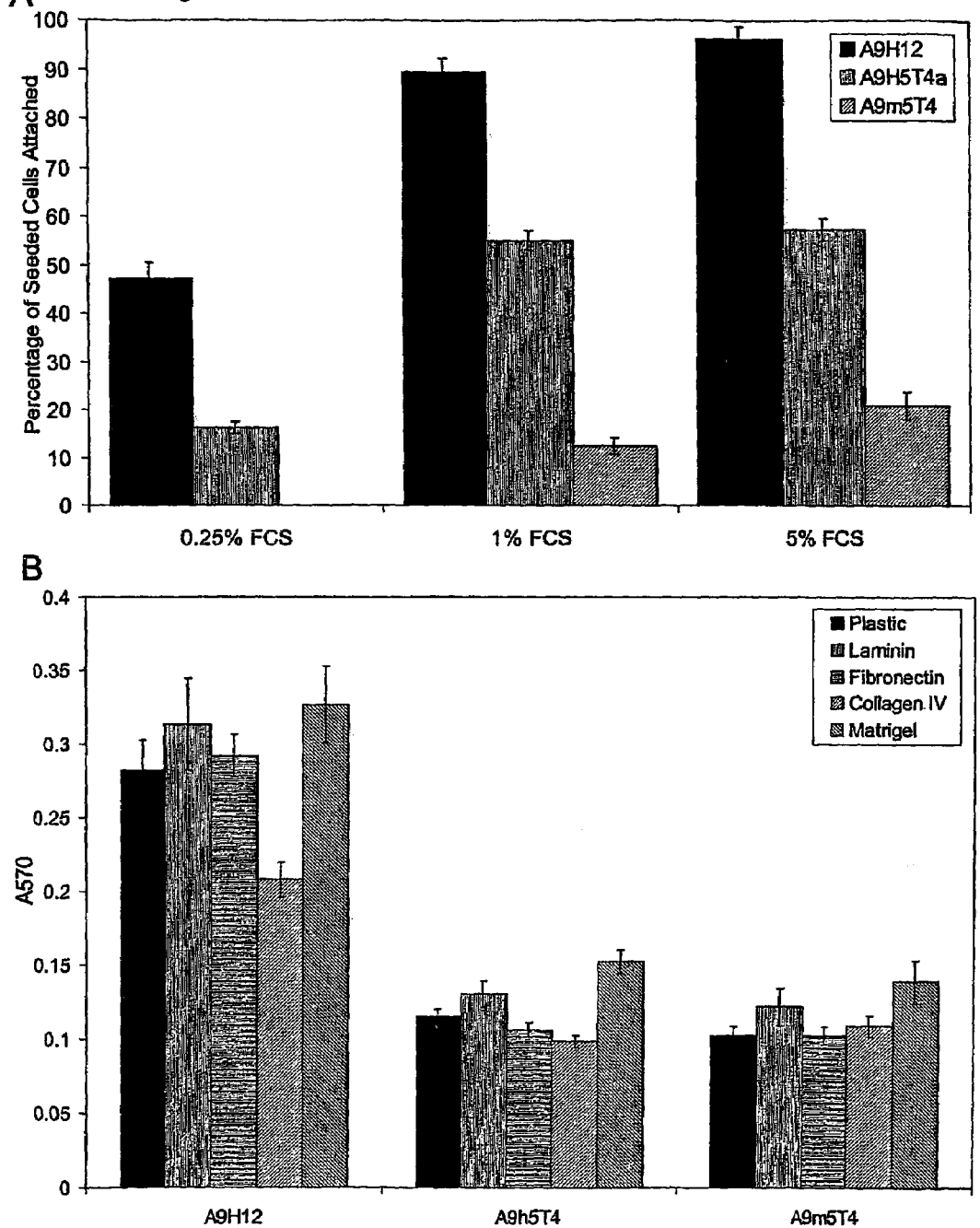

A9 cell lines exhibit serum concentration dependant attachment to plastic (FIG. 9). The degree of this effect lessened as the serum concentration was increased but the relative differences between cell lines remained. The capacity of A9-m5T4 cells to adhere to plastic shows the most pronounced sensitivity to serum concentration followed by A9-h5T4 and then A9H12.

The extracellular matrix components collagen IV, laminin and fibronectin showed little differential effect upon adhesion of cells and followed the same trend as to for adhesion to plastic (FIG. 9). However, matrigel coated wells resulted in increased adhesion of all cell lines tested but did not alter their relative propensities to adhere.

Motility and Invasion

Figure 10:
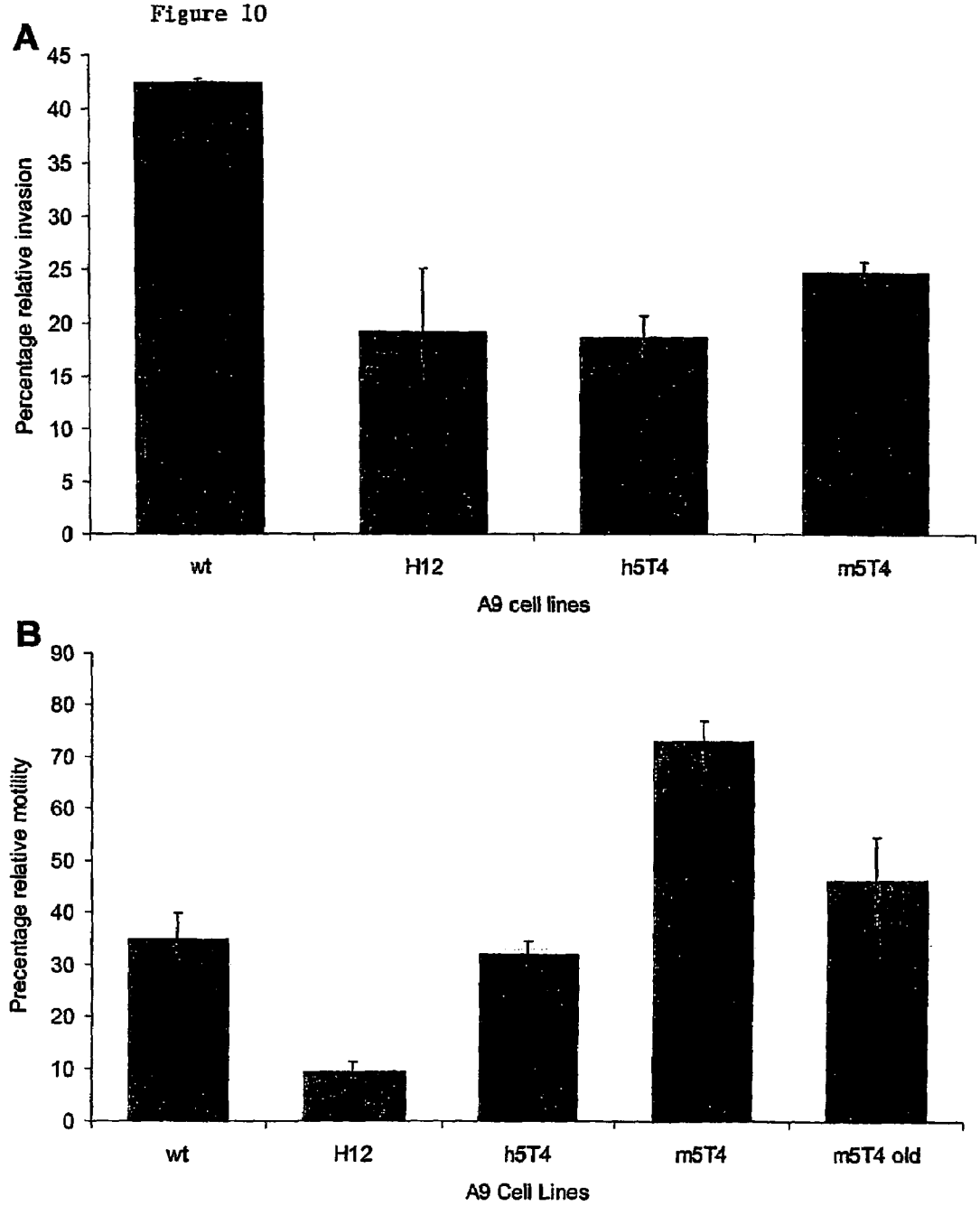

The effect of the stable expression of human and mouse 5T4 molecules on the ability of A9 cells to actively move and invade was compared that of the A9H12 neomycin control cell line. The stable expression of human or mouse 5T4 by A9 cells did not significantly alter their propensity to invade but did increase their motility threefold and sevenfold respectively (FIG. 10). These experiments were repeated three times using cells of low passage number with uniform growth and 5T4 expression. The data presented is representative of these results. Interestingly, cultures of A9-m5T4 positive cells, heterogeneous in their mouse 5T4 expression and older than 25 passages, show reduced motility in comparison to homogeneous cultures of lower passage number.

Immunohistochemistry

Figure 11:
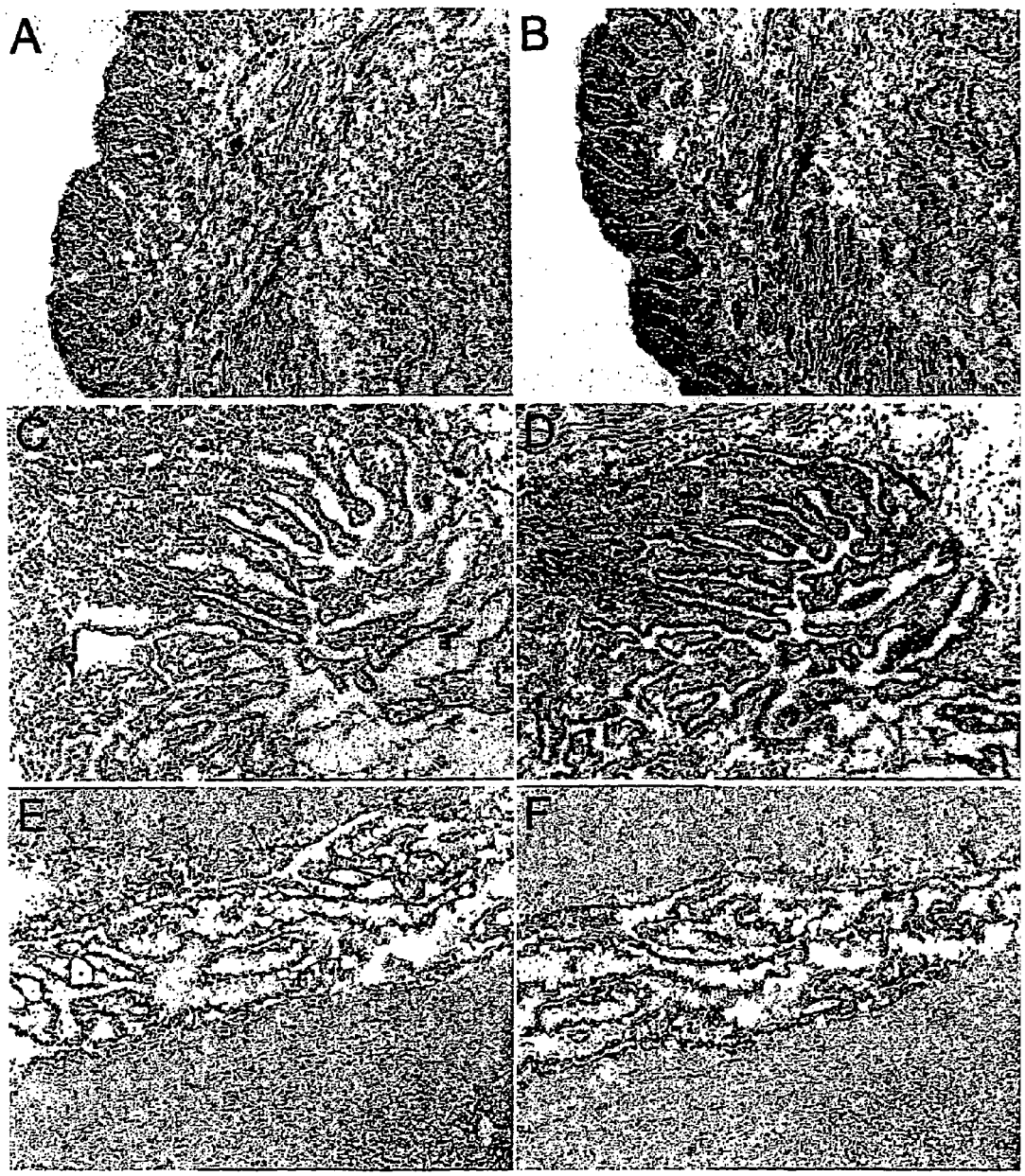

As the human 5T4-oncofoetal antigen was identified in placental tissue, the immunohistochemical reactivity of anti-m5T4 monoclonal antibodies was assessed against frozen sections of 17.5-day mouse placenta (FIG. 11). This showed that the 9A7 antibody specifically labelled placental tissue of foetal origin. Cells of the syncitio- and cytotrophoblast showed discrete staining and the amnion was also positive.

Adult tissues examined were isolated from three individual male and female adult mice. These included heart, lung, liver spleen, kidney, large intestine, small intestine, brain, testes and ovary. Limited staining of specialised subsets of cells was seen in some of these adult tissues. In order of intensity these were; the choroid plexus in the lateral ventricles of the brain (FIG. 11); the outer epithelial lining of the ovary, the glandular mucosal cells of the large and small intestine; the glomeruli of the kidney, the sinusoids of the liver, and the lining of the bronchi.

Adult tissues completely negative for 9A7 staining included the spleen, testis and heart. 9A7 failed to specifically label paraformaldehyde fixed wax embedded mouse placenta. 10

Discussion

The production of m5T4 positive cell lines and the description of m5T4 expression in the adult mouse required the development of a specific rabbit anti-mouse 5T4-Fc polyclonal serum (Rabαm5T4). Previous observations had demonstrated the antigenic integrity of the human 5T4-Fc fusion protein with both mono and polyclonal reagents (Shaw et al (2000)). Therefore, rabbits were immunised with a m5T4-Fc fusion protein and the resultant Rabαm5T4 antiserum was shown to be specific for the m5T4 antigen at the cell surface in B16 F10 and A9 transfected cell lines. However, Rabαm5T4 could not be used for immunohistochemistry due to high levels of background labelling. Therefore, rats were immunised with a vaccinia virus encoding m5T4 antigen and a hybridoma fusion performed, which was then screened by ELISA and flow cytometry against the m5T4-Fc fusion protein and the B16 F10-m5T4 cell line respectively. Screening of this fusion resulted in the isolation of the rat anti-mouse 5T4 antibody 9A7. Here we have demonstrated its specificity for the m5T4 antigen by flow cytometry, ELISA and immunoprecipitation.

The labelling of tumour and transfected cells lines with 9A7 confirmed expression of 5T4 antigen by m5T4 mRNA positive cells (King et al. (1999)). The epitope recognised by 9A7, was shown to possess a conformational component and was mapped to the membrane proximal region of the mouse 5T4 molecule.

Expression of either mouse or human 5T4-cDNA by transfected mouse tumour cell lines increased their motility but reduced their rate of proliferation and capacity to adhere. The magnitude of these effects was shown to be serum concentration dependent and was greater when cells were transfected with autologous 5T4-cDNA.

Finally, the 9A7 antibody was used to describe the distribution of m5T4 in adult mouse tissues by immunohistochemistry. Selection for stable growth and expression of the m5T4 antigen by murine cell lines was relatively difficult. However, the stable expression of human or chimeric 5T4 molecules by these cells was, in comparison, relatively straightforward yielding stable and long-term expression beyond 25 passages. It is possible that over expression of autologous 5T4 molecules may deliver negative effects (e.g. through proliferation rate and adhesion changes), which are more pronounced because of species-specific influences of 5T4 antigen expression.

The specificity of 9A7 for m5T4 was confirmed by direct binding and inhibition based assays in vitro (by ELISA) and at the cell surface where binding of 9A7 to m5T4 mRNA positive cells (King et al. (1999)) could only be inhibited by the m5T4-Fc fusion protein. Western blots of m5T4-Fc fusion protein show that reduction significantly lowers its antigenicity, which implies that the 9A7 epitope, like that of MAb5T4, may be conformational in nature. However, reduced Western blots of h5T4-Fc revealed a cryptic epitope within the human molecule, which can be recognised by 9A7.

As the amino acid sequences of human and murine 5T4 show over 81% identity (Myers et al. (1994)) it is likely that the 9A7 epitope, or one very similar, is present in an altered conformation within h5T4. Reduction, electrophoresis and blotting may allow this cryptic epitope to refold into a conformation that facilitates recognition by 9A7.

Western blot analysis of full-length m5T4 antigen from cell lysates was not very sensitive with 9A7 and required enrichment of membrane glycoproteins by either immunoprecipitation or wheatgerm agglutinin affinity chromatography. Western blots of such enriched cell lysates showed a broad 72 kDa band when probed with the Rabαm5T4 antiserum. These results were similar to those previously demonstrated for human 5T4 (Hole et al. (1990)) and were limited to m5T4 mRNA positive cell lysates (King et al. (1999)). As the Rabαm5T4 antiserum used to probe 9A7 immunoprecipitation reactions also detects the human 5T4 antigen by Western blotting, the lack of a 72 kDa band from h5T4 transfected cell lysates indicates that 9A7 specifically immunoprecipitated the m5T4 antigen.

The 9A7 epitope was mapped to a region of m5T4 spanning the hydrophilic domain to the plasma membrane. The MAb5T4 epitope was also shown to map to this region of human 5T4 and also shows sensitivity to reduction (Shaw et al. (2002), Hole et al. (1990)). Specifically, the 9A7 epitope is mapped to the LRR2 or the C-terminal flanking region (see e.g. Shaw et al. (2002)).

Both m5T4 cDNA transfected and murine tumour derived cell lines exhibited a punctate pattern of labelling with 9A7, which localised to the cell membrane. This pattern was independent of over-expression driven by the CMV immediate early promoter and not induced by antibody mediated re-organisation. However, the disruption of the actin cytoskeleton resulted in the redistribution of 9A7 staining, which is consistent with results reported for human 5T4 antigen (Carsberg et al. (1995)).

Transfection of cells with heterologous 5T4 had a pleiotrophic effect (Carberg et al. (1995); Carsberg et al. (1996)), which was more pronounced upon transfection with autologous 5T4. The morphological, adhesive and proliferative differences between cell lines were clear under low serum conditions but became less apparent at higher FCS concentrations. However, under all FCS concentrations examined the morphology, adhesive capacity and proliferation of the A9 cell lines was always greatest for A9H12 cells followed by A9-h5T4 and then A9-m5T4. Typically, A9H12 cells show the most adhesive morphology with a "pavement" like appearance and many cell-cell contacts (Carsberg et al. (1996)), whilst A9-m5T4 cells show the least adhesive morphology with a spindle like shape and little contact with the growth support. Both the A9-m5T4 and A9-h5T4 cell lines required >0.1% FCS for growth, whereas A9H12 could be grown short term with no FCS when supplemented with transferrin. It is likely that the difference in the ability of these cells to proliferate is linked to their morphology and adhesion to the substratum.

The stable expression of human or mouse 5T4 by A9 cells did not alter their invasive capacity but there is increased motility when compared to control transfected cells. Both the A9 and B16 F10 m5T4 cDNA transfected cell lines show a reduced mean volume after transfection in comparison to neomycin control transfected cells. The human ovarian tumour cell line, Hoc-8, also shows a similar reduction in volume when overexpressing h5T4 (not shown). As the cytoplasmic and transmembrane domains of the human and mouse 5T4 molecules are completely conserved at the amino acid level, it is possible that specific interactions resulting from the extracellular domain of autologous 5T4 molecules may be involved. Mechanisms reported to affect cell volume include, accelerated cell cycle progression (Lemoine et al, (2001)), modulation of the actin cytoskeleton (Moustakas et al. (1998)) and ion channel mediated regulation of cell hydration (Zhande et al. (1996); Scliess et al. (2000)).

The immunohistochemical distribution of m5T4 antigen in the majority of murine adult tissues and 17.5-day placenta, were consistent with those reported for human 5T4 antigen (Ali et al. (2001); Forsberg et al. (2001)). 9A7 recognised both syncitio- and cytotrophobalst in teem murine placental tissue, as well as amnion. The 9A7 antibody was also shown to label discrete subsets of cells within adult murine tissues. The observation of reactivity in the choroid plexus of the lateral ventricals of the brain is novel, as is the above background signal around the sinusoids of the liver, both of which were not seen in the human immunohistochemistry. However, whilst murine brain has been shown to be positive for m5T4 mRNA, no transcripts were detected by Rnase protection in murine (King et al. (1999)).

Here we have characterised m5T4 molecules, their tissue expression and tools (antibodies, tumour cells lines) for pre-clinical mouse models relevant to studies of anti-5T4 directed immunotherapy.

Example 2

Expression of 5T4 in Mouse ES Cells

Cell Culture

ES cells were grown in Knockout DE Invitrogen Corporation, Paisley, UK) supplemented with 15% serum replacement (DMEMSR) (D3, MESC and OKO160; Knockout SR, Invitrogen Corporation, Paisley, UK) or 10% foetal calf serum (DMEMFCS) (129; Invitrogen), sodium bicarbonate (0.12% w/v; Sigma, Dorset, UK) L-glutamine (2 mM, Sigma), nucleosides (6 ml of the following solution/500 ml DMEM: adenosine (80 mg), guanosine (85 mg), cytidine (73 mg), uridine (73 mg) and thymidine (24 mg) dissolved in 100 ml water, Sigma), 2-mercaptoethanol (50 µM; Life Technologies) and LIF (1000 units/ml of ESGRO; Chemicon Int. Middx. UK) at 37° C./5% $CO_2$ unless otherwise stated (Ward et al. 2002b). 129 (a gift from Dr. Wolfgang Breitwieser, PICR; derived from 129/OLA mice), MESC (a gift from Dr. Rhod Elder, PICR; derived from 129/OLA mice) and D3 (American Type Culture Collection (ATCC) CRL-1934; derived from 129/Sv+c/+p mice) ES cell lines were grown on irradiated STO fibroblast feeder layers (ATCC). OKO160 ES cell line (a gift from Dr. Austin Smith, Edinburgh, UK) was grown on gelatin-treated plates in the presence of 200 µg/ml G418 due to targeted integration of LacZ in the Oct-4 locus.

All cell lines were plated at approximately $3\times10^6$ cells per 10 cm dish and split 1:6 every two days. The media was replenished every day. For chimera-forming efficiency experiments, 129 ES cells were grown in DMEMSR on gelatin-treated plates in the presence or absence of LIF. Viable cells were determined by exclusion of trypan blue (Sigma, Dorset, UK; 1:4 dilution in PBS).

Differentiation of ES Cells

ES cells were transferred to gelatin-coated plates for 1 day in the presence of LIF and then replenished with ES media lacking LIF. The medium was changed daily and monolayer cells passaged before confluency. For determination of cell differentiation rates,), MESC and 129 ES cells were plated at $10^5$ cells in a 6 well plate in DMEMSR and LIF in the absence of a feeder layer. There was no significant difference between the plating efficiencies of the two cell lines (data not shown).

Fluorescent Staining of ES Cells

ES cells ($5\times10^5$ cells/well in a 96-well plate) were incubated with rat anti-mouse 5T4 monoclonal (IgG) antibody 9A7 (Woods A M, 2002), rat monoclonal (IgM) antibody to MI/22.25 recognising Forssman antigen (Willison and Stern, 1978) or isotype control antibodies (10 µg/ml in 0.2% BSA/0.1% sodium azide in PBS) for 1 h on ice. Cells were washed 3 times and resuspended in FITC-conjugated rabbit anti-rat Ig for 1 h (1:30 dilution; DAKO, Cambs., UK). Cells were washed twice as descried above, fixed in 1% formaldehyde/PBS solution and cell fluorescence measured in a Becton Dickinson FACScan.

For fluorescent microscopy, 129 ES cells were cultured in DMEMSR+LIF on gelatin-treated plates and differentiated by addition of medium containing FCS known to result in differentiation of the cells. This method rapidly induces differentiation/cell motility within two days. After 48 h, the media was removed, the cells washed twice in PBS and fixed in paraformaldehyde (4% w/v in PBS) for 15 minutes. Cells were rinsed with PBS and blocking buffer (10% v/v rabbit serum, 0.1% Triton X-100 in TBS) added for 20 min at room temp. Cells were then rinsed in TBS and incubated in rat anti-m5T4 mAb 9A7 or isotype control (10 µg/ml in TBS) for 2 hours at room temp. Cells were rinsed 3 times in TBS, and immersed in TBS for 20 min at room temp. Cells were then incubated in rabbit anti-rat FITC conjugate (1:30 in TBS; DAKO, UK) for 1 hr at room temp. Cells were washed a further 3 times and mounted in Vectashield DAPI mounting medium (Vector Laboratories, Peterborough, UK) and viewed using an Olympus BX-51 fluorescent microscope or a Zeiss laser scanning confocal microscope. Images were overlaid using Adobe Photoshop v6.

Expression of EGFP-h5T4 in 129 ES Cells

Cells were grown in DMSR+LIF in the absence of a feeder layer and a sub-confluent plate trypsinised, the cells washed in PBS and resuspended at $1\times10^7$ cells/ml in PBS. 20 µg plasmid DNA was added to 0.5 ml of cell suspension and electroporated at 250V, 475 µF in a BioRad Gene Pulser II. After 24 h one third of the cells were assayed for EGFP expression in a Becton Dickinson FACScan (Becton Dickenson; Oxford, LUK). EGFP positive cells were isolated from the remainder of the sample by FACSVantage SE (Becton Dickenson) and plated out in fresh gelatin treated 9 cm tissue culture dishes. Cellular localisation of EGFP proteins was determined after 48 h using an Olympus BX-51 fluorescent microscope (Olympus, West Midlands, UK). Cell morphology was determined 48 h after transfection using inverted light microscopy.

RT-PCR Analysis

Figure 14A:
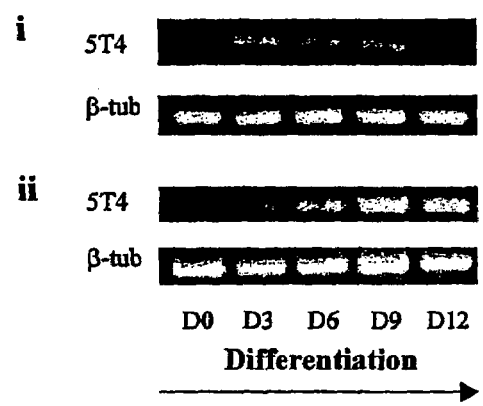
Figure 14B:
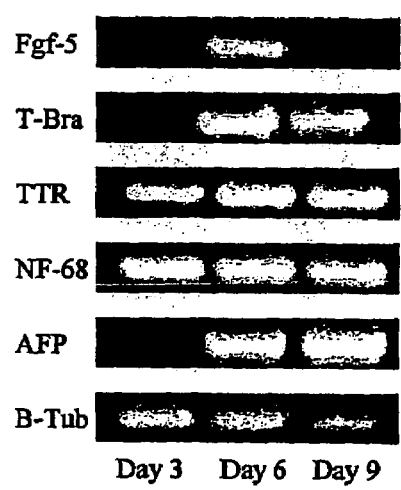

RNA was extracted from cells using RNazol B according to the manufacturer's instructions (Biogenesis, Dorset, UK), treated with DNase (Promega, WI, USA) and phenol/chloroform extracted. Synthesis of cDNA from mRNA transcripts was performed using the following method: RNA (10 µg), dNTP (250 µM), oligo dT (5.0 µg total; Promega, UK), AMV reverse transcriptase (40 units; Promega) in a total volume of 200 µL and incubated at 42° C. for 1 hour. Semi-quantitative RT-PCR of 5T4 was performed using 1 µl of the cDNA solution and 25-30 cycles. RT-PCR was performed using 5 µl of the cDNA solution and 35 cycles. Samples were run on 2% agarose gels containing 400 ng/ml ethidium bromide and visualised on a UV transilluminator. Since the fibroblast feeder layer contains 5T4 transcripts, MESC ES cells were grown for several passages on gelatin-treated plates to remove the fibroblast feeder cells prior to the extraction of RNA (FIG. 14). Primers used were as follows (read 5' to 3'; forward-F, reverse-R): 5T4 F-aactgccgagtctcagatacc (SEQ ID NO:1), R-atgataccccttccatgtgatcc (SEQ ID NO:2), 55° C. annealing temperature, 506 bp; β-tubulin F-tcactgtgcctgaact-tacc(SEQ ID NO:3), R-ggaacatagccgtaaactgc (SEQ ID NO:4), 55° C., 317 bp; Fgf-5 F-ggcagaagtagcgcgacgtt (SEQ ID NO:5), R-tccggttgctcggactgctt (SEQ ID NO:6), 50° C., 537/515 bp (Johansson and Wiles, 1995); Bmp-2 F-gagat-gagtgggaaaacg (SEQ ID NO:7), R-gcagtaaaaggcatgatagc (SEQ ID NO:8), 55° C., 606 bp; ζ-globin F-gatgaagaat-gagagagc (SEQ ID NO:9), R-agtcaggatagaagacagg (SEQ ID NO:10), 55° C., 406 bp; Oct 3/4 F-agaaggagctagaacagtttgc (SEQ ID NO:11), R-cggttacagaaccatactcg (SEQ ID NO: 12), 55° C., 415 bp; Rex-1 F-tgaccctaaagcaagacg (SEQ ID NO:13), R-ataagacaccacagtacacacc (SEQ ID NO:14), 54° C., 414 bp.

Western Blotting

Cells were trypsinised and incubated in tissue culture plates for 30 mins at 37° C./5% $CO_2$ to allow the fibroblast feeder layer to attach to the plate. The cell suspension was removed, washed in PBS and resuspended in lysis buffer ($1\times10^7$ cells/ml in 0.5 M Tris, 1.5 M NaCl, 0.5% v/v NP-40, 0.2 mM phenylmethylsulfonyl fluoride) on ice for 20 min). 20 µl of the lysate was separated by unreduced SDS-PAGE. Positive and negative controls represent cell lysates of A9 cells transfected with either m5T4 cDNA or control vector respectively. Proteins were transferred onto nitrocellulose membrane using the Novoblot semi-dry transfer system (Amersham Pharmacia, Bucks, UK) and the membrane blocked in 5% milk/0.05% Tween/PBS overnight at 4° C. The membrane was probed using rabbit anti-m5T4 polyclonal antibody (Woods et al, 2002) followed by HRP-conjugated sheep anti-rabbit immunoglobulins (DAKO, Cambs, UK) and developed by enhanced chemilumenescence (Amersham Pharmacia, UK). Western blot images were captured using an Epi Chemi II Darkroom and Sensicam imager with quantification determined by Labworks 4 (UVP, CA, USA).

MACS Separation of 5T4-positive MESC ES Cells

MESC ES cells were grown as described above, trypsinised and washed in PBS. 5T4-positive cells were isolated using mAb 9A7 (10 µg/ml), goat anti-rat Ig magnetic beads and MidiMACS LS columns according to the manufacturer's instructions (Miltenyl Biotech, Surrey, UK).

Determining ES Cell Pluripotency by Chimaeric Mouse Formation

129 ES cells were cultured in DMEMSR on gelatin-treated plates in the presence or absence of LIF for 6 days and then trypsinized, suspended in growth medium at $1\times10^7$ cells/ml and incubated with rat anti-mouse SSEA-1 (IgM) antibody conjugated with phycoerythrin or an isotype control antibody (Santa Cruz, Calif.; 1:100 dilution in 0.2% BSA/0.1% sodium azide in PBS) for 15 minutes on ice. Cells were washed 3 times in culture medium and SSEA-1 positive cells isolated by FACS (FACSVantage SE, Becton Dickenson; Oxford, UK). 5T4 expression of the SSEA-1 positive population was determined as described above. Fifteen SSEA-1 positive cells were injected into each 3.5 day old BL/6 blastocysts and implanted into pseudo-pregnant BDF-1 female mice (Hogan B, 1994); glass capillaries from Clark Electromedical Instruments, Kent, UK; Axiovert 10 microscope, Carl Zeiss, Herts, UK; MMO-202ND injection manipulation arm, Narishige Int. Ltd., London, UK; Kopf 750 pipette puller, Tunjunga, Calif.). Pluripotency was determined by chimera formation using donor coat colour. Mice were housed according to Home Office guidelines (1986) and kept on a 12 h-light/dark cycle in which the dark period was from 7 pm to 7 am.

Results

Figure 12A:
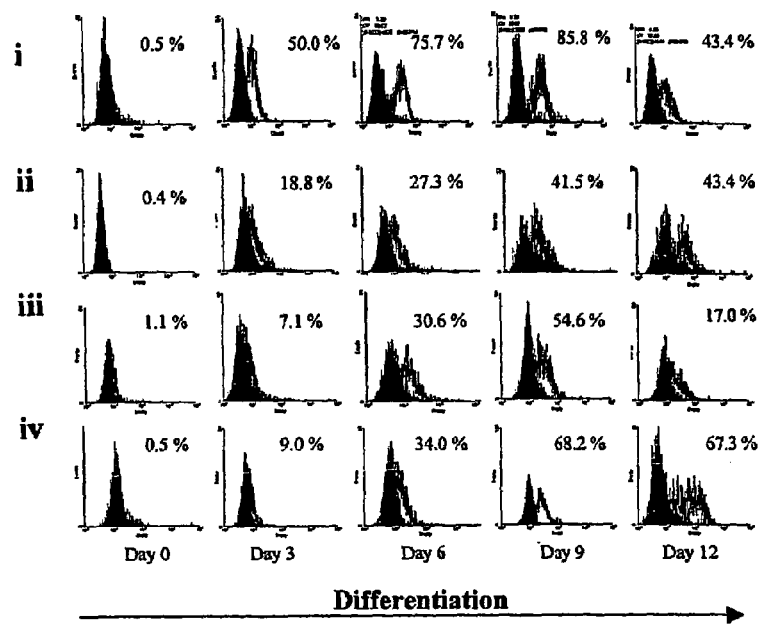
Figure 12B:
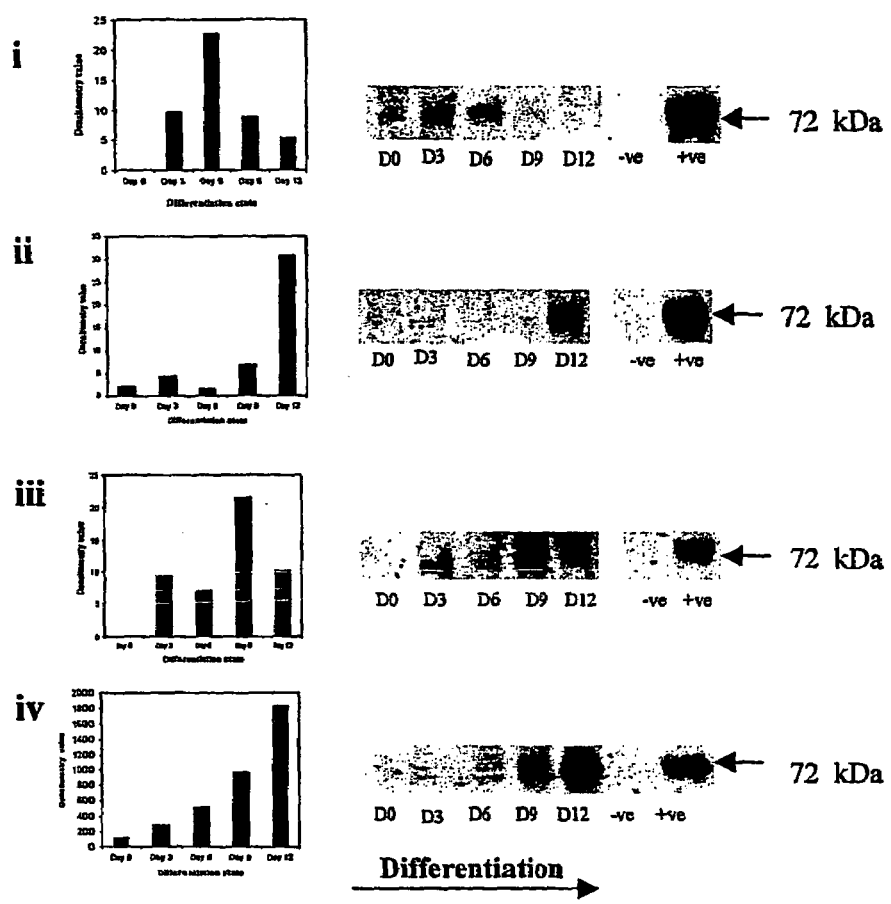

The 5T4 Oncofoetal Antigen and mRNA is Upregulated on ES Cells Following Differentiation Induced by Removal of LIF 5T4 antigen is not detected on the surface of undifferentiated ES cells using mAb 9A7 (FIG. 12a). Following withdrawal of LIF for 3 days the 5T4 antigen is detected on all the ES cell lines, with the percentage of positive cells varying between 7.1% (OKO160) and 50.0% (MESC). Over the 12-day differentiation period there is considerable variation in both the timing of peak 5T4 antigen expression and the proportion of cells labelling positive between the cell lines. For example, MESC ES cell line exhibits peak expression around day 9 with 85.8% of the population positive (FIG. 12a i), whereas D3 ES cells exhibit a steady increase in positive cells which peaks at 43.4% on day 12 (FIG. 12a ii). OKO160 and 129 ES cell lines exhibit similar proportions of positive cells at day 3 (7.1 and 9.0% respectively) and day 6 (30.6 and 34.0% respectively) and both cell lines exhibit peak cell staining at day 9 (54.6 and 68.2% respectively). However the proportion of OKO160 cells staining for 5T4 antigen is decreased significantly by day 12 (from 54.6% to 17.0%) whereas 129 is only slightly reduced (from 68.2 to 67.3%). Increase in total 5T4 protein following removal of LIF was confirmed by western blot analysis of cell lysates using a rabbit anti-m5T4 polyclonal antibody (Woods et al., 2002) (FIG. 12b). Densitometric analysis of the bands shows similar expression patterns compared to cell surface 5T4 expression, and potential 5T4 isoforms are apparent in the 129 and OKO160 ES cell lines FIG. 12b iii and iv respectively).

Figure 13A:
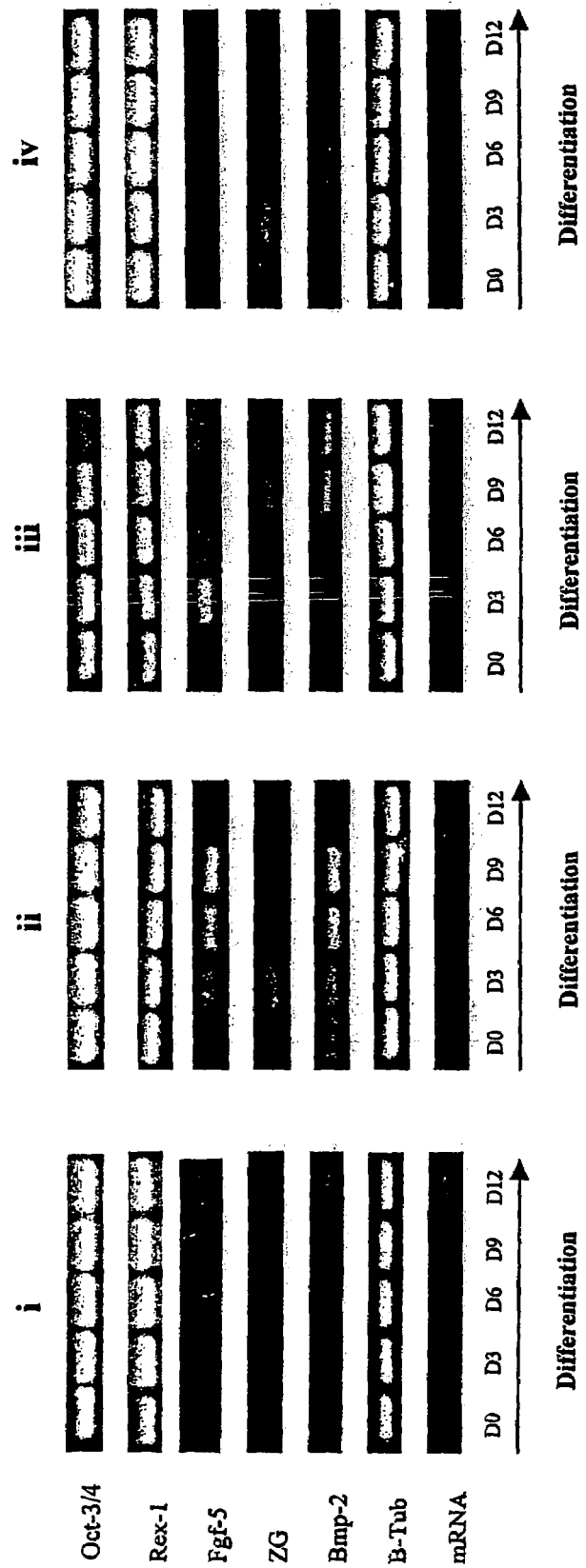
Figure 13B:
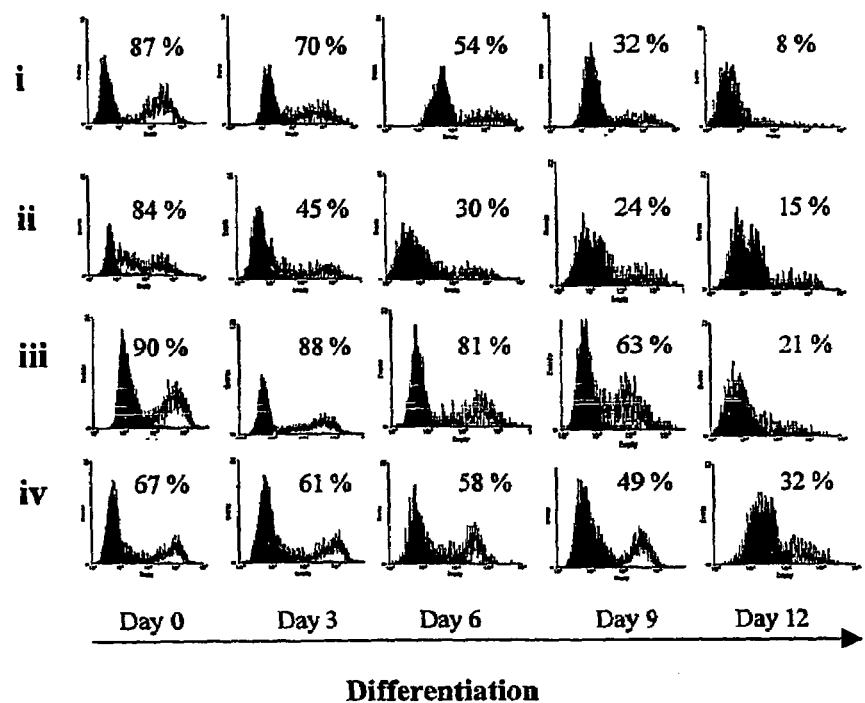

To confirm that upregulation of 5T4 expression upon removal of LIF correlates with differentiation of the ES cell lines we assayed various ES cell-specific (Oct 3/4, Rex-1, Forssman antigen) and differentiation-specific (Fgf-5, ZG and Bmp-2) markers in differentiating ES cells FIG. 13). These results show that upregulation of 5T4 correlates with the detection of transcript differentiation markers (FIG. 13a) and a decrease in the ES cell-specific Forssman antigen (FIG. 13b), confirming that 5T4 is upregulated during the differentiation of ES cells. Most strikingly, the ES cell-associated Oct 3/4 and Rex-1 transcripts do not decrease appreciably in MESC, D3 or 129 ES cells for at least 12 days following removal of LIF (FIG. 13a). These transcripts are commonly used to confirm the presence of undifferentiated ES cells in monolayer culture (Rathjen J, 2002; Rathjen et al., 1999). OKO160 ES cells have a targeted insertion in a single Oct-4 allele, which is likely to account for the relative decrease in Oct-3/4 transcripts in this cell line, although Rex-1 transcripts are still evident 12 days following removal of LIF. There is some disparity between the differentiation markers expressed by the ES cell lines (FIG. 13a). For example, Fgf-5 is transiently detected in all but 129 cells and its peak expression occurs at day 3 in MESC and OKO160 but at day 9 in D3 ES cells. Additionally, ZG is transiently detected in all but MESC cells. Peak expression occurs at day 3 in D3 and 129 ES cells but at day 9 in OKO160 cell lines.

In MESC and D3 cell lines the peak Forssman antigen (FA) expression is observed in undifferentiated ES cells and decreases upon removal of LIF (FIG. 13b). However, over the 12-day differentiation period there is considerable variation in the expression of the Forssman antigen. For example, at 9 days following removal of LIF all ES cell lines exhibit a proportion of cells expressing the antigen. OKO160 and 129 ES cells exhibit FA staining at day 9 that is only slightly lower than that present on undifferentiated cells. However, at 12 days following removal of LIF the majority of the cell populations are negative for FA, although D3, OKO160 and 129 ES cells exhibit a small proportion of positive cells. The differences in FA expression between the cell lines may be a result of clonal variation or could reflect differential activity of specific glycosylating enzymes required for the glycolipid expression. This data shows that the use of FA as a marker of undifferentiated ES cells is limited due to the prolonged expression of the antigen following removal of LIF in monolayer culture.

The increase in 5T4 antigen on ES cells upon removal of LIF is associated with increased 5T4 mRNA (FIG. 14a), probably reflecting transcriptional upregulation of 5T4. The maximal level of 5T4 transcript in MESC ES cells (FIG. 14a i) occurs at day 3, which precedes the maximal level of protein expression (Day 6/9; FIG. 12a i). The maximal expression of transcripts in OKO160 cells occurs at day 9 (FIG. 14a ii), which corresponds with maximal protein expression FIG. 12a iii). There is a clear reduction in transcripts in MESC and OKO160 cell lines after maximum protein expression. 5T4 transcripts are detected in undifferentiated OKO160 and MESC ES cells by RT-PCR analysis (45 cycles; data not shown), perhaps due to spontaneously differentiating cells within the population expressing 5T4 mRNA or low levels of transcripts within undifferentiated cells.

ES cells produce differentiated cells corresponding with cell types representative of the primary germ layers, endoderm, mesoderm and ectoderm (Smith, 2001). To determine whether 5T4 is expressed on cells derived from the three germ layers, MESC ES cells were assayed for the presence of germ layer-specific transcripts following isolation of the 5T4-positive population (FIG. 14b; Table 3). The detection of transcripts for AFP, TTR, NF-68, Fgf-5, and T-Bra in the 5T4-positive cell population demonstrates the presence of a proportion of visceral endoderm, endoderm, ectoderm, primitive ectoderm and mesoderm cell lineages respectively.

Figure 15:
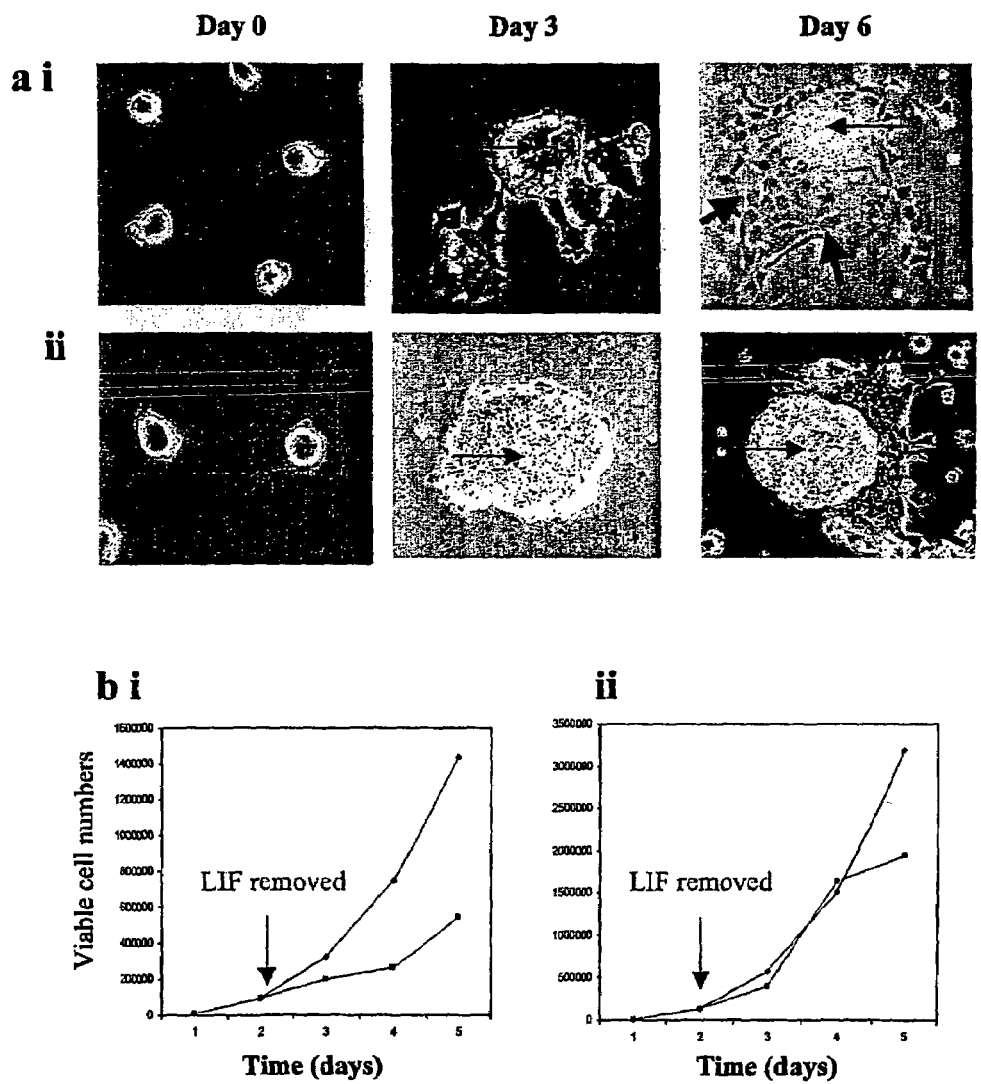

Kinetics of 5T4 Expression Correlates with the Differentiation Rate of ES Cell Lines With differentiation, DISC show rapid kinetics of 5T4 expression compared to the 129 ES cells (FIG. 12a). This is consistent with the relative proportions of FM positive cells remaining after 12 days of differentiation (FIG. 13b). When ES cells differentiate there is a reduction in the proliferation and increase in apoptosis in the population. As determined by cell numbers in the presence or absence of LIF, MESC proliferation was clearly reduced after one day following removal of LIF whereas 129 ES cells showed no significant change (FIG. 15b i and ii respectively). Thus, the rate of proliferation is correlated with the induction of 5T4 expression. In addition, when ES colonies are subject to LIF withdrawal, the outer cells show altered morphology and motility (FIG. 15a). The appearance of such early differentiating cells was more rapid in the MESC than in 129 ES cells. Thus, at three days following removal of LIF, a significant proportion of MESC ES cell colonies exhibited differentiated cells (large arrows) whereas 129 ES cells maintained characteristic ES cell colony morphology (small arrows). By day 6, both ES cell lines exhibited differentiated cells although the numbers were more numerous in the MESC cell line. In contrast, to the LIF dependence of MESC, 129 ES cell numbers were not decreased until 3 days following removal of LIF, suggesting a delayed differentiation rate of these cells.

Immunofluorescent analysis of 5T4 expression in undifferentiated and differentiated 129 ES cells show that 5T4 is associated with both colony-associated and migrating cells (FIG. 16a-c and f-h). This is consistent with evidence that expression of 5T4 molecules can influence the morphology and motility of cells in vitro and suggests a mechanistic involvement in the early differentiation process. A significant proportion of the protein appears to be cytoplasmic which may reflect recent induction of 5T4 protein following differentiation of the cells. Cell-surface 5T4 is clearly present, as demonstrated by the FACS profile of the differentiated cell population FIG. 16e; 24.0% positive cells compared to 0.5%).

Expression of EGFP-h5T4 in Undifferentiated ES Cells Alters Colony Morphology

Figure 17:
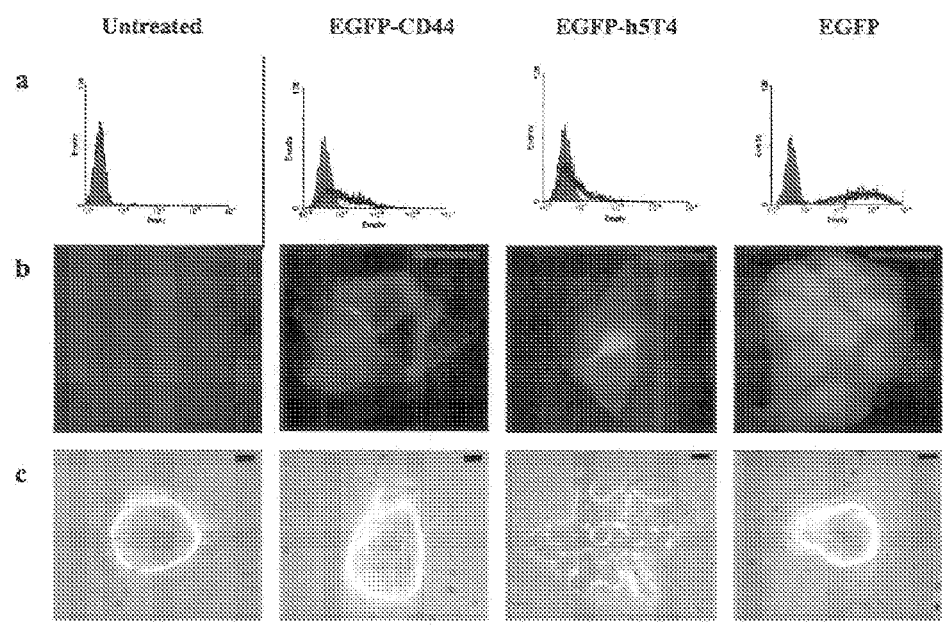

To further investigate the influence of 5T4 expression on ES cells, 129 ES cells were transfected with EGFP, EGFP-h5T4 or EGFP-CD44 plasmids and EGFP-positive cells isolated by FACS (FIG. 17). In the unsorted populations, the proportion and intensity of EGFP expression was lower for EGFP-h5T4 and EGFP-CD44 compared to EGFP alone (FIG. 17a). As expected, both EGFP-CD44 and EGFP-h5T4 located to the cell membrane and the majority of EGFP to the nucleus (FIG. 17b). EGFP-h5T4 transfected cells also exhibited areas of intense intracellular fluorescence that are likely to be Golgi-associated (FIG. 17b). Morphological studies showed that ES cells expressing EGFP-h5T4 resulted in increased cell spread compared to the cell surface protein control EGFP-CD44 and EGFP alone (FIG. 17c). Both EGFP-CD44 and EGFP expressing cells maintained characteristic colony morphologies that were similar to untreated ES cells. These results show that expression of 5T4 in differentiating mouse ES cells is implicated in the spread and movement of the cells away from the primary colony.

The differences between the cell-surface EGFP-h5T4 localisation in FIG. 17b and the prominent cytoplasmic 5T4 staining in FIG. 5a-c is likely to be due to the use of the CMV promoter in the former. CMV is known to be highly efficient in undifferentiated ES cells (Ward C M, 2002a), therefore, significant levels of membrane-associated 5T4 would be expected. In contrast, FIG. 16 demonstrates the localisation of m5T4 protein shortly after induction under its natural promoter, and we would expect both cytoplasmic and cell surface 5T4 to be present.

Figure 18:
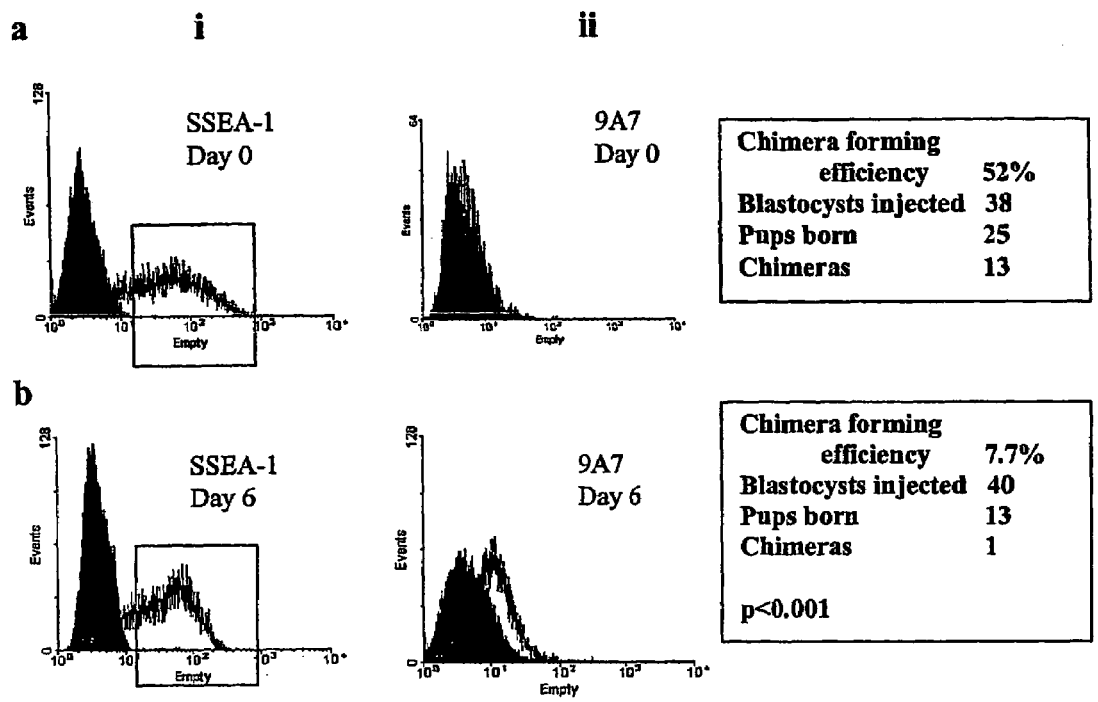

Absence of 5T4 is a Measure of Mouse ES Cell Pluripotency and Allows Optimisation of ES Cell Growth Conditions We determined whether 5T4 expression is a useful indicator of lack of pluripotency in mouse ES cells following removal of LIF compared to the ES cell marker SSEA-1 (FIG. 18). Undifferentiated 129 ES cells were sorted for SSEA-1 expression (boxed population in FIG. 18a i) and were found to be 5T4 negative (FIG. 18a ii). The pluripotency of this SSEA-1+/5T4− population was found to be 52%, as determined by the chimera forming efficiency of the cells following injection into mouse blastocysts and reinplantation into foster mothers (Percentage coat colour of chimeric mice was 1×60%, 4×25%, 2×20%, 2×10% and 4×<5%). Following removal of LIF from the culture for 6 days, a significant proportion of the cells remained positive for SSEA-1 (FIG. 18b i) and these cells were found to be 5T4 positive (FIG. 18b ii). This SSEA-1+/5T4+ cell population exhibited only 7.7% pluripotency ($p<0.001$ compared to SSEA-1+/5T4− population; percentage coat colour of chimeric mice was 1×<5%). Furthermore, fewer mice were born in the SSEA-1+/5T4+ cell population compared to SSEA-1+/5T4− cells (32.5% and 66% respectively), suggesting differentiated ES cells may be detrimental to the development process. These results demonstrate that absence of 5T4 from an ES cell population is a more accurate and sensitive indicator of pluripotency than the commonly used ES cell marker SSEA-1.

Many ES cell techniques utilise cloning and expansion of early passage cell lines. Therefore we assayed the effects of cloning and extended passage on the expression of the 5T4 antigen to assess its suitability as a marker for optimisation of these cells prior to use in such techniques. Undifferentiated MESC ES cells did not express cell surface 5T4 antigen following culture for 12 passages. Similarly, cloned 129 ES cell colonies lacked cell surface antigen following isolation and expanded growth. Removal of 129 ES cells from a fibroblast feeder layer and subsequent passage on gelatin-treated plates also had no effect on 5T4 antigen expression (using DMEMSR+LIF. FIG. 18a ii). All cloned and extended passage cells exhibited a characteristic increase in cell surface 5T4 following removal of LIF from the cells, as described in FIG. 12a.

Figure 16:
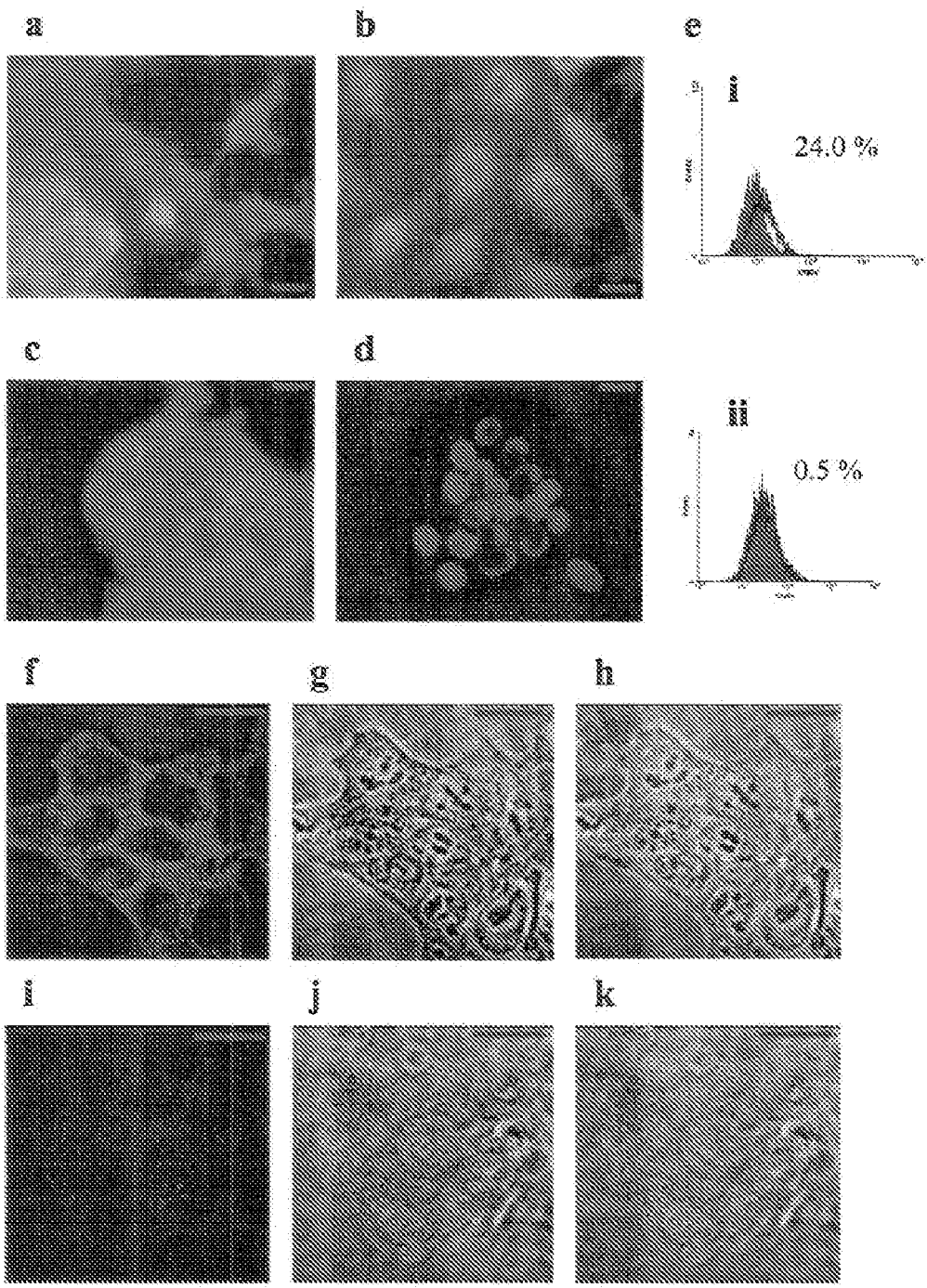

The quality of serum used for the growth of ES cells is known to affect the differentiation state of the cells, even in the presence of LIF (Smith, 1992). Growth of 129 ES cells in medium comprising serum in which the cells exhibit low cloning efficiency resulted in altered colony morphology, increased cell differentiation and induction of 5T4 expression compared to cells cultured in normal serum (FIG. 16). We have also observed some primary embryonic fibroblast (PEF) feeder layer batches that induce expression of 5T4 on ES cells when co-cultured, suggesting that these PEF batches are not optimal for ES cell growth. The reason for the inability of some PEF batches to sustain ES cells in an undifferentiated state is probably due to harsh passaging (1:10) compared to batches able to maintain undifferentiated cells (passaged 1:3). Thus, the absence of 5T4 from ES cells is a useful marker of serum and PEF quality for the undifferentiated growth of these cells.

Discussion

This is the first report of a cell surface marker of ES cell pluripotency that is positively regulated following differentiation of the cells. As proof of principle, we show that 5T4 is a more useful pluripotency marker than SSEA-1 following differentiation of cells by removal of LIF. This may allow isolation of very early differentiated cells enabling elucidation of events associated with early ES cell differentiation. We also demonstrate that kinetics of 5T4 expression correlate with the differentiation rate of ES cells, and we show that these rates are varied between ES cell lines. Expression of 5T4 also correlates with the appearance of motile cells, and expression of EGFP-h5T4 in undifferentiated ES cells leads to increased cell spread. These results suggest that 5T4 is involved in cell motility and/or decreased cell-cell contacts during the early differentiation of ES cells. It further implies an active role for 5T4 during the metastatic process and suggests that differentiating mouse ES cells may be useful for studying events associated with this process.

Traditionally, markers of ES cell pluripotency are negatively regulated. They are expressed at high levels in undifferentiated ES cells and decrease following the differentiation (Ben-Shushan et al., 1998; Ling and Neben, 1997; Niwa et al., 2000; Rathjen J, 2002). However, because these markers are expressed on a significant proportion of cells following removal of LIF they are not optimal for accurately determining pluripotency under these conditions. We have demonstrated that the ES cell markers SSEA-1, Oct-4 and Rex-1 (Ben-Shushan et al., 1998; Fan Y, 1999; Niwa et al., 2000; Rathjen J, 2002; Rathjen et al., 1999) can be detected in ES cell populations for at least 12 days following removal of LIF. This is likely to be due to the inefficient differentiation of ES cells in monolayer culture under these conditions. Thus, the kinetics of loss of expression of SSEA-1, Oct-4 or Rex-1 in a differentiating ES cell population does not provide for a useful measure of the pluripotency or undifferentiated state of the cells. In contrast, 5T4 is positively regulated and can rapidly determine the differentiation state, therefore its absence determines the pluripotency of an ES cell population. Indeed, we have demonstrated that lack of cell surface 5T4 on ES cells is a more accurate indicator of pluripotency than SSEA-1, with SSEA1+/5T4+ ES cells showing significantly decreased chimera forming efficiency.

5T4 antigen is the first cell surface marker that is able to determine both the pluripotency and early differentiation state of an ES cell population in a single, non-destructive assay. Cell surface 5T4 antigen is also upregulated on cells differentiated as embryoid bodies or following addition of retinoic acid and removal of LIF in monolayer cultures (FIG. 31). Thus, 5T4 is a useful marker of differentiation for a range of ES cell techniques. As such, the application of 5T4 as a differentiation marker of ES cells is most valuable for maintaining an undifferentiated pluripotent population and for establishing optimal growth conditions for the cells.

5T4 is unique in that it is both expressed for a relatively prolonged period of time and is present on cells derived from each of the three germ layers. The correlation of 5T4 expression kinetics with the differentiation rate of ES cells is an interesting observation that may enable detailed study of the factors involved in the differentiation process. The mechanisms for this correlation are likely to reflect motility of the differentiated cells away from a primary colony. The results demonstrate that there are considerable differences between the ES cell lines studied, both in motility and reliance on LIF for cell proliferation.

Furthermore, the transcript expression patterns in differentiating ES cells can be different. However, culture conditions or clonal variation within populations may account for this difference since the cell lines in this study were not cloned or grown under identical conditions.

5T4 is a member of the LRR family, which contains approximately 60 members with no obvious common function (Kobe B, 1994; Kobe B, 1995), and it is likely that the LRR domains of 5T4 provide a scaffold for a variety of biological functions (Shaw D M, 2002). Overexpression of 5T4 can have marked effects on both the actin cytoskeleton and motility of cells (Carsberg et al., 1995; Carsberg et al., 1996; Woods et al., 2002), and it has been shown that the extracellular domain affects cell motility. The observations that EGFP-h5T4 leads to increased motility/spread of ES cells and that 5T4 expression correlates with the appearance of motile cells suggests a motility role for 5T4 during ES cell differentiation. Interestingly, the EGFP-h5T4 construct obviates any role for the terminal cytoplasmic SDV motif of h5T4, which has been shown to bind through the PDZ domain of TIP-2/GIPC. TIP-2/GIPC is known to interact with the cytoskeleton through $\alpha$-actinin which may explain the cytoskeletal rearrangement phenotype observed when 5T4 is expressed (Awan et al, 2002). There are likely to be additional mechanisms whereby 5T4 expression can alter the morphology as well as the motility of cells (Carsberg et al 1995) and these may be of functional significance in development and carcinogenesis.

Example 3

Human Pluripotent Embryonic Cells Show Similar Properties to Murine ES Cells for 5T4 Oncofoetal Antigen Expression.

1) Human multipotent GCT (germ cell tumour) 27 and 35 cell lines (Pera et al., Int J Cancer 40: 334-343, 1987; Pera et al., Differentiation 39: 139-149, 1988) were grown under conditions which limit the differentiation of the embryonal carcinoma stem cell type by growth on primary embryo fibroblasts. Differentiation was induced by growth without feeders on gelatin treated plates.

Methods: Falcon 9 cm tissue culture dishes were coated with 5 ml 0.1% gelatin for 1 h at 37 C. A vial of 129 irradiated (8000 rads) primary embryo fibroblasts (pees) ($4\times10^6$) were removed from liquid nitrogen and resuspended in 10 ml of Pef media (Dulbecco's Modified Eagles Medium (DMEM) 2 mM glutamine, 10% FCS). The gelatin was removed, 10 ml of pefs added to the dish and incubated overnight at 37° C. in humidified 5% $CO_2$. Before adding GCT cells, the media was changed to Hes media (DMEM, 2 mM glutamine, 20% Hyclone defined fetal bovine serum; 90 μM 2β-mercaptoethanol; 1% Gibco non-essential amino acid (NEAA) and Insulin, Transferrin and Selinium (ITS) supplement). The medium was changed daily and cells passaged before confluence. Cells were washed twice with PBS and then treated with 3 ml trypsin-EDTA (Sigma) for 30 seconds, this was removed and the cells incubated for 1 min at 37° C. The cells were harvested in Hes medium and split 1/10 maintained in exponential growth, usually every third day. Differentiation was induced by plating on to gelatin treated plates and Hes medium with unselected FCS changed every other day.

5T4 expression was assessed on cell suspensions harvested as above and washed twice in PBS. Cells at $2\times10^6$ cells/ml were added at 100 μl/well of a 96 well plate and spun at 1000 RPM for 5 mins at 4° C. The supernatant was removed, 100 μl monoclonal antibody to human 5T4 antigen at 1 μg/ml or IgG1 isotype control added in FACS buffer (0.2% BSA, 0.1% sodium Azide in PBS) and incubated on ice in dark for 1 h. Following three washes in FACS buffer, anti-mouse Ig-FITC second layer antibody was added and incubated on ice in dark for 45 min. The cells were washed three times and fixed in 100 μl 4% formaldehyde in PBS before analysis on Becton Dickinson FACSCAN.

Figure 20:
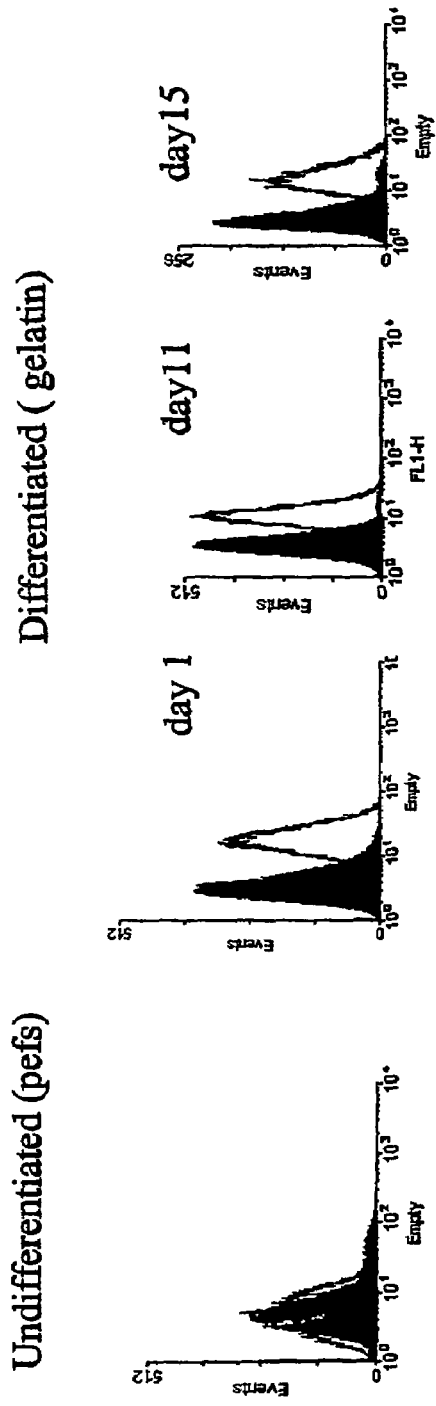
Figure 21:
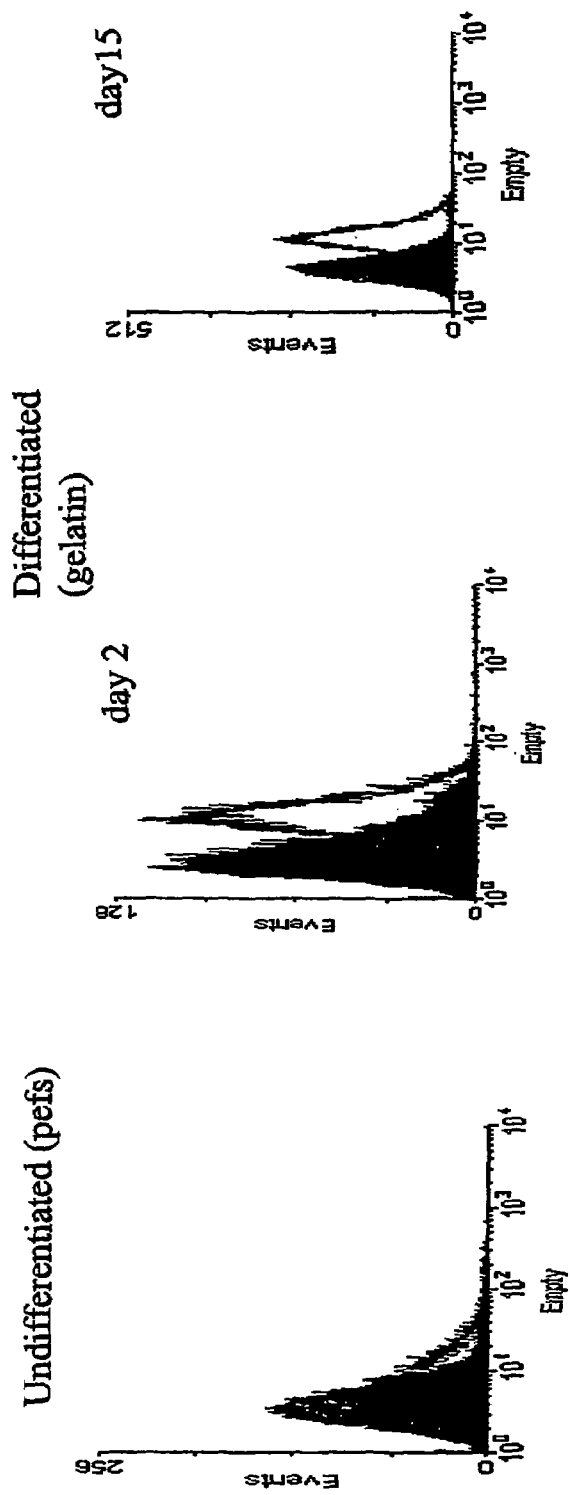

Results: FIG. 19 shows that mouse primary embryo fibroblasts do not react with the human 5T4 specific mAb (filled and open areas: control Ab and mAb 5T4 respectively). Tera 2 clone 13 cells (Thompson et al., J. Cell Sci. 72: 37-64 1984) are embryonal carcinoma cells with some limited potency that have been adapted to growth on gelatin coated tissue culture plates. FACs analysis shows that they are strongly 5T4 positive. By contras the embryonal carcinoma stem cells of the pluripotential GCT 27 and GCT 35 lines are 5T4 negative when grown on pefs but rapidly upregulate their 5T4 surface expression when grown on gelatin coated plates (FIGS. 20 and 21).

Conclusion 5T4 surface expression is negatively associated with optimised undifferentiated culture conditions of germ cell tumour derived embryonal carcinoma cells. In the absence of such conditions the cells will lose their pluripotent phenotype (differentiate) and this is associated with 5T4 expression.

2) Human embryonic stem (ES) cells (Reubinoff et al, Nature Biotechnology 18:399-404, 2000; ES Cell International) were grown under conditions which limit the differentiation of the ES cell type by growth on primary embryo fibroblasts. Differentiation was induced by growth without feeders on fibronectin treated plates. The expression of OCT-4 transcription factor was determined as an established marker of pluripotent embryonic stem cells (Rathjen et al., J. Cell Sci 112: 601-12, 1999; Rossant, Stem Cells 19: 477-82, 2001).

Methods: Ten Falcon organ culture plates were coated with 0.1% gelatin for 1 h at 37° C. Irradiated pefs ($1.75 \times 10^6$) were resuspended in 10 ml of pef media and 1 ml added to each plate. The outer reservoir was filled with 4 ml of sterile distilled water and the cells incubated overnight at 37° C. Before adding ES cells, the media was changed to Hes media. ES cells were grown and passaged essentially as described previously but without dipase treatment (Reubinoff et al 2000). ES colonies were cut under the microscope using a pulled capillary tube, divided into several pieces and plated on fresh feeder plates. The Hes medium was changed daily and homogenous ES morphology colonies (FIG. 22a) chosen for passage about every seven days. Some colonies are clearly distinct with evidence of heterogeneity in morphological types and further differentiation is evident if the cells are plated without feeders on fibronectin coated Falcon chamber slide flasks (5 µg/ml overnight at 4° C.) (FIG. 22b). FACS analyses were performed with cell suspensions obtained from pooled dissected colonies (20-30) by trypsin-EDTA treatment (5 min at room temperature followed by gentle agitation after adding Hes medium). In situ expression of 5T4 and OCT 4 was performed on fixed cells. Briefly, cells grown on Falcon culture chamber slides were washed with PBS, treated with 4% paraformaldehyde in PBS for 15 mins and washed again with PBS. Non-specific binding was blocked by incubation with filtered 0.1% BSA, 1% Goat serum, 0.1% Triton-X100 in PBS. Primary antibodies, mouse IgG1 mAb human 5T4 (1 µg/ml), mouse IgG2b to human OCT-4 (2 µg/ml; SC-5279, Santa Cruz, Calif.) and isotype control (Biogenesis, UK) were diluted in blocking buffer and incubated with the cells at room temperature for 2 hours. The slides were then carefully washed for 5 minutes 4 times in PBS. Second layer anti-mouse Ig reagents conjugated with Alexafluor 546 or 488 to detect OCT-4 and 5T4 expression respectively were diluted in blocking buffer and incubated with the cells for 1 hour at RT. Careful washes in PBS for 2×5 mins, 1×15 mins and 2×5 mins were performed before adding a small drop of Dapi Vector Shield and cover slipping. The cells were viewed on an Olympus BX 51 fluorescence microscope and a Zeiss Laser Scanning Confocal Microscope. Images were overlaid using Adobe Photoshop version 6.0.

Figure 23:
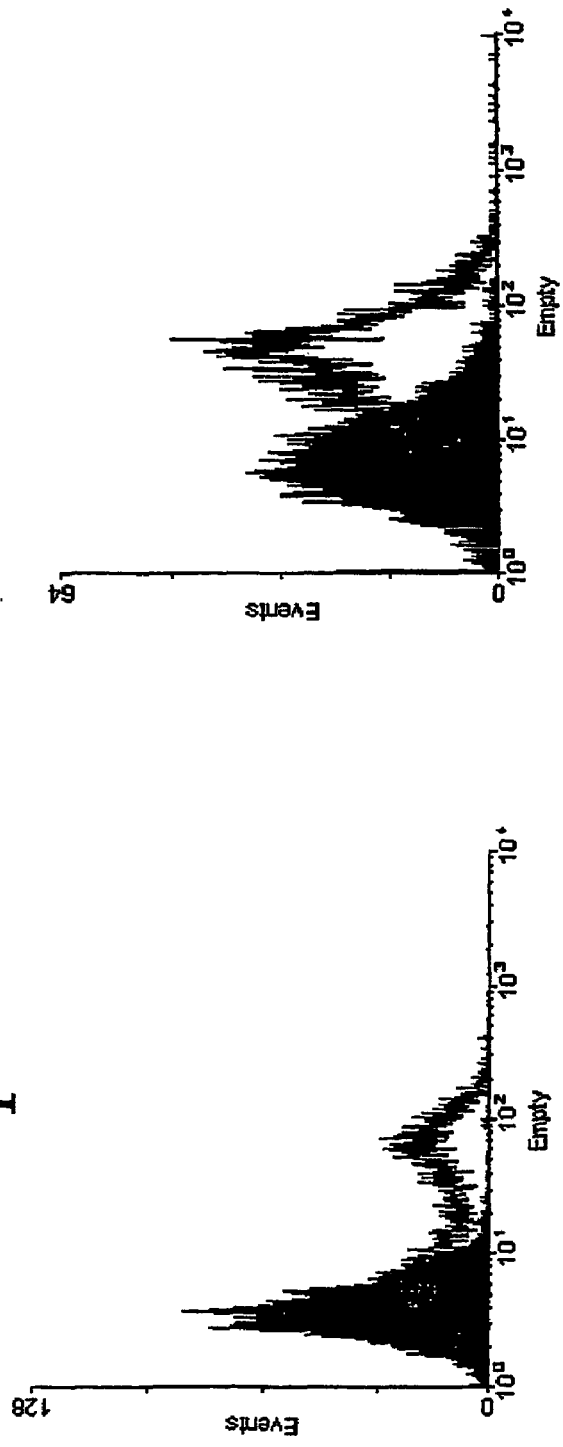
FIG. 23 shows FACS analysis of 5T4 expression of cells from "undifferentiated" ES cell colonies and ES cells plated on fibronectin coated dishes.
Figure 24:
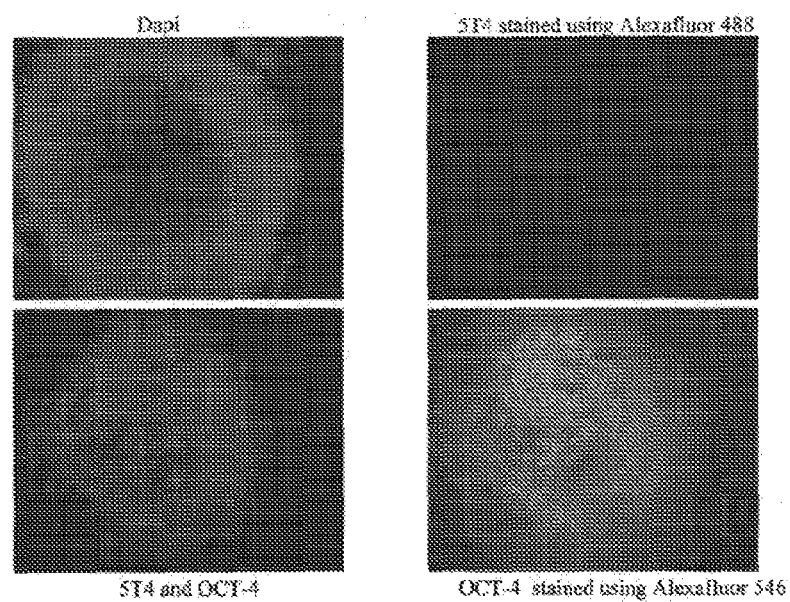
Figure 25:
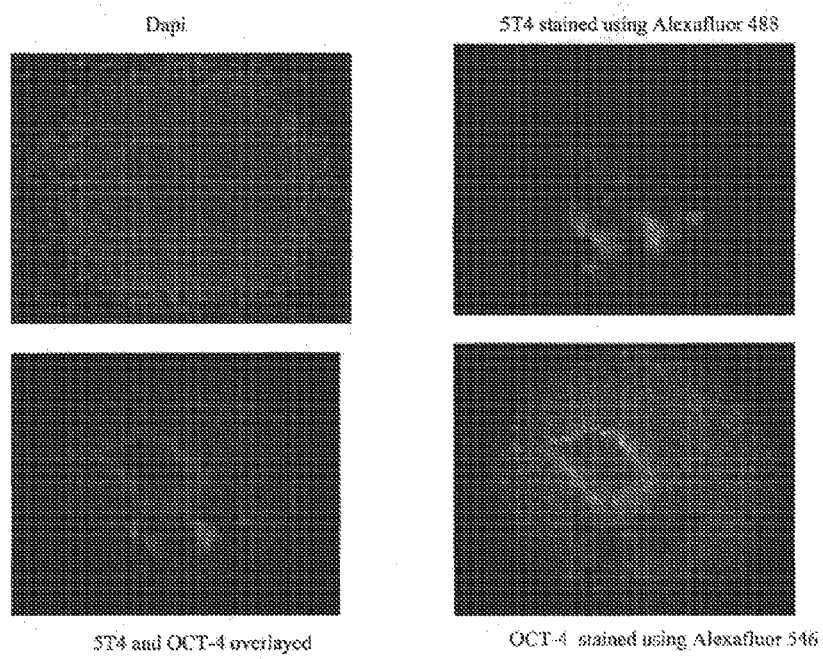
Figure 26:
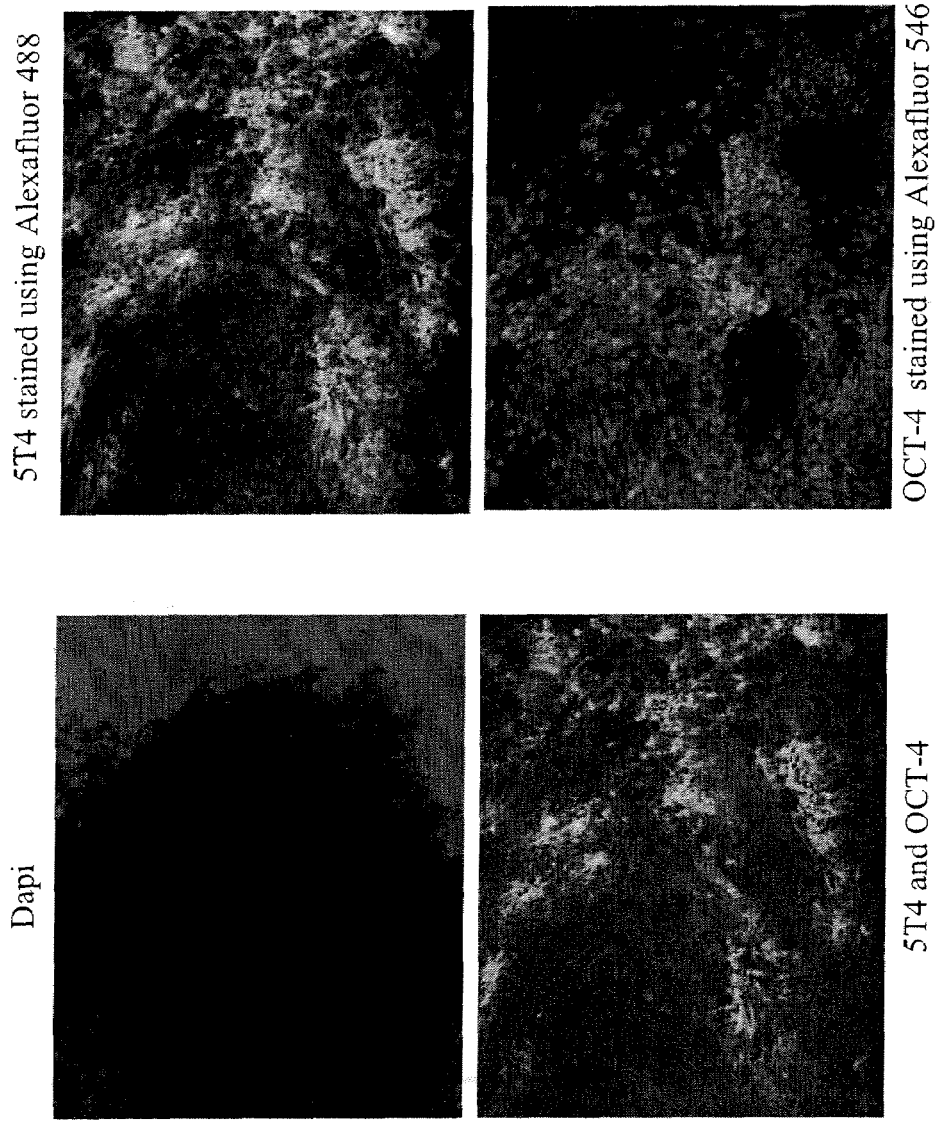
Figure 27:
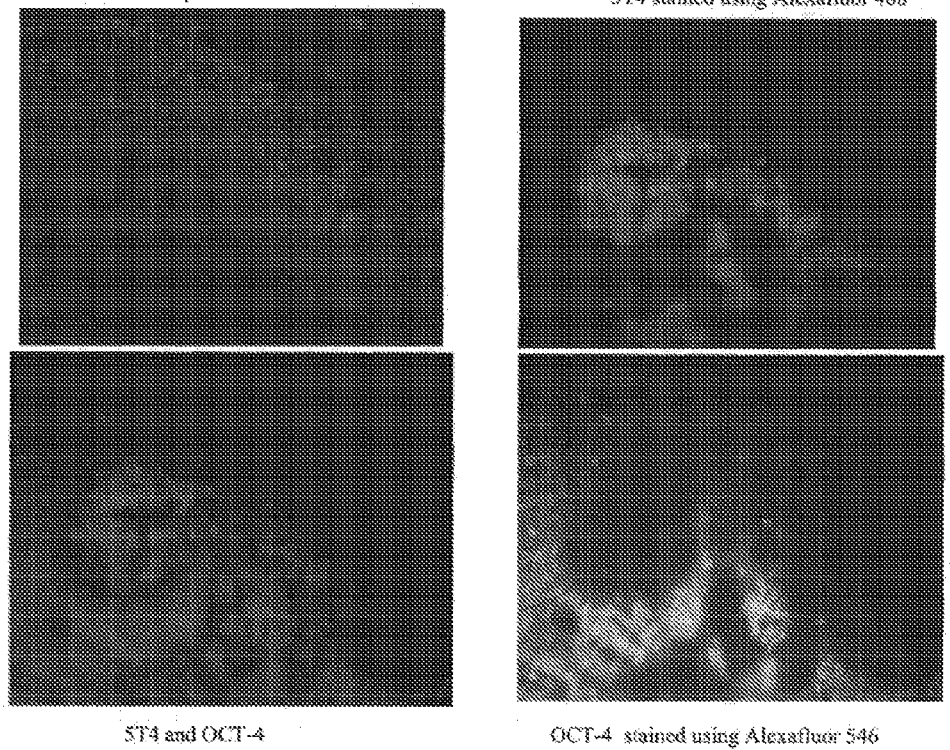

Results: FIG. 23a shows that ES cells from colonies harvested from growth on pefs have two distinct populations of 5T4 labelled cells. This is consistent with pluripotential ES cells being 5T4 negative and early differentiating populations becoming 5T4 positive. This is supported by absence of a 5T4 negative population in cells grown under conditions that fail to prevent ES differentiation (FIG. 23b). In situ immunofluorence analysis of both OCT-4 and 5T4 expression in ES colonies grown on pefs clearly demonstrates that loss of the pluripotent intracellular OCT-4 expression is congruent with expression of human 5T4 (FIG. 24-27). Further analysis of areas of morphologically differentiated cells shows clear evidence of cell surface expression by confocal microscopy FIG. 28).

Conclusion: Human 5T4 expression is negatively associated with pluripotent human ES cells that express OCT-4. Loss of the latter is accompanied by up regulation of cell surface 5T4 expression on the differentiating cell populations.

Example 4

Additional Murine Studies

We have generated murine ES clones (from E14TG2a ES line) where the LacZ gene has been knocked in downstream of the 5T4 promoter. The construct used for homologous recombination is depicted in FIG. 29. The KO 5T4 cells show induction of LacZ expression under differentiating culture conditions detected by using a X-Gal staining kit (Gene Therapy Systems Inc, California (FIG. 30). ES cells on pefs have very few X-Gal stained cells whereas in differentiating cells grown without feeders and LIF there are areas of strong staining. Thus reporter genes controlled by the 5T4 promoter sequences can be used as indicators of desired or undesired ES differentiation.

REFERENCES

Abe K, N. H., Iwase K, Takiguchi M, Mori M, Abe S I, Abe K, Yamamura K I. (1996). *Exp Cell Res* 229, 27-34.
Ali, A., Langdon, J., Stern, P. and Partridge, M. (2001) Oral Oncol 37, 57-64.
Awan A, L. M., Shaw D M, Sheppard F, Westwater C, Lyons S A, Stern P L. (2002). *Biochem Biophys Res Commun.* 290, 1030-6.
Ben-Shushan, E., Thompson, J. R., Gudas, L. J. and Bergman, Y. (1998). *Mol Cell Biol* 18, 1866-78.
Bielinska, M., Narita, N., Heikinheimo, M., Porter, S. B. and Wilson, D. B. (1996). *Blood* 88, 3720-30.
Bradford, M. M. (1976) Anal Biochem 72,248-54.
Brook, F. A. and Gardner, R. L. (1997). *Proc Natl Acad Sci USA* 94, 5709-12.
Carroll, M. W., Overwijk, W. W., Surman, D. R, Tsung, K., Moss, B. and Restifo, N. P. (1998) J Natl Cancer Inst 90, 1881-7.
Carsberg, C. J., Myers, K. A. and Stern, P. L. (1996) Int J Cancer 68, 84-92.
Carsberg, C. J., Myers, K. A., Evans, G. S., Allen, T. D. and Stern, P. L. (1995). *J Cell Sci* 108, 2905-16.
Chakrabarti, S., Sisler, J. R. and Moss, B. (1997) Biotechniques 23, 1094-7.
Earl, P., Wyatt, L., Cooper, B., Moss, B. and Carroll, M. (1998) in Current Protocols in Molecular Biology, pp. 16.16.1-13, John Wiley & Sons
Fan Y, M. M., Chaillet J R. (1999). *Dev Biol.* 210, 481-96.
Forsberg, G., Ohlsson, L., Brodin, T., Bjork, P., Lando, P. A., Shaw, D., Stern, P. L. and Dohlsten, M. (2001) Br J Cancer 85, 129-36.
Hirashima, M., Kataoka, H., Nishikawa, S. and Matsuyoshi, N. (1999). *Blood* 93, 1253-63.
Hogan B, B. R., Constantini F and Lacy E. (1994). Manipulating the mouse embryo.: Cold Spring Harbour Press.
Hole, N. and Stern, P. L. (1988) Br. J. Cancer, 57, 239-46, (1988).
Hole, N. and Stern, P. L. (1990) Int J Cancer 45, 179-84.

Home-Office. (1986). Guidance on the Operation of the Animals (Scientific Procedures Act) 1986. *HMSO.*

Itskovitz-Eldor, J., Schuldiner, M., Karsenti, D., Eden, A, Yanuka, O., Amit, M., Soreq, H. and Benvenisty, N. (2000). *Mol Med* 6, 88-95.

Janosi, J. B., Ramsland, P. A., Mott, M. R., Firth, S. M., Baxter, R. C. and Delhanty, P. J. (1999) J Biol Chem 274, 23328-32.

Johansson, B. M. and Wiles, M. V. (1995). *Mol Cell Biol* 15, 141-51.

Kajava, A. V., Vassart, G. and Wodak, S. J. (1995) Structure 3, 867-77.

King, K. W., Sheppard, F. C., Westwater, C., Stern, P. L. and Myers, K. A. (1999). *Biochim Biophys Acta* 1445, 257-70.

Kobe, B. and Deisenhofer, J. (1994) Trends Biochem Sci 19, 415-21.

Kobe, B. and Deisenhofer, J. (1995) Proteins with leucine-rich repeats. Curr Opin Struct Biol 5,409-16.

Kohler, G. and Milstein, C. (1976) Eur J Immunol 6, 511-9.

Laemmli, U. K. (1970) Nature 227, 680-5.

Lake, J., Rathjen, J., Remiszewski, J. and Rathjen, P. D. (2000). *J Cell Sci* 113, 555-66.

Lemoine, F. J. and Marriott, S. J. (2001) J Biol Chem 276, 31851-7.

Li, X. et al. *J Cell Biol* 153, 811-22. (2001).

Ling, V. and Neben, S. (1997). *J Cell Physiol* 171, 104-15.

Moustakas, A, Theodoropoulos, P. A., Gravanis, A., Haussinger, D. and Stournaras, C. (1998) Contrib Nephrol 123, 121-34.

Mulder, W. M., Stern, P. L., Stukat, M. J., de Windt, E., Butzelaar, R. M., Meijer, S., Ader, H. J., Claessen, A. M., Vermorken, J. B., Meijer, C. J. et al. (1997). *Clin Cancer Res* 3, 1923-30.

Myers, K. A., Rahi-Saund, V., Davison, M. D., Young, J. A., Cheater, A. J. and Stern, P. L. (1994) J Biol Chem 269, 9319-24.

Niwa, H., Miyazaki, J. and Smith, A. G. (2000). *Nat Genet* 24, 372-6.

Rathjen J, H. B., Hudson K M, Nesci A, Dunn S, Rathjen P D. (2002). *Development.* 129, 2649-61.

Rathjen, J., Lake, J. A., Bettess, M. D., Washington, J. M., Chapman, G. and Rathjen, P. D. (1999). *J Cell Sci* 112, 601-12.

Reubinoff et al, Nature Biotechnology 18:399-404, 2000

Sato, M. and Nakano, T. (2001). *Intern Med* 40, 195-200.

Schliess, F. and Haussinger, D. (2000) Cell Physiol Biochem 10, 403-8.

Shaw D M, W. A., Myers K A, Westwater C, Rahi-Saund V, Davies M J, Renouf D V, Hounsell E F, Stern P L. (2002). *Biochem J* 363, 137-45.

Shaw D M, Embleton M J, Westwater C, Ryan M G, Myers K A, Kingsman S M, Carroll M W, Stern P L. Biochim Biophys Acta. 2000 Dec. 15; 1524(2-3):238-46.

Smith, A. (2001). *Annu Rev Cell Dev Biol* 17, 435-462.

Smith, A. G. (1992). *Semin Cell Biol* 3, 385-99.

Southall P. J., Boxer, G. M., Bagshawe, K. D., Hole, N., Bromley, M. and Stern, P. L. (1990). *Br J Cancer* 61, 89-95.

Starzynska, T., Marsh, P. J., Schofield, P. F., Roberts, S. A., Myers, K. A. and Stern, P. L. (1994). *Br J Cancer* 69, 899-902.

Starzynska T., Rahi, V. and Stern, P. L. (1992) Br J Cancer 66, 867-9.

Starzynska, T., Wiechowska-Kozlowska, A., Marlicz, K., Bromley, M., Roberts, S. A., Lawniczak, M., Kolodziej, B., Zyluk, A and Stern, P. L. (1998). *Eur J Gastroenterol Hepatol* 10, 479-84.

Thorey, I. S. et al. *Mol Cell Biol* 18, 3081-8. (1998).

Wakayama, T., Rodriguez, I., Perry, A. C., Yanagimachi, R. & Mombaerts, P. *Proc Natl Acad Sci USA* 96, 14984-9. (1999).

Ward C M, Stern P. (2002a). *Stem Cells* 20, 472-475.

Ward C M, Stern P, Willington M, Fleimiken A M. (2002b). *Lab Invest* 82, 1765-1767.

Weinhold, B., Schratt, G., Arsenian, S., Berger, J., Kamino, K., Schwarz, H., Ruther, U. and Nordheim, A. (2000). *Embo J* 19, 5835-44.

Willison, K. R. and Stern, P. L. (1978). *Cell* 14, 785-93.

Woods A M, W. W., Shaw D M, Ward C M, Carroll M W, Thomas B and Stern P L. (2002). *Biochem J* 366, 353-365.

Wrigley, E., McGown, A. T., Rennison, J., Swindell, R., Crowther, D., Starzynska, T. and Stern, P. L. (1995). *Int J Gynecol Cancer* 5, 269-274.

Yilma, T., Ristow, S. S., Moss, B. and Jones, L. (1987) Hybridoma 6, 329-35.

Zhande, R. and Brownsey, R. W. (1996) Biochem Cell Biol 74, 513-22.

All publications mentioned in the above specification, and references cited in said publications, are herein incorporated by reference. Various modifications and variations of the described methods and system of the present invention will be apparent to those skilled in the art without departing from the scope and spirit of the present invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A method for detecting the differentiation status of cells in a population of mammalian pluripotent stem cells comprising detecting cell surface expression of 5T4 antigen on cells in the population of mammalian pluripotent stem cells, wherein 5T4 expression indicates cells in the population that are undergoing differentiation.

2. A method as claimed in claim 1 wherein said population of mammalian pluripotent stem cells comprise embryonic stem cells, embryonic germ cells or embryonal carcinoma cells.

3. A method as claimed in claim 1 wherein said mammalian pluripotent stem cells are murine, human, primate, porcine, feline, bovine, ovine or canine.

4. A method of claim 1 wherein said cell surface expression of 5T4 is detected by anti-5T4 antibodies.

5. A method of detecting differentiation status of a population of mammalian pluripotent stem cells comprising the steps of:
   a) obtaining cells from the population of mammalian pluripotent stem cells;
   b) incubating said cells with a anti-5T4 antibody such that specific binding of anti-5T4 antibody to 5T4 antigen occurs; and
   c) detecting said binding of said antibody wherein binding of the anti-5T4 antibody to cells is indicative of the presence of 5T4 and stem cells undergoing differentiation.

6. A method of separating undifferentiated mammalian pluripotent stem cells from mammalian stem cells undergoing differentiation within a population of mammalian stem cells comprising:
   a) incubating the population of mammalian stem cells with anti-5T4 antigen antibody such that the antibody specifically binds to a cell expressing cell surface 5T4 antigen;
   b) separating cells bound to the antibody from cells with no bound antibody; and
   c) isolating either the bound or unbound cells,
   wherein cell surface 5T4 antigen expression indicates cells that are undergoing differentiation.

7. A method as claimed in claim 6 wherein said isolated cells are viable.

8. The method according to claim 5, wherein the anti-5T4 antibody is labeled.

9. The method according to claim 6, wherein the anti-5T4 antibody is labeled.

10. The method according to claim 6, wherein the anti-5T4 antibody is immobilized.

* * * * *

UNITED STATES PATENT AND TRADEMARK OFFICE
CERTIFICATE OF CORRECTION

PATENT NO. : 7,662,625 B2  Page 1 of 1
APPLICATION NO. : 10/520502
DATED : February 16, 2010
INVENTOR(S) : Pater Stern et al.

It is certified that error appears in the above-identified patent and that said Letters Patent is hereby corrected as shown below:

On the Title Page:

Please insert Related U.S. Application Data, field (63), as follows:

--Related U.S. Application Data

(63) This application is a U.S. National Phase under 35 U.S.C. § 371 of PCT/GB2003/002836, filed July 2, 2003, which claims benefit of priority from U.S. Patent Application 10/485,655, filed October 9, 2003 and GB Patent Application 0215287.4, filed July 2, 2002.--

Title Page, Item (30), please delete "(DE) 0215287" and insert --(GB) 0215287.4--.

Signed and Sealed this

Twenty-first Day of December, 2010

David J. Kappos
*Director of the United States Patent and Trademark Office*